US009517977B2

(12) United States Patent
Spreitzer et al.

(10) Patent No.: US 9,517,977 B2
(45) Date of Patent: Dec. 13, 2016

(54) MATERIALS FOR ELECTRONIC DEVICES

(75) Inventors: Hubert Spreitzer, Viernheim (DE); Jochen Schwaiger, Frankfurt am Main (DE); Heinrich Becker, Hofheim (DE)

(73) Assignee: Merck Patent GmbH, Darmstadt (DE)

( * ) Notice: Subject to any disclaimer, the term of this patent is extended or adjusted under 35 U.S.C. 154(b) by 1140 days.

(21) Appl. No.: 13/504,553

(22) PCT Filed: Oct. 1, 2010

(86) PCT No.: PCT/EP2010/006015
§ 371 (c)(1),
(2), (4) Date: Apr. 27, 2012

(87) PCT Pub. No.: WO2011/050888
PCT Pub. Date: May 5, 2011

(65) Prior Publication Data
US 2012/0211701 A1 Aug. 23, 2012

(30) Foreign Application Priority Data
Oct. 29, 2009 (DE) ........................ 10 2009 051 172

(51) Int. Cl.
*H01L 51/50* (2006.01)
*C07B 59/00* (2006.01)
*H01L 51/00* (2006.01)

(52) U.S. Cl.
CPC ........... *C07B 59/00* (2013.01); *H01L 51/0067* (2013.01); *H01L 51/0072* (2013.01); *H01L 51/5012* (2013.01)

(58) Field of Classification Search
None
See application file for complete search history.

(56) References Cited

U.S. PATENT DOCUMENTS

2004/0170863 A1* 9/2004 Kim et al. ..................... 428/690
2010/0187505 A1   7/2010 Stoessel et al.
2011/0095273 A1* 4/2011 Meng et al. ..................... 257/40

FOREIGN PATENT DOCUMENTS

| EP | 2332911 A2 | 6/2011 |
| JP | 2012-500789 A | 1/2012 |
| JP | 2013-505982 A | 2/2013 |
| WO | WO-2008/145239 A2 | 12/2008 |
| WO | WO-2011/040939 A1 | 4/2011 |

OTHER PUBLICATIONS

Buu-Hoi et al.; Enhancement of the Carcinogenicity of 7,12-Dimethylbenz[a] anthracene Through Replacement of Hydrogen by Deuterium: a New Biological Isotope Effect; 1971; Nasturwissenschlen, 58(7), p. 317.*

Cavalieri et al., Charge Localization in the Carbonium Ions of Methylbenzanthracene, 1976; Journal of Organic Chemistry, vol. 41, No. 16, p. 2679-2679.*
Stephens, et al., "Synthesis of Deuterium-Labelled 2,5-Bis(4-Amidinophenyl)Furan, 2,5-Bis[4-Methoxyamidino)Phenyl]Furan, and 2,7-Diamidinocarbazole", Journal of Labelled Compounds and Radiopharmaceuticals, vol. 44, (2001), pp. 197-208.
Smith, et al., "Substituent Effects on Aromatic Proton Chemical Shifts", The Journal of Physical Chemistry, vol. 74, (1970), pp. 812-821.
Akawie, R.I., "Synthesis of Deuterated Biphenyls", J. Org. Chem., vol. 26, (1961), pp. 243-245.
Cooks, et al., "Studies in Mass Spectrometry", Journal of the American Chemical Society, vol. 90, No. 15, (1968), pp. 4064-4069.
Biehl, et al., "ESR, NMR, and ENDOR Studies of Partially Deuterated Phenyl Substituted Anthracenes", Journal of the American Chemical Society, vol. 99, No. 13, (1977), pp. 4278-4286.
International Search Report for PCT/EP2010/0006015 mailed Jan. 11, 2011.
Gäumann et al., "Pyrolyse von Aromaten. 1. Mitteilung. Biphenyl", Helvetica Chimica Acta, vol. 45, No. 5, pp. 1563-1571 (1962).
Naturwissenschaften, vol. 58, No. 7, pp. 371 (1971).
Biehl et al., "Untersuchung der π—σ-delokalisation an den radikalionen desrubrens mit endor inlösung", Tetrahedron, vol. 29, No. 2, pp. 363-368 (1973).
Cheung et al., "14C- and 2H-labelled 7-methylbenz[c]acridine", Journal of Labelled Compounds and Radiopharmaceuticals, vol. 17, No. 1, pp. 121-128 (1980).
Ozasa et al., "Syntheses and Physical Properties of Several Deuterium-labelled Polyphenyls", Chemical & Pharmaceutical Bulletin, vol. 29, No. 2, pp. 370-378 (1981).
Hsing et al., "Oligomers from Biphenyl, Biphenyl-$d_{10}$, or p-Terphenyl with Aluminum Chloride—Cupric Chloride: Mechanism, ESR, and Conductivity", Journal of Polymer Science, Polymer Chemitry Edition, vol. 21, No. 2, pp. 457-466 (1983).
Ozasa et al., "Syntheses and spectral properties of several branched-chain polyphenyls containing 1,2,3-trisubstituted ring(s)", Chemical & Pharmaceutical Bulletin, vol. 31, No. 5, pp. 1572-1581 (1983).
Phillips et al., "Giancing-Angle Neutron Diffraction from Smectic C Liquid-Crystal Surfaces", Journal of Applied Crystallography, vol. 30, No. 6, pp. 1096-1104 (1997).
Brown et al., "An Investigation of ??? Packing in a Columnar Hexabenzocoronene by Fast Magic-Angle Spinning and Double-Quantum 1H Solid-State NMR Spectroscopy", Journal of the American Chemical Society, vol. 121, No. 28, pp. 6712-6718 (1999).
Miura et al., "*Magnetic Interaction* of Pyridyl-Substituted Thioaminyl Stable Free Radicals", Journal of Organic Chemistry, vol. 68, No. 4, pp. 1225-1234 (2003).
Shurvell, et al., "The Infrared Spectrum of 2,4,6-Triphenyl-$d_{15}$-1,3,5-Triazine", Spectrochimica Acta, vol. 23A, pp. 1313-1318 (1967).

* cited by examiner

*Primary Examiner* — Gregory Clark
(74) *Attorney, Agent, or Firm* — Drinker Biddle & Reath LLP

(57) ABSTRACT

The present invention relates to compounds of the formula (I), to mixtures of the said compounds with emitter compounds, to the use of compounds of the formula (I) and the said mixtures in electronic devices, and to electronic devices containing one or more compounds of the formula (I) and/or mixtures of compounds of the formula (I) with emitter compounds.

20 Claims, No Drawings

MATERIALS FOR ELECTRONIC DEVICES

CROSS-REFERENCE TO RELATED APPLICATIONS

This application is a national stage application (under 35 U.S.C. §371) of PCT/EP2010/006015, filed Oct. 1, 2010, which claims benefit of German application 10 2009 051 172.5, filed Oct. 29, 2009.

The present invention relates to deuterated compounds of the general formula (I) which can be used in electronic devices, preferably as host materials in organic electroluminescent devices (OLEDs). The invention furthermore relates to mixtures of the compounds according to the invention with emitter compounds and to electronic devices containing the compounds according to the invention and/or the above-mentioned mixtures.

Organic semiconductors such as the compounds according to the invention are frequently used as functional materials in the electronics industry.

In particular, they are used in organic electroluminescent devices (OLEDs), the general structure of which is described, inter alia, in U.S. Pat. Nos. 4,539,507 and 5,151,629. OLEDs have a number of attractive properties, inter alia potentially low energy consumption at the same time as high achievable luminance and excellent colour contrast, meaning that it is expected that they will in future play an important role as colour displays and as light sources in room lighting.

In accordance with the prior art, fluorescent OLEDs principally use condensed aromatic compounds, in particular anthracene derivatives, as host materials, especially for blue-emitting electroluminescent devices, for example 9,10-bis(2-naphthyl)anthracene (U.S. Pat. No. 5,935,721). WO 03/095445 and CN 1362464 disclose 9,10-bis(1-naphthyl) anthracene derivatives for use in OLEDs. Further anthracene derivatives are disclosed in the patent applications WO 01/076323, WO 01/021729, WO 04/013073, WO 04/018588, WO 03/087023, WO 04/01858, WO 07/021,117, WO 08/145,239 and WO 07/114,358. Host materials based on aryl-substituted pyrenes and chrysenes are disclosed in the application WO 04/016575.

However, there continues to be a demand for novel materials, especially organic compounds, which can be used in the said devices and preferably result in an improvement in the property profile of the devices, in particular in the following points:
  an increase in the lifetime of the device
  an increase in the power efficiency of the device, especially an increase in the light yield at low current flow and low operating voltage
  an improvement in the colour accuracy of the device, in particular in the case of blue-emitting devices.

In addition, an improvement in the processing properties is also necessary for mass production. For the purposes of the present invention, these are taken to mean, inter alia, improved thermal stability, improved vapour-deposition behaviour and reduced crystallinity for vacuum-based production processes, or improved solubility and improved film formation for solution-based production processes.

The technical object is thus to develop novel materials for organic electroluminescent devices which have a positive influence on the property profile of the devices, in particular in the above-mentioned points.

This object is achieved in accordance with the invention by the provision of deuterated compounds of the formula (I) and the use thereof in organic electroluminescent devices, preferably as host materials for fluorescent emitters.

A further important aspect in the production of organic electroluminescent devices is the requisite high purity of the materials employed, which can in many cases only be achieved by means of sublimation. Even extremely small amounts of impurities can considerably reduce the lifetime and efficiency of the electroluminescent device.

It is furthermore desirable to provide compounds having high sublimation stability, since the compounds must have high stability under the conditions prevailing during sublimation in order to obtain the compounds in high purity by sublimation.

A further aspect in this connection is synthetic accessibility to the compounds. It should be possible to prepare the compounds in question in the fewest possible steps, which proceed in good yield. In addition, the starting materials should be readily available.

The prior art discloses organic aromatic compounds for use as functional materials, in particular as fluorescent emitters, which are substituted on their backbone by one or more deuterium atoms, for example pyrene derivatives (U.S. Pat. No. 6,852,429) or anthracene derivatives (US 2006/0115678 and KR 10-2009-0086015). The use of deuterated organic, in particular polymeric, compounds in OLEDs is disclosed in the application WO 02/47440.

Surprisingly, it has now been found that compounds of the formula (I) which contain one or more deuterated groups Y bonded to a backbone Z have excellent sublimation properties. They can be sublimed at high temperatures without decomposition and can therefore be obtained in high purity. In addition, the applicational properties are improved in some aspects compared with analogous undeuterated compounds.

Furthermore, they are readily accessible synthetically owing to their modular structure $Z—(Y)_n$.

The invention thus relates to a compound of the general formula (I)

$$Z—(Y)_n \hspace{2cm} \text{formula (I)}$$

where
Z represents an aryl or heteroaryl group having 15 to 60 aromatic ring atoms, which may be substituted by one or more radicals R, or represents an oligoarylene or oligoheteroarylene having 18 to 60 aromatic ring atoms, which may be substituted by one or more radicals R, where the oligoarylene or oligoheteroarylene contains exclusively aromatic rings of the formula (II),

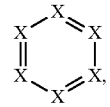

formula (II)

where X in formula (II) is, identically or differently, either CR or N, with the proviso that not more than 2 adjacent X simultaneously correspond to N; and where furthermore radicals R on groups of the formula (II) cannot form rings fused to these six-membered rings;
Y, identically or differently on each occurrence, represents a phenyl, biphenyl, terphenyl, diphenyltriazinyl, naphthyl, methyl, pyridinyl, pyrimidinyl, pyrazinyl, triazinyl, thiophenyl, furanyl, quinolinyl, isoquinolinyl, imidazolyl, benzimidazolyl or quinazolinyl group, each of which carries two or more deuterium atoms and may optionally be substituted by one or more radicals $R^1$, where two or more groups Y can be connected to one another either via single bonds or via one or more radicals $R^1$;

n can adopt a value from 1 to 15;

R, $R^1$, identically or differently on each occurrence, represent H, D, F, Cl, Br, I, CN, $Si(R^2)_3$, $NO_2$ or a straight-chain alkyl, alkoxy or thioalkoxy group having 1 to 40 C atoms or an alkenyl or alkynyl group having 2 to 40 C atoms or a branched or cyclic alkyl, alkoxy or thioalkoxy group having 3 to 40 C atoms, each of which may be substituted by one or more radicals $R^2$, where one or more adjacent or non-adjacent $CH_2$ groups may be replaced by —C≡C—, —$R^2$C=C$R^2$—, $Si(R^2)_2$, C=O, C=S, C=Se, C=N$R^2$, P(=O)($R^2$), SO, $SO_2$, $NR^2$, O, S, C(=O)O or C(=O)N$R^2$, or an aromatic or heteroaromatic ring system having 5 to 60 ring atoms, which may in each case be substituted by one or more radicals $R^2$; two or more substituents R or $R^1$ on the group Z and/or on one or more of the groups Y may be linked to one another and optionally form a mono- or polycyclic aliphatic, aromatic or heteroaromatic ring system; and $R^2$ on each occurrence, identically or differently, represents H, D or an aliphatic, aromatic or heteroaromatic organic radical having 1 to 20 C atoms, in which, in addition, one or more H atoms may be replaced by D or F; two or more adjacent or non-adjacent radicals $R^2$ here may be linked to one another and optionally form a mono- or polycyclic aliphatic, aromatic or heteroaromatic ring system.

For the purposes of the invention, substitution by a deuterium atom is taken to mean that a deuterium atom is located at the relevant position(s) of the compound with a statistical probability of 10 to 100%, preferably 90 to 100%, and a hydrogen atom is located at the relevant position(s) of the compound with a probability of between 90 and 0%, preferably between 10 and 0%. The corresponding situation applies to analogous terms used in the present application, such as, for example, "compound which carries two or more deuterium atoms" or "compound which is fully substituted by deuterium".

Consequently, compounds which contain deuterium atoms merely in a frequency which corresponds to their natural occurrence or generally in lower enrichment than mentioned above do not fall under this definition and are not regarded as deuterium-substituted for the purposes of the invention.

An aryl group in the sense of this invention is defined as containing 6 to 60 C atoms; a heteroaryl group in the sense of this invention contains 1 to 60 C atoms and at least one heteroatom, with the proviso that the sum of C atoms and heteroatoms is at least 5. The heteroatoms are preferably selected from N, O, Si, B, P and S.

An aryl group or heteroaryl group here is taken to mean either a simple aromatic ring, i.e. benzene, or a simple heteroaromatic ring, for example pyridine, pyrimidine, thiophene, etc., or a condensed (fused) aromatic or heteroaromatic polycycle, for example naphthalene, anthracene, phenanthrene, pyrene, quinoline, isoquinoline, carbazole, etc., or a condensed (fused) aromatic or heteroaromatic polycycle additionally containing one or more non-aromatic ring atoms, such as, for example, spirobifluorene, indenofluorene or indenocarbazole.

A condensed (fused) aromatic or heteroaromatic polycycle in the sense of the present application is taken to mean an aryl or heteroaryl group which consists of two or more simple aromatic or heteroaromatic rings condensed to one another. Unless explicitly indicated, the condensed aromatic or heteroaromatic polycycle does not contain any non-aromatic ring atoms. If it contains non-aromatic ring atoms, it is referred to as an aromatic or heteroaromatic polycycle containing one or more non-aromatic ring atoms.

Non-aromatic ring atoms in the aryl groups defined above are taken to mean ring atoms which, owing to their hybridisation, are not part of the conjugated system of double bonds of the aryl or heteroaryl group, for example carbon atoms having four substituents ($sp^3$-hybridised carbon atoms) or silicon atoms having four substituents. In the above-mentioned compounds spirobifluorene, indenofluorene and indenocarbazole, for example, the spiro carbon atom of the spirobifluorene and the alkylene bridge in the five-membered rings of the indenofluorene or in the five-membered ring of the indenocarbazole represent non-aromatic ring atoms in the sense of this definition.

In the above-mentioned definition of the group Z as an aryl group having 15 to 60 aromatic ring atoms and in all analogous definitions below, the non-aromatic ring atoms as defined above are not counted as aromatic ring atoms. Correspondingly, a spirobifluorene contains 24 aromatic ring atoms, an indenofluorene contains 18 aromatic ring atoms and an indenocarbazole contains 19 aromatic ring atoms.

An aryl or heteroaryl group as defined above, which may in each case be substituted by the above-mentioned radicals R or $R^1$ and which may be linked via any desired positions on the aromatic or heteroaromatic group, is taken to mean, in particular, groups derived from benzene, naphthalene, anthracene, phenanthrene, pyrene, dihydropyrene, chrysene, perylene, fluoranthene, fluorene, spirobifluorene, cis- or trans-indenofluorene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An oligoarylene or oligoheteroarylene in the sense of this invention is taken to mean a system which contains three or more aromatic or heteroaromatic rings, which are connected to one another exclusively via single bonds. The aromatic or heteroaromatic rings here may represent simple aromatic or heteroaromatic rings, such as, for example, benzene, pyridine, pyrimidine or thiophene, or condensed aromatic or heteroaromatic polycycles, such as, for example, naphthalene, anthracene, phenanthrene, pyrene, quinoline, isoquinoline or carbazole. Examples of oligoarylenes or oligoheteroarylenes in accordance with the present definition are terphenyl, terpyridine, quaterphenyl and diphenyltriazine.

An aromatic ring system in the sense of this invention contains 6 to 60 C atoms in the ring system. A heteroaromatic ring system in the sense of this invention contains 5 to 60 aromatic ring atoms, of which at least one represents a heteroatom. The heteroatoms are preferably selected from N, O, Si, B, P and S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an sp$^3$-hybridised C, Si, N or O atom, an sp$^2$-hybridised C or N atom or an sp-hybridised C atom. Thus, for example, systems such as triarylamine, diaryl ether, stilbene, etc. are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic or heteroaromatic ring systems in the sense of this invention, for example systems such as biphenyl, terphenyl or diphenyltriazine.

An aromatic or heteroaromatic ring system having 5-60 aromatic ring atoms, which may in each case also be substituted by radicals as defined above and which may be linked via any desired positions on the aromatic or heteroaromatic group, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or CH$_2$ groups may be substituted by the groups mentioned above in the definition of the radicals R and R$^1$, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

It is preferred in accordance with the invention for the group Z to represent an aryl or heteroaryl group having 15 to 40 aromatic ring atoms, which may be substituted by one or more radicals R, or an oligoarylene or oligoheteroarylene having 18 to 36 aromatic ring atoms, which may be substituted by one or more radicals R, where the oligoarylene or oligoheteroarylene contains exclusively aromatic rings of the formula (II), as defined above.

The group Z particularly preferably represents an aryl or heteroaryl group having 15 to 30 aromatic ring atoms, which may be substituted by one or more radicals R.

The group Z very particularly preferably represents a condensed aromatic or heteroaromatic polycycle containing 15 to 30 aromatic ring atoms, which may be substituted by one or more radicals R.

The group Z is preferably selected from terphenyl, diphenyltriazine, tetraphenylene, triphenylamine, pyridinebiphenyl, phenylbipyridine, phenylcarbazole, benzophenanthrene, pyrene, benzopyrene, pentacene, benzanthracene, naphthacene, chrysene, triphenylene, dibenzochrysene, perylene, spirobidibenzosilole, spirobifluorene, spirofluorenanthrone, spirofluoreneacridane, spirofluorenedibenzocycloheptatriene, indenofluorene, benzocarbazole, dibenzocarbazole, diindenofluorene, benzindenofluorene, dibenzindenofluorene, benzophenanthroline, benzacridine, benzacridone, fluoranthene, benzofluoranthene, benzophenanthridine, benzophenazine, benzonaphthofuran, benzonaphthothiophene, acephenanthrylene, quinacridones, which may be linear or angular, benzofluoranthene, benzimidazolequinazoline, dibenzoquinoline, dibenzoquinoxaline, dibenzoisoindole, dibenzocinnoline, dibenzophthalazine, dibenzoquinazoline, naphthoquinoline, aceanthrylene, indolocarbazole, indenocarbazole, phenanthrocarbazole, phenanthrimidazole, benzocarboline, anthroxazole, phenanthroxazole, pyrenyltriazine, dibenzazepine, truxene, truxenone and sumanene, each of which may optionally be substituted by one or more radicals R.

The group Z is particularly preferably selected from terphenyl, triphenylene, benzocarbazole, benzonaphthofuran, benzophenanthrene, pyrene, benzopyrene, fluoranthene, benzanthracene, spirobidibenzosilole, spirobifluorene, indenofluorene, benzindenofluorene, indolocarbazole, indenocarbazole, quinacridones, which may be linear or angular, dibenzoquinoxaline, dibenzocinnoline, dibenzophthalazine, dibenzoquinazoline and benzacridine, where the said groups may optionally be substituted by one or more radicals R.

It is preferred for the heteroaromatic ring atoms of the heteroaryl group or oligoheteroarylene which represents Z to be selected from Si, N, O, S, P and B, particularly preferably from N, O and S.

It is furthermore preferred for the group R not to represent a deuterium atom, i.e. for the group Z not to be deuterated on its backbone.

The group Y on each occurrence, identically or differently, preferably represents a phenyl, tolyl, biphenyl, terphenyl, diphenyltriazinyl, naphthyl, pyridinyl or methyl group. In a preferred embodiment of the invention, the groups Y are not linked to one another, neither by single bonds nor by radicals $R^1$.

The group Y on each occurrence, identically or differently, particularly preferably represents a phenyl, tolyl, biphenyl, terphenyl, diphenyltriazinyl, naphthyl, pyridinyl or methyl group, each of which carries two or more deuterium atoms and no further substituents apart from deuterium and hydrogen. The group Y on each occurrence, identically or differently, particularly preferably represents a phenyl, tolyl, biphenyl, terphenyl, diphenyltriazinyl, naphthyl, pyridinyl or methyl group, each of which is fully substituted b y deuterium.

Preferred embodiments of the compounds according to the invention are represented by the following formulae (III) to (XV):

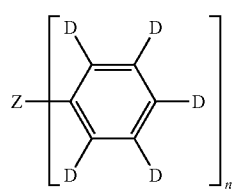

formula (III)

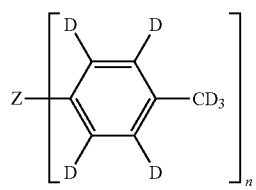

formula (IV)

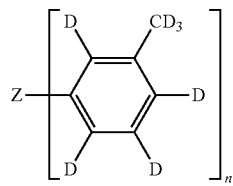

formula (V)

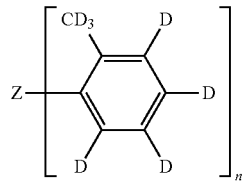

formula (VI)

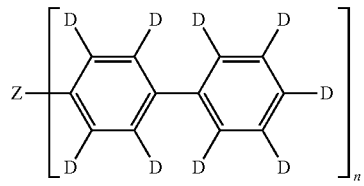

formula (VII)

-continued

formula (VIII)

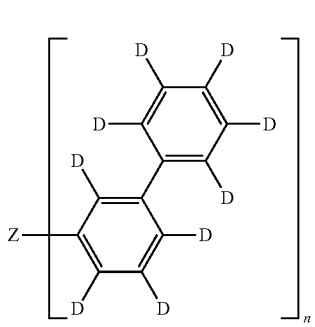

formula (IX)

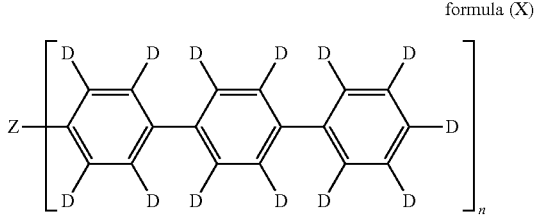

formula (X)

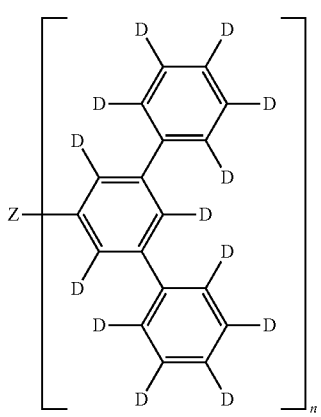

formula (XI)

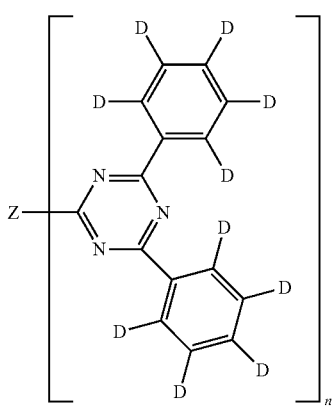

formula (XII)

formula (XIII)

formula (XIV)

formula (XV)

where the group Z and the index n are as defined above.

The radical R is preferably selected on each occurrence, identically or differently, from H, D, F, CN, $Si(R^2)_3$ or a straight-chain alkyl or alkoxy group having 1 to 20 C atoms or a branched or cyclic alkyl or alkoxy group having 3 to 20 C atoms, each of which may be substituted by one or more radicals $R^2$, where one or more adjacent or non-adjacent $CH_2$ groups may be replaced by —C≡C—, —$R^2$C=C$R^2$—, $Si(R^2)_2$, C=O, C=N$R^2$, N$R^2$, O, S, C(=O)O or C(=O)N$R^2$, or an aryl or heteroaryl group having 5 to 30 aromatic ring atoms, which may in each case be substituted by one or more radicals $R^2$.

Furthermore, the radical $R^1$ is preferably selected on each occurrence, identically or differently, from H, D, F, CN, $Si(R^2)_3$ or a straight-chain alkyl or alkoxy group having 1 to 20 C atoms or a branched or cyclic alkyl or alkoxy group having 3 to 20 C atoms, each of which may be substituted by one or more radicals $R^2$, where one or more adjacent or non-adjacent $CH_2$ groups may be replaced by —C≡C—, —$R^2$C=C$R^2$—, $Si(R^2)_2$, C=O, C=N$R^2$, N$R^2$, O, S, C(=O)O or C(=O)N$R^2$, or an aryl or heteroaryl group having 5 to 30 aromatic ring atoms, which may in each case be substituted by one or more radicals $R^2$.

The index n preferably has a value of between 1 and 10, particularly preferably a value of 1, 2, 3, 4 or 5 and very particularly preferably of 1, 2 or 3.

Particularly preferred backbones Z having the formulae Z-1 to Z-50 as constituents of the compounds of the formula (I) according to the invention are shown below. These are substituted by one or more groups Y, as defined above, and may furthermore be substituted at free positions of the aromatic or heteroaromatic skeleton by one or more radicals R.

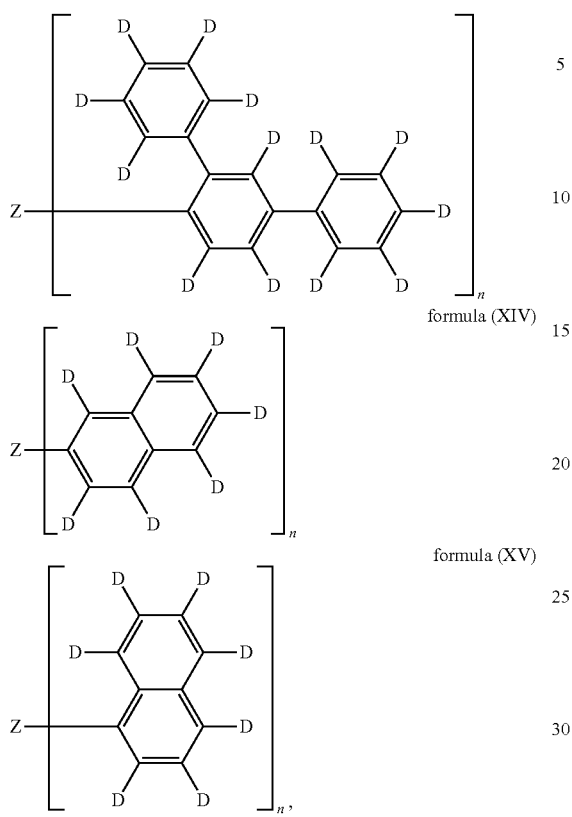

Z-1

Z-2

Z-3

Z-4

Z-5

Z-6

Z-7

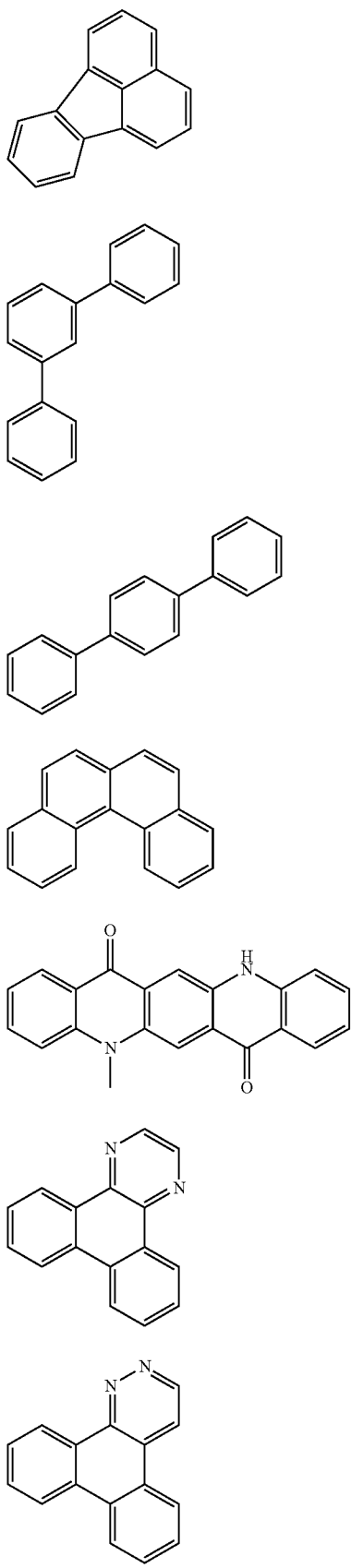
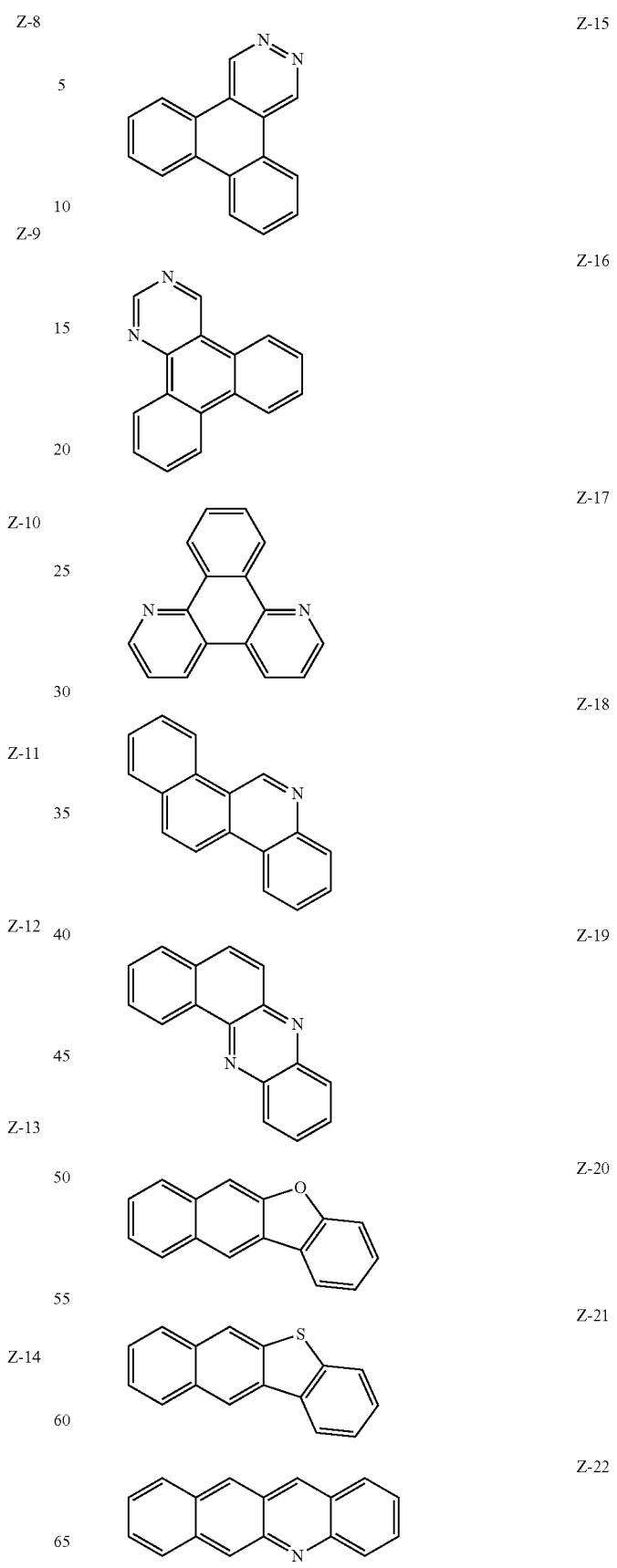

Z-23 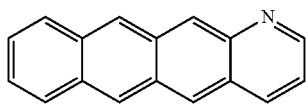
Z-24 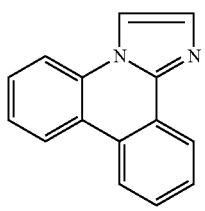
Z-25 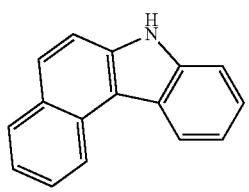
Z-26 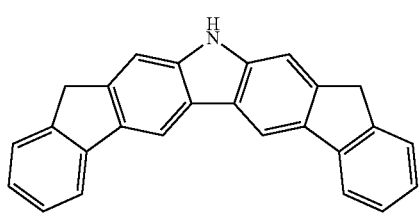
Z-27 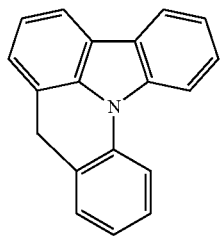
Z-28 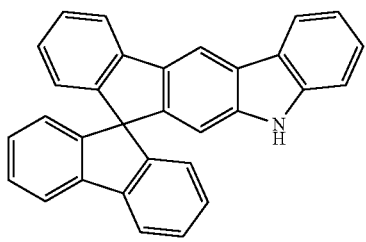
Z-29 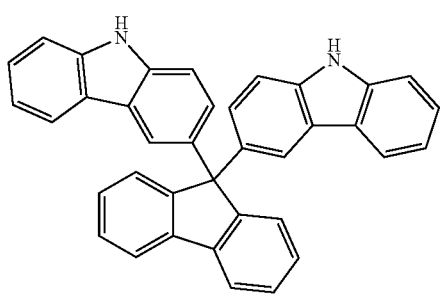
Z-30 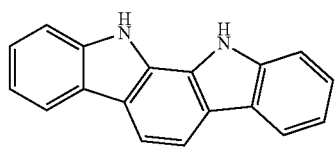
Z-31 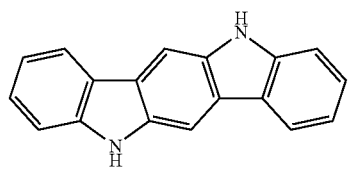
Z-32 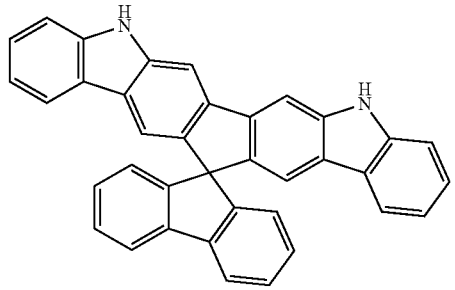
Z-33 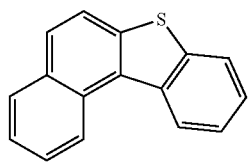
Z-34 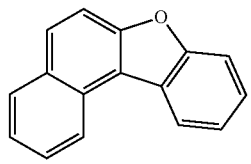
Z-35 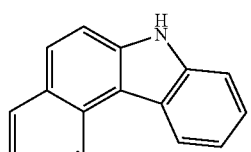
Z-36 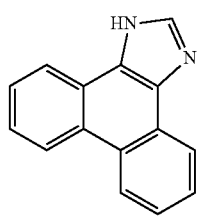
Z-37 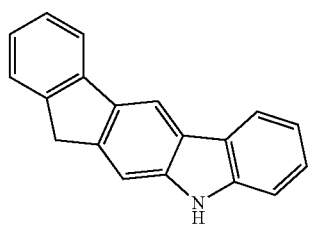

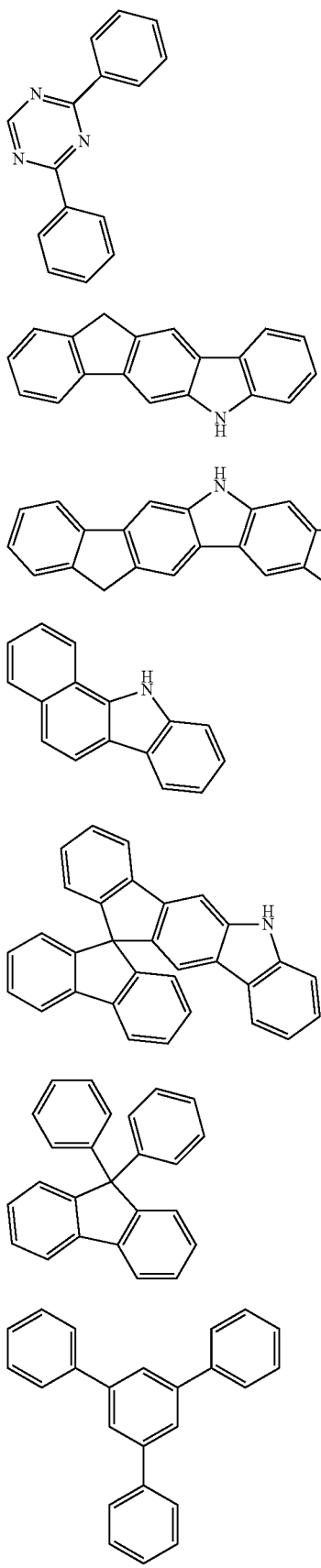
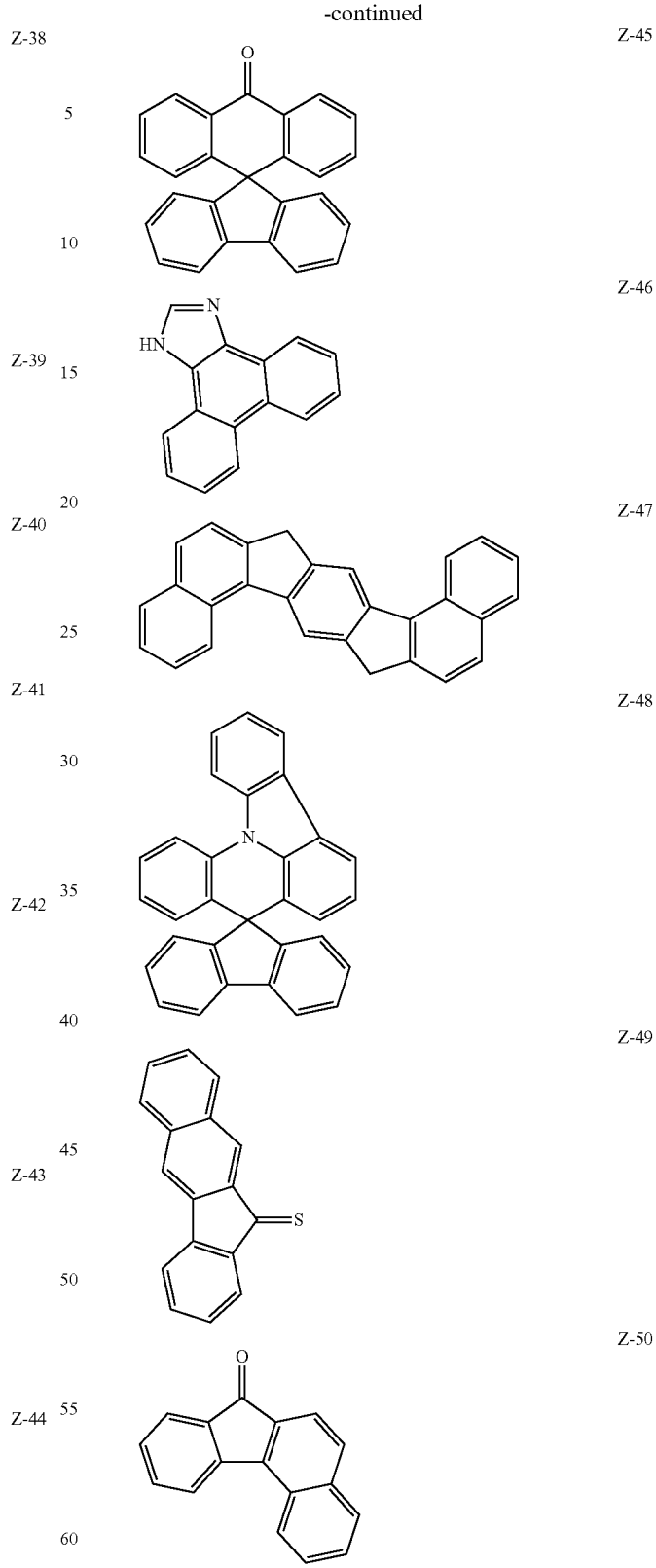
The combinations of groups Z (Z-a to Z-u) and Y (Y-1 to Y-3) listed in the following table represent particularly preferred embodiments of the compounds of the formula (I) according to the invention. The corresponding groups Z-a to Z-u and Y-1 to Y-3 are shown below.

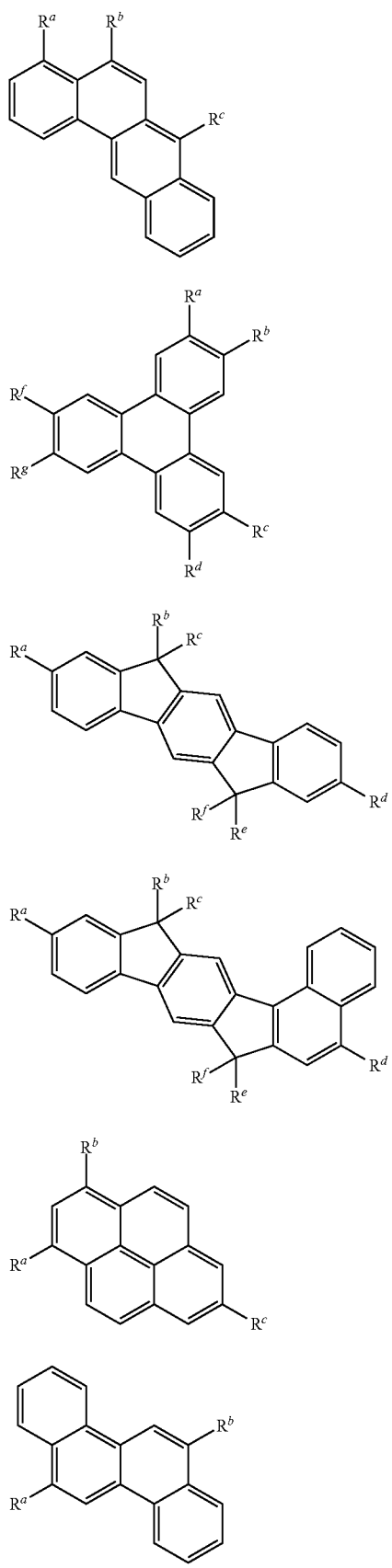
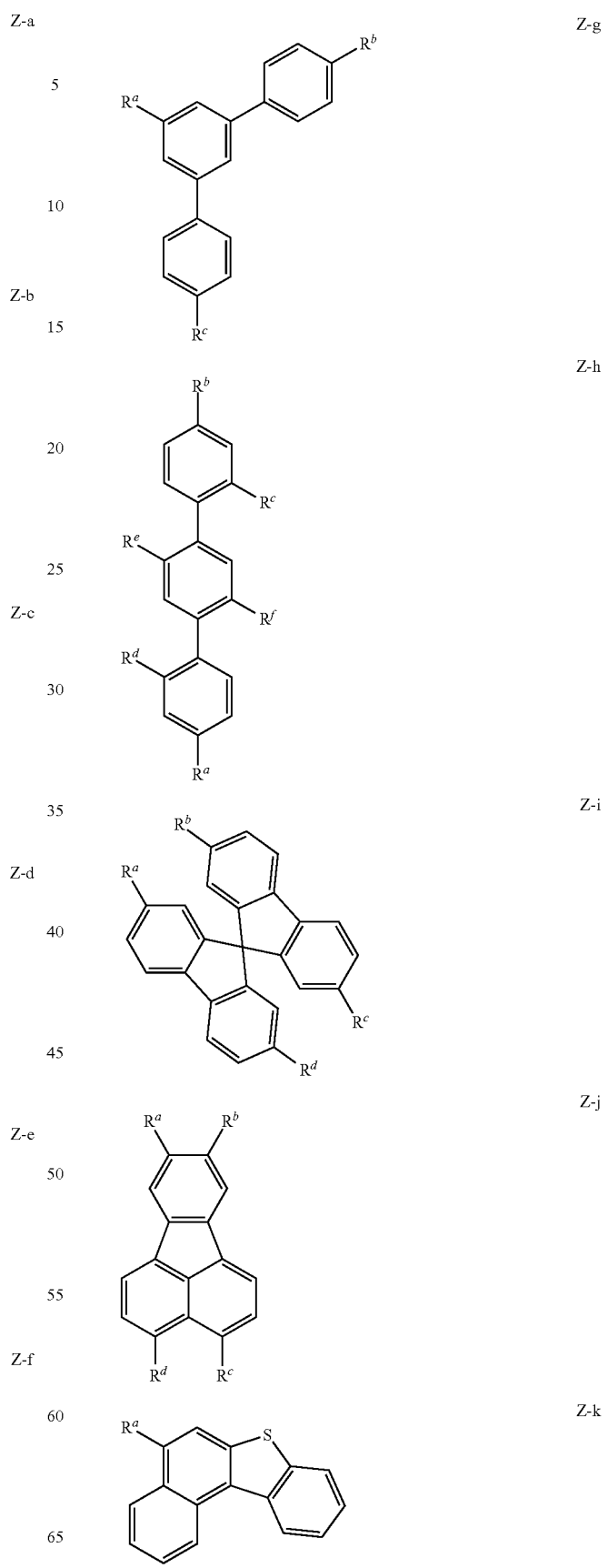
Z-a
Z-b
Z-c
Z-d
Z-e
Z-f
Z-g
Z-h
Z-i
Z-j
Z-k

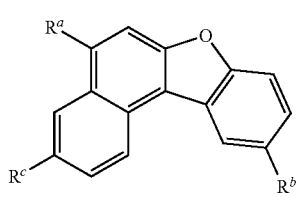 Z-l
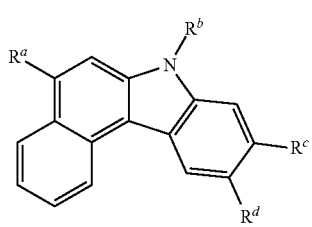 Z-m
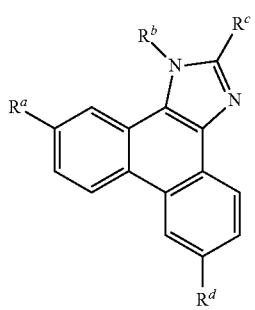 Z-n
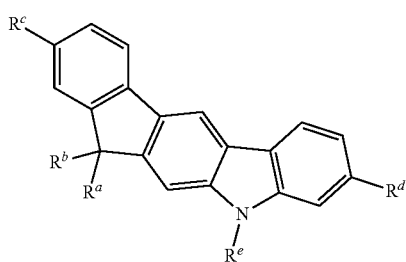 Z-o
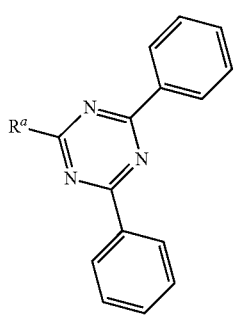 Z-p
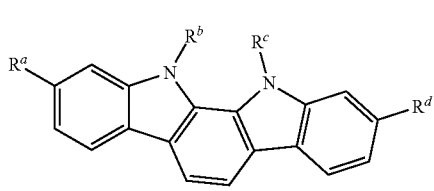 Z-q
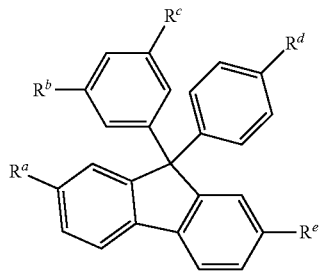 Z-r
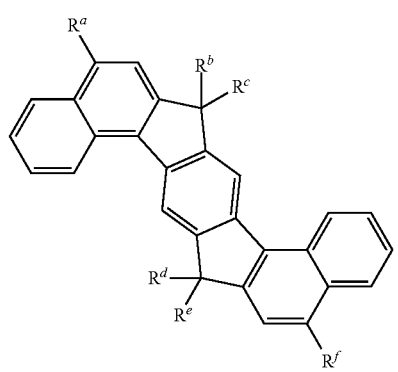 Z-s
 Z-t
 Z-u
CD₃ Y-1

-continued

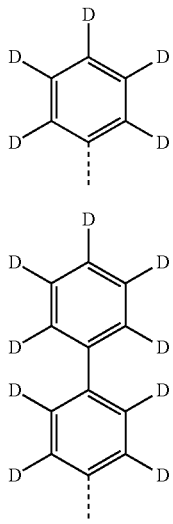

Besides groups Y-1 to Y-3, merely a hydrogen atom or any desired other group R may also be bonded at the positions denoted by $R^a$ to $R^f$. The compounds shown in the following table are particularly preferred embodiments of the compounds of the formula (I) according to the invention.

| No. | Z | $R^a$ | $R^b$ | $R^c$ | $R^d$ | $R^e$ | $R^f$ |
|---|---|---|---|---|---|---|---|
| 1 | Z-a | H | H | Y-1 | — | — | — |
| 2 | Z-a | H | H | Y-2 | — | — | — |
| 3 | Z-a | H | H | Y-3 | — | — | — |
| 4 | Z-a | H | Y-1 | H | — | — | — |
| 5 | Z-a | H | Y-1 | Y-1 | — | — | — |
| 6 | Z-a | H | Y-1 | Y-2 | — | — | — |
| 7 | Z-a | H | Y-1 | Y-3 | — | — | — |
| 8 | Z-a | H | Y-2 | H | — | — | — |
| 9 | Z-a | H | Y-2 | Y-1 | — | — | — |
| 10 | Z-a | H | Y-2 | Y-2 | — | — | — |
| 11 | Z-a | H | Y-2 | Y-3 | — | — | — |
| 12 | Z-a | H | Y-3 | H | — | — | — |
| 13 | Z-a | H | Y-3 | Y-1 | — | — | — |
| 14 | Z-a | H | Y-3 | Y-2 | — | — | — |
| 15 | Z-a | H | Y-3 | Y-3 | — | — | — |
| 16 | Z-a | Y-1 | H | H | — | — | — |
| 17 | Z-a | Y-1 | H | Y-1 | — | — | — |
| 18 | Z-a | Y-1 | H | Y-2 | — | — | — |
| 19 | Z-a | Y-1 | H | Y-3 | — | — | — |
| 20 | Z-a | Y-1 | Y-1 | H | — | — | — |
| 21 | Z-a | Y-1 | Y-1 | Y-1 | — | — | — |
| 22 | Z-a | Y-1 | Y-1 | Y-2 | — | — | — |
| 23 | Z-a | Y-1 | Y-1 | Y-3 | — | — | — |
| 24 | Z-a | Y-1 | Y-2 | H | — | — | — |
| 25 | Z-a | Y-1 | Y-2 | Y-1 | — | — | — |
| 26 | Z-a | Y-1 | Y-2 | Y-2 | — | — | — |
| 27 | Z-a | Y-1 | Y-2 | Y-3 | — | — | — |
| 28 | Z-a | Y-1 | Y-3 | H | — | — | — |
| 29 | Z-a | Y-1 | Y-3 | Y-1 | — | — | — |
| 30 | Z-a | Y-1 | Y-3 | Y-2 | — | — | — |
| 31 | Z-a | Y-1 | Y-3 | Y-3 | — | — | — |
| 32 | Z-a | Y-2 | H | H | — | — | — |
| 33 | Z-a | Y-2 | H | Y-1 | — | — | — |
| 34 | Z-a | Y-2 | H | Y-2 | — | — | — |
| 35 | Z-a | Y-2 | H | Y-3 | — | — | — |
| 36 | Z-a | Y-2 | Y-1 | H | — | — | — |
| 37 | Z-a | Y-2 | Y-1 | Y-1 | — | — | — |
| 38 | Z-a | Y-2 | Y-1 | Y-2 | — | — | — |
| 39 | Z-a | Y-2 | Y-1 | Y-3 | — | — | — |
| 40 | Z-a | Y-2 | Y-2 | H | — | — | — |
| 41 | Z-a | Y-2 | Y-2 | Y-1 | — | — | — |
| 42 | Z-a | Y-2 | Y-2 | Y-2 | — | — | — |
| 43 | Z-a | Y-2 | Y-2 | Y-3 | — | — | — |
| 44 | Z-a | Y-2 | Y-3 | H | — | — | — |
| 45 | Z-a | Y-2 | Y-3 | Y-1 | — | — | — |
| 46 | Z-a | Y-2 | Y-3 | Y-2 | — | — | — |
| 47 | Z-a | Y-2 | Y-3 | Y-3 | — | — | — |
| 48 | Z-a | Y-3 | H | H | — | — | — |
| 49 | Z-a | Y-3 | H | Y-1 | — | — | — |
| 50 | Z-a | Y-3 | H | Y-2 | — | — | — |
| 51 | Z-a | Y-3 | H | Y-3 | — | — | — |
| 52 | Z-a | Y-3 | Y-1 | H | — | — | — |
| 53 | Z-a | Y-3 | Y-1 | Y-1 | — | — | — |
| 54 | Z-a | Y-3 | Y-1 | Y-2 | — | — | — |
| 55 | Z-a | Y-3 | Y-1 | Y-3 | — | — | — |
| 56 | Z-a | Y-3 | Y-2 | H | — | — | — |
| 57 | Z-a | Y-3 | Y-2 | Y-1 | — | — | — |
| 58 | Z-a | Y-3 | Y-2 | Y-2 | — | — | — |
| 59 | Z-a | Y-3 | Y-2 | Y-3 | — | — | — |
| 60 | Z-a | Y-3 | Y-3 | H | — | — | — |
| 61 | Z-a | Y-3 | Y-3 | Y-1 | — | — | — |
| 62 | Z-a | Y-3 | Y-3 | Y-2 | — | — | — |
| 63 | Z-a | Y-3 | Y-3 | Y-3 | — | — | — |
| 64 | Z-b | H | H | H | H | H | Y-1 |
| 65 | Z-b | H | H | H | H | Y-1 | H |
| 66 | Z-b | H | H | H | H | Y-1 | Y-1 |
| 67 | Z-b | H | H | H | Y-1 | H | H |
| 68 | Z-b | H | H | H | Y-1 | H | Y-1 |
| 69 | Z-b | H | H | H | Y-1 | Y-1 | H |
| 70 | Z-b | H | H | H | Y-1 | Y-1 | Y-1 |
| 71 | Z-b | H | H | Y-1 | H | H | H |
| 72 | Z-b | H | H | Y-1 | H | H | Y-1 |
| 73 | Z-b | H | H | Y-1 | H | Y-1 | H |
| 74 | Z-b | H | H | Y-1 | H | Y-1 | Y-1 |
| 75 | Z-b | H | H | Y-1 | Y-1 | H | H |
| 76 | Z-b | H | H | Y-1 | Y-1 | H | Y-1 |
| 77 | Z-b | H | H | Y-1 | Y-1 | Y-1 | H |
| 78 | Z-b | H | H | Y-1 | Y-1 | Y-1 | Y-1 |
| 79 | Z-b | H | Y-1 | H | H | H | H |
| 80 | Z-b | H | Y-1 | H | H | H | Y-1 |
| 81 | Z-b | H | Y-1 | H | H | Y-1 | H |
| 82 | Z-b | H | Y-1 | H | H | Y-1 | Y-1 |
| 83 | Z-b | H | Y-1 | H | Y-1 | H | H |
| 84 | Z-b | H | Y-1 | H | Y-1 | H | Y-1 |
| 85 | Z-b | H | Y-1 | H | Y-1 | Y-1 | H |
| 86 | Z-b | H | Y-1 | H | Y-1 | Y-1 | Y-1 |
| 87 | Z-b | H | Y-1 | Y-1 | H | H | H |
| 88 | Z-b | H | Y-1 | Y-1 | H | H | Y-1 |
| 89 | Z-b | H | Y-1 | Y-1 | H | Y-1 | H |
| 90 | Z-b | H | Y-1 | Y-1 | H | Y-1 | Y-1 |
| 91 | Z-b | H | Y-1 | Y-1 | Y-1 | H | H |
| 92 | Z-b | H | Y-1 | Y-1 | Y-1 | H | Y-1 |
| 93 | Z-b | H | Y-1 | Y-1 | Y-1 | Y-1 | H |
| 94 | Z-b | H | Y-1 | Y-1 | Y-1 | Y-1 | Y-1 |
| 95 | Z-b | Y-1 | H | H | H | H | H |
| 96 | Z-b | Y-1 | H | H | H | H | Y-1 |
| 97 | Z-b | Y-1 | H | H | H | Y-1 | H |
| 98 | Z-b | Y-1 | H | H | H | Y-1 | Y-1 |
| 99 | Z-b | Y-1 | H | H | Y-1 | H | H |
| 100 | Z-b | Y-1 | H | H | Y-1 | H | Y-1 |
| 101 | Z-b | Y-1 | H | H | Y-1 | Y-1 | H |
| 102 | Z-b | Y-1 | H | H | Y-1 | Y-1 | Y-1 |
| 103 | Z-b | Y-1 | H | Y-1 | H | H | H |
| 104 | Z-b | Y-1 | H | Y-1 | H | H | Y-1 |
| 105 | Z-b | Y-1 | H | Y-1 | H | Y-1 | H |
| 106 | Z-b | Y-1 | H | Y-1 | H | Y-1 | Y-1 |
| 107 | Z-b | Y-1 | H | Y-1 | Y-1 | H | H |
| 108 | Z-b | Y-1 | H | Y-1 | Y-1 | H | Y-1 |
| 109 | Z-b | Y-1 | H | Y-1 | Y-1 | Y-1 | H |
| 110 | Z-b | Y-1 | H | Y-1 | Y-1 | Y-1 | Y-1 |
| 111 | Z-b | Y-1 | Y-1 | H | H | H | H |
| 112 | Z-b | Y-1 | Y-1 | H | H | H | Y-1 |
| 113 | Z-b | Y-1 | Y-1 | H | H | Y-1 | H |
| 114 | Z-b | Y-1 | Y-1 | H | H | Y-1 | Y-1 |
| 115 | Z-b | Y-1 | Y-1 | H | Y-1 | H | H |
| 116 | Z-b | Y-1 | Y-1 | H | Y-1 | H | Y-1 |
| 117 | Z-b | Y-1 | Y-1 | H | Y-1 | Y-1 | H |
| 118 | Z-b | Y-1 | Y-1 | H | Y-1 | Y-1 | Y-1 |
| 119 | Z-b | Y-1 | Y-1 | Y-1 | H | H | H |
| 120 | Z-b | Y-1 | Y-1 | Y-1 | H | H | Y-1 |

| No. | Z | $R^a$ | $R^b$ | $R^c$ | $R^d$ | $R^e$ | $R^f$ |
|---|---|---|---|---|---|---|---|
| 121 | Z-b | Y-1 | Y-1 | Y-1 | H | Y-1 | H |
| 122 | Z-b | Y-1 | Y-1 | Y-1 | H | Y-1 | Y-1 |
| 123 | Z-b | Y-1 | Y-1 | Y-1 | Y-1 | H | H |
| 124 | Z-b | Y-1 | Y-1 | Y-1 | Y-1 | H | Y-1 |
| 125 | Z-b | Y-1 | Y-1 | Y-1 | Y-1 | Y-1 | H |
| 126 | Z-b | Y-1 | Y-1 | Y-1 | Y-1 | Y-1 | Y-1 |
| 127 | Z-b | H | H | H | H | H | Y-2 |
| 128 | Z-b | H | H | H | H | Y-2 | H |
| 129 | Z-b | H | H | H | H | Y-2 | Y-2 |
| 130 | Z-b | H | H | H | Y-2 | H | H |
| 131 | Z-b | H | H | H | Y-2 | H | Y-2 |
| 132 | Z-b | H | H | H | Y-2 | Y-2 | H |
| 133 | Z-b | H | H | H | Y-2 | Y-2 | Y-2 |
| 134 | Z-b | H | H | Y-2 | H | H | H |
| 135 | Z-b | H | H | Y-2 | H | H | Y-2 |
| 136 | Z-b | H | H | Y-2 | H | Y-2 | H |
| 137 | Z-b | H | H | Y-2 | H | Y-2 | Y-2 |
| 138 | Z-b | H | H | Y-2 | Y-2 | H | H |
| 139 | Z-b | H | H | Y-2 | Y-2 | H | Y-2 |
| 140 | Z-b | H | H | Y-2 | Y-2 | Y-2 | H |
| 141 | Z-b | H | H | Y-2 | Y-2 | Y-2 | Y-2 |
| 142 | Z-b | H | Y-2 | H | H | H | H |
| 143 | Z-b | H | Y-2 | H | H | H | Y-2 |
| 144 | Z-b | H | Y-2 | H | H | Y-2 | H |
| 145 | Z-b | H | Y-2 | H | H | Y-2 | Y-2 |
| 146 | Z-b | H | Y-2 | H | Y-2 | H | H |
| 147 | Z-b | H | Y-2 | H | Y-2 | H | Y-2 |
| 148 | Z-b | H | Y-2 | H | Y-2 | Y-2 | H |
| 149 | Z-b | H | Y-2 | H | Y-2 | Y-2 | Y-2 |
| 150 | Z-b | H | Y-2 | Y-2 | H | H | H |
| 151 | Z-b | H | Y-2 | Y-2 | H | H | Y-2 |
| 152 | Z-b | H | Y-2 | Y-2 | H | Y-2 | H |
| 153 | Z-b | H | Y-2 | Y-2 | H | Y-2 | Y-2 |
| 154 | Z-b | H | Y-2 | Y-2 | Y-2 | H | H |
| 155 | Z-b | H | Y-2 | Y-2 | Y-2 | H | Y-2 |
| 156 | Z-b | H | Y-2 | Y-2 | Y-2 | Y-2 | H |
| 157 | Z-b | H | Y-2 | Y-2 | Y-2 | Y-2 | Y-2 |
| 158 | Z-b | Y-2 | H | H | H | H | H |
| 159 | Z-b | Y-2 | H | H | H | H | Y-2 |
| 160 | Z-b | Y-2 | H | H | H | Y-2 | H |
| 161 | Z-b | Y-2 | H | H | H | Y-2 | Y-2 |
| 162 | Z-b | Y-2 | H | H | Y-2 | H | H |
| 163 | Z-b | Y-2 | H | H | Y-2 | H | Y-2 |
| 164 | Z-b | Y-2 | H | H | Y-2 | Y-2 | H |
| 165 | Z-b | Y-2 | H | H | Y-2 | Y-2 | Y-2 |
| 166 | Z-b | Y-2 | H | Y-2 | H | H | H |
| 167 | Z-b | Y-2 | H | Y-2 | H | H | Y-2 |
| 168 | Z-b | Y-2 | H | Y-2 | H | Y-2 | H |
| 169 | Z-b | Y-2 | H | Y-2 | H | Y-2 | Y-2 |
| 170 | Z-b | Y-2 | H | Y-2 | Y-2 | H | H |
| 171 | Z-b | Y-2 | H | Y-2 | Y-2 | H | Y-2 |
| 172 | Z-b | Y-2 | H | Y-2 | Y-2 | Y-2 | H |
| 173 | Z-b | Y-2 | H | Y-2 | Y-2 | Y-2 | Y-2 |
| 174 | Z-b | Y-2 | Y-2 | H | H | H | H |
| 175 | Z-b | Y-2 | Y-2 | H | H | H | Y-2 |
| 176 | Z-b | Y-2 | Y-2 | H | H | Y-2 | H |
| 177 | Z-b | Y-2 | Y-2 | H | H | Y-2 | Y-2 |
| 178 | Z-b | Y-2 | Y-2 | H | Y-2 | H | H |
| 179 | Z-b | Y-2 | Y-2 | H | Y-2 | H | Y-2 |
| 180 | Z-b | Y-2 | Y-2 | H | Y-2 | Y-2 | H |
| 181 | Z-b | Y-2 | Y-2 | H | Y-2 | Y-2 | Y-2 |
| 182 | Z-b | Y-2 | Y-2 | Y-2 | H | H | H |
| 183 | Z-b | Y-2 | Y-2 | Y-2 | H | H | Y-2 |
| 184 | Z-b | Y-2 | Y-2 | Y-2 | H | Y-2 | H |
| 185 | Z-b | Y-2 | Y-2 | Y-2 | H | Y-2 | Y-2 |
| 186 | Z-b | Y-2 | Y-2 | Y-2 | Y-2 | H | H |
| 187 | Z-b | Y-2 | Y-2 | Y-2 | Y-2 | H | Y-2 |
| 188 | Z-b | Y-2 | Y-2 | Y-2 | Y-2 | Y-2 | H |
| 189 | Z-b | Y-2 | Y-2 | Y-2 | Y-2 | Y-2 | Y-2 |
| 190 | Z-b | H | H | H | H | H | Y-3 |
| 191 | Z-b | H | H | H | H | Y-3 | H |
| 192 | Z-b | H | H | H | H | Y-3 | Y-3 |
| 193 | Z-b | H | H | H | Y-3 | H | H |
| 194 | Z-b | H | H | H | Y-3 | H | Y-3 |
| 195 | Z-b | H | H | H | Y-3 | Y-3 | H |
| 196 | Z-b | H | H | H | Y-3 | Y-3 | Y-3 |
| 197 | Z-b | H | H | Y-3 | H | H | H |
| 198 | Z-b | H | H | Y-3 | H | H | Y-3 |
| 199 | Z-b | H | H | Y-3 | H | Y-3 | H |
| 200 | Z-b | H | H | Y-3 | H | Y-3 | Y-3 |
| 201 | Z-b | H | H | Y-3 | Y-3 | H | H |
| 202 | Z-b | H | H | Y-3 | Y-3 | H | Y-3 |
| 203 | Z-b | H | H | Y-3 | Y-3 | Y-3 | H |
| 204 | Z-b | H | H | Y-3 | Y-3 | Y-3 | Y-3 |
| 205 | Z-b | H | Y-3 | H | H | H | H |
| 206 | Z-b | H | Y-3 | H | H | H | Y-3 |
| 207 | Z-b | H | Y-3 | H | H | Y-3 | H |
| 208 | Z-b | H | Y-3 | H | H | Y-3 | Y-3 |
| 209 | Z-b | H | Y-3 | H | Y-3 | H | H |
| 210 | Z-b | H | Y-3 | H | Y-3 | H | Y-3 |
| 211 | Z-b | H | Y-3 | H | Y-3 | Y-3 | H |
| 212 | Z-b | H | Y-3 | H | Y-3 | Y-3 | Y-3 |
| 213 | Z-b | H | Y-3 | Y-3 | H | H | H |
| 214 | Z-b | H | Y-3 | Y-3 | H | H | Y-3 |
| 215 | Z-b | H | Y-3 | Y-3 | H | Y-3 | H |
| 216 | Z-b | H | Y-3 | Y-3 | H | Y-3 | Y-3 |
| 217 | Z-b | H | Y-3 | Y-3 | Y-3 | H | H |
| 218 | Z-b | H | Y-3 | Y-3 | Y-3 | H | Y-3 |
| 219 | Z-b | H | Y-3 | Y-3 | Y-3 | Y-3 | H |
| 220 | Z-b | H | Y-3 | Y-3 | Y-3 | Y-3 | Y-3 |
| 221 | Z-b | Y-3 | H | H | H | H | H |
| 222 | Z-b | Y-3 | H | H | H | H | Y-3 |
| 223 | Z-b | Y-3 | H | H | H | Y-3 | H |
| 224 | Z-b | Y-3 | H | H | H | Y-3 | Y-3 |
| 225 | Z-b | Y-3 | H | H | Y-3 | H | H |
| 226 | Z-b | Y-3 | H | H | Y-3 | H | Y-3 |
| 227 | Z-b | Y-3 | H | H | Y-3 | Y-3 | H |
| 228 | Z-b | Y-3 | H | H | Y-3 | Y-3 | Y-3 |
| 229 | Z-b | Y-3 | H | Y-3 | H | H | H |
| 230 | Z-b | Y-3 | H | Y-3 | H | H | Y-3 |
| 231 | Z-b | Y-3 | H | Y-3 | H | Y-3 | H |
| 232 | Z-b | Y-3 | H | Y-3 | H | Y-3 | Y-3 |
| 233 | Z-b | Y-3 | H | Y-3 | Y-3 | H | H |
| 234 | Z-b | Y-3 | H | Y-3 | Y-3 | H | Y-3 |
| 235 | Z-b | Y-3 | H | Y-3 | Y-3 | Y-3 | H |
| 236 | Z-b | Y-3 | H | Y-3 | Y-3 | Y-3 | Y-3 |
| 237 | Z-b | Y-3 | Y-3 | H | H | H | H |
| 238 | Z-b | Y-3 | Y-3 | H | H | H | Y-3 |
| 239 | Z-b | Y-3 | Y-3 | H | H | Y-3 | H |
| 240 | Z-b | Y-3 | Y-3 | H | H | Y-3 | Y-3 |
| 241 | Z-b | Y-3 | Y-3 | H | Y-3 | H | H |
| 242 | Z-b | Y-3 | Y-3 | H | Y-3 | H | Y-3 |
| 243 | Z-b | Y-3 | Y-3 | H | Y-3 | Y-3 | H |
| 244 | Z-b | Y-3 | Y-3 | H | Y-3 | Y-3 | Y-3 |
| 245 | Z-b | Y-3 | Y-3 | Y-3 | H | H | H |
| 246 | Z-b | Y-3 | Y-3 | Y-3 | H | H | Y-3 |
| 247 | Z-b | Y-3 | Y-3 | Y-3 | H | Y-3 | H |
| 248 | Z-b | Y-3 | Y-3 | Y-3 | H | Y-3 | Y-3 |
| 249 | Z-b | Y-3 | Y-3 | Y-3 | Y-3 | H | H |
| 250 | Z-b | Y-3 | Y-3 | Y-3 | Y-3 | H | Y-3 |
| 251 | Z-b | Y-3 | Y-3 | Y-3 | Y-3 | Y-3 | H |
| 252 | Z-b | Y-3 | Y-3 | Y-3 | Y-3 | Y-3 | Y-3 |
| 253 | Z-c | H | H | H | H | H | Y-1 |
| 254 | Z-c | H | H | H | H | Y-1 | H |
| 255 | Z-c | H | H | H | H | Y-1 | Y-1 |
| 256 | Z-c | H | H | H | Y-1 | H | H |
| 257 | Z-c | H | H | H | Y-1 | H | Y-1 |
| 258 | Z-c | H | H | H | Y-1 | Y-1 | H |
| 259 | Z-c | H | H | H | Y-1 | Y-1 | Y-1 |
| 260 | Z-c | H | H | Y-1 | H | H | H |
| 261 | Z-c | H | H | Y-1 | H | H | Y-1 |
| 262 | Z-c | H | H | Y-1 | H | Y-1 | H |
| 263 | Z-c | H | H | Y-1 | H | Y-1 | Y-1 |
| 264 | Z-c | H | H | Y-1 | Y-1 | H | H |
| 265 | Z-c | H | H | Y-1 | Y-1 | H | Y-1 |
| 266 | Z-c | H | H | Y-1 | Y-1 | Y-1 | H |
| 267 | Z-c | H | H | Y-1 | Y-1 | Y-1 | Y-1 |
| 268 | Z-c | H | Y-1 | H | H | H | H |
| 269 | Z-c | H | Y-1 | H | H | H | Y-1 |
| 270 | Z-c | H | Y-1 | H | H | Y-1 | H |
| 271 | Z-c | H | Y-1 | H | H | Y-1 | Y-1 |
| 272 | Z-c | H | Y-1 | H | Y-1 | H | H |
| 273 | Z-c | H | Y-1 | H | Y-1 | H | Y-1 |
| 274 | Z-c | H | Y-1 | H | Y-1 | Y-1 | H |

| No. | Z | $R^a$ | $R^b$ | $R^c$ | $R^d$ | $R^e$ | $R^f$ |
| --- | --- | --- | --- | --- | --- | --- | --- |
| 275 | Z-c | H | Y-1 | H | Y-1 | Y-1 | Y-1 |
| 276 | Z-c | H | Y-1 | Y-1 | H | H | H |
| 277 | Z-c | H | Y-1 | Y-1 | H | H | Y-1 |
| 278 | Z-c | H | Y-1 | Y-1 | H | Y-1 | H |
| 279 | Z-c | H | Y-1 | Y-1 | H | Y-1 | Y-1 |
| 280 | Z-c | H | Y-1 | Y-1 | Y-1 | H | H |
| 281 | Z-c | H | Y-1 | Y-1 | Y-1 | H | Y-1 |
| 282 | Z-c | H | Y-1 | Y-1 | Y-1 | Y-1 | H |
| 283 | Z-c | H | Y-1 | Y-1 | Y-1 | Y-1 | Y-1 |
| 284 | Z-c | Y-1 | H | H | H | H | H |
| 285 | Z-c | Y-1 | H | H | H | H | Y-1 |
| 286 | Z-c | Y-1 | H | H | H | Y-1 | H |
| 287 | Z-c | Y-1 | H | H | H | Y-1 | Y-1 |
| 288 | Z-c | Y-1 | H | H | Y-1 | H | H |
| 289 | Z-c | Y-1 | H | H | Y-1 | H | Y-1 |
| 290 | Z-c | Y-1 | H | H | Y-1 | Y-1 | H |
| 291 | Z-c | Y-1 | H | H | Y-1 | Y-1 | Y-1 |
| 292 | Z-c | Y-1 | H | Y-1 | H | H | H |
| 293 | Z-c | Y-1 | H | Y-1 | H | H | Y-1 |
| 294 | Z-c | Y-1 | H | Y-1 | H | Y-1 | H |
| 295 | Z-c | Y-1 | H | Y-1 | H | Y-1 | Y-1 |
| 296 | Z-c | Y-1 | H | Y-1 | Y-1 | H | H |
| 297 | Z-c | Y-1 | H | Y-1 | Y-1 | H | Y-1 |
| 298 | Z-c | Y-1 | H | Y-1 | Y-1 | Y-1 | H |
| 299 | Z-c | Y-1 | H | Y-1 | Y-1 | Y-1 | Y-1 |
| 300 | Z-c | Y-1 | Y-1 | H | H | H | H |
| 301 | Z-c | Y-1 | Y-1 | H | H | H | Y-1 |
| 302 | Z-c | Y-1 | Y-1 | H | H | Y-1 | H |
| 303 | Z-c | Y-1 | Y-1 | H | H | Y-1 | Y-1 |
| 304 | Z-c | Y-1 | Y-1 | H | Y-1 | H | H |
| 305 | Z-c | Y-1 | Y-1 | H | Y-1 | H | Y-1 |
| 306 | Z-c | Y-1 | Y-1 | H | Y-1 | Y-1 | H |
| 307 | Z-c | Y-1 | Y-1 | H | Y-1 | Y-1 | Y-1 |
| 308 | Z-c | Y-1 | Y-1 | Y-1 | H | H | H |
| 309 | Z-c | Y-1 | Y-1 | Y-1 | H | H | Y-1 |
| 310 | Z-c | Y-1 | Y-1 | Y-1 | H | Y-1 | H |
| 311 | Z-c | Y-1 | Y-1 | Y-1 | H | Y-1 | Y-1 |
| 312 | Z-c | Y-1 | Y-1 | Y-1 | Y-1 | H | H |
| 313 | Z-c | Y-1 | Y-1 | Y-1 | Y-1 | H | Y-1 |
| 314 | Z-c | Y-1 | Y-1 | Y-1 | Y-1 | Y-1 | H |
| 315 | Z-c | Y-1 | Y-1 | Y-1 | Y-1 | Y-1 | Y-1 |
| 316 | Z-c | H | H | H | H | H | Y-2 |
| 317 | Z-c | H | H | H | H | Y-2 | H |
| 318 | Z-c | H | H | H | H | Y-2 | Y-2 |
| 319 | Z-c | H | H | H | Y-2 | H | H |
| 320 | Z-c | H | H | H | Y-2 | H | Y-2 |
| 321 | Z-c | H | H | H | Y-2 | Y-2 | H |
| 322 | Z-c | H | H | H | Y-2 | Y-2 | Y-2 |
| 323 | Z-c | H | H | Y-2 | H | H | H |
| 324 | Z-c | H | H | Y-2 | H | H | Y-2 |
| 325 | Z-c | H | H | Y-2 | H | Y-2 | H |
| 326 | Z-c | H | H | Y-2 | H | Y-2 | Y-2 |
| 327 | Z-c | H | H | Y-2 | Y-2 | H | H |
| 328 | Z-c | H | H | Y-2 | Y-2 | H | Y-2 |
| 329 | Z-c | H | H | Y-2 | Y-2 | Y-2 | H |
| 330 | Z-c | H | H | Y-2 | Y-2 | Y-2 | Y-2 |
| 331 | Z-c | H | Y-2 | H | H | H | H |
| 332 | Z-c | H | Y-2 | H | H | H | Y-2 |
| 333 | Z-c | H | Y-2 | H | H | Y-2 | H |
| 334 | Z-c | H | Y-2 | H | H | Y-2 | Y-2 |
| 335 | Z-c | H | Y-2 | H | Y-2 | H | H |
| 336 | Z-c | H | Y-2 | H | Y-2 | H | Y-2 |
| 337 | Z-c | H | Y-2 | H | Y-2 | Y-2 | H |
| 338 | Z-c | H | Y-2 | H | Y-2 | Y-2 | Y-2 |
| 339 | Z-c | H | Y-2 | Y-2 | H | H | H |
| 340 | Z-c | H | Y-2 | Y-2 | H | H | Y-2 |
| 341 | Z-c | H | Y-2 | Y-2 | H | Y-2 | H |
| 342 | Z-c | H | Y-2 | Y-2 | H | Y-2 | Y-2 |
| 343 | Z-c | H | Y-2 | Y-2 | Y-2 | H | H |
| 344 | Z-c | H | Y-2 | Y-2 | Y-2 | H | Y-2 |
| 345 | Z-c | H | Y-2 | Y-2 | Y-2 | Y-2 | H |
| 346 | Z-c | H | Y-2 | Y-2 | Y-2 | Y-2 | Y-2 |
| 347 | Z-c | Y-2 | H | H | H | H | H |
| 348 | Z-c | Y-2 | H | H | H | H | Y-2 |
| 349 | Z-c | Y-2 | H | H | H | Y-2 | H |
| 350 | Z-c | Y-2 | H | H | H | Y-2 | Y-2 |
| 351 | Z-c | Y-2 | H | H | Y-2 | H | H |
| 352 | Z-c | Y-2 | H | H | Y-2 | H | Y-2 |
| 353 | Z-c | Y-2 | H | H | Y-2 | Y-2 | H |
| 354 | Z-c | Y-2 | H | H | Y-2 | Y-2 | Y-2 |
| 355 | Z-c | Y-2 | H | Y-2 | H | H | H |
| 356 | Z-c | Y-2 | H | Y-2 | H | H | Y-2 |
| 357 | Z-c | Y-2 | H | Y-2 | H | Y-2 | H |
| 358 | Z-c | Y-2 | H | Y-2 | H | Y-2 | Y-2 |
| 359 | Z-c | Y-2 | H | Y-2 | Y-2 | H | H |
| 360 | Z-c | Y-2 | H | Y-2 | Y-2 | H | Y-2 |
| 361 | Z-c | Y-2 | H | Y-2 | Y-2 | Y-2 | H |
| 362 | Z-c | Y-2 | H | Y-2 | Y-2 | Y-2 | Y-2 |
| 363 | Z-c | Y-2 | Y-2 | H | H | H | H |
| 364 | Z-c | Y-2 | Y-2 | H | H | H | Y-2 |
| 365 | Z-c | Y-2 | Y-2 | H | H | Y-2 | H |
| 366 | Z-c | Y-2 | Y-2 | H | H | Y-2 | Y-2 |
| 367 | Z-c | Y-2 | Y-2 | H | Y-2 | H | H |
| 368 | Z-c | Y-2 | Y-2 | H | Y-2 | H | Y-2 |
| 369 | Z-c | Y-2 | Y-2 | H | Y-2 | Y-2 | H |
| 370 | Z-c | Y-2 | Y-2 | H | Y-2 | Y-2 | Y-2 |
| 371 | Z-c | Y-2 | Y-2 | Y-2 | H | H | H |
| 372 | Z-c | Y-2 | Y-2 | Y-2 | H | H | Y-2 |
| 373 | Z-c | Y-2 | Y-2 | Y-2 | H | Y-2 | H |
| 374 | Z-c | Y-2 | Y-2 | Y-2 | H | Y-2 | Y-2 |
| 375 | Z-c | Y-2 | Y-2 | Y-2 | Y-2 | H | H |
| 376 | Z-c | Y-2 | Y-2 | Y-2 | Y-2 | H | Y-2 |
| 377 | Z-c | Y-2 | Y-2 | Y-2 | Y-2 | Y-2 | H |
| 378 | Z-c | Y-2 | Y-2 | Y-2 | Y-2 | Y-2 | Y-2 |
| 379 | Z-c | H | H | H | H | Y-3 | H |
| 380 | Z-c | H | H | H | H | Y-3 | Y-3 |
| 381 | Z-c | H | H | H | H | Y-3 | Y-3 |
| 382 | Z-c | H | H | H | Y-3 | H | H |
| 383 | Z-c | H | H | H | Y-3 | H | H |
| 384 | Z-c | H | H | H | Y-3 | Y-3 | H |
| 385 | Z-c | H | H | H | Y-3 | Y-3 | Y-3 |
| 386 | Z-c | H | H | Y-3 | H | H | H |
| 387 | Z-c | H | H | Y-3 | H | H | Y-3 |
| 388 | Z-c | H | H | Y-3 | H | Y-3 | H |
| 389 | Z-c | H | H | Y-3 | H | Y-3 | Y-3 |
| 390 | Z-c | H | H | Y-3 | Y-3 | H | H |
| 391 | Z-c | H | H | Y-3 | Y-3 | H | Y-3 |
| 392 | Z-c | H | H | Y-3 | Y-3 | Y-3 | H |
| 393 | Z-c | H | H | Y-3 | Y-3 | Y-3 | Y-3 |
| 394 | Z-c | H | Y-3 | H | H | H | H |
| 395 | Z-c | H | Y-3 | H | H | H | Y-3 |
| 396 | Z-c | H | Y-3 | H | H | Y-3 | H |
| 397 | Z-c | H | Y-3 | H | H | Y-3 | Y-3 |
| 398 | Z-c | H | Y-3 | H | Y-3 | H | H |
| 399 | Z-c | H | Y-3 | H | Y-3 | H | Y-3 |
| 400 | Z-c | H | Y-3 | H | Y-3 | Y-3 | H |
| 401 | Z-c | H | Y-3 | H | Y-3 | Y-3 | Y-3 |
| 402 | Z-c | H | Y-3 | Y-3 | H | H | H |
| 403 | Z-c | H | Y-3 | Y-3 | H | H | Y-3 |
| 404 | Z-c | H | Y-3 | Y-3 | H | Y-3 | H |
| 405 | Z-c | H | Y-3 | Y-3 | H | Y-3 | Y-3 |
| 406 | Z-c | H | Y-3 | Y-3 | Y-3 | H | H |
| 407 | Z-c | H | Y-3 | Y-3 | Y-3 | H | Y-3 |
| 408 | Z-c | H | Y-3 | Y-3 | Y-3 | Y-3 | H |
| 409 | Z-c | H | Y-3 | Y-3 | Y-3 | Y-3 | Y-3 |
| 410 | Z-c | Y-3 | H | H | H | H | H |
| 411 | Z-c | Y-3 | H | H | H | H | Y-3 |
| 412 | Z-c | Y-3 | H | H | H | Y-3 | H |
| 413 | Z-c | Y-3 | H | H | H | Y-3 | Y-3 |
| 414 | Z-c | Y-3 | H | H | Y-3 | H | H |
| 415 | Z-c | Y-3 | H | H | Y-3 | H | Y-3 |
| 416 | Z-c | Y-3 | H | H | Y-3 | Y-3 | H |
| 417 | Z-c | Y-3 | H | H | Y-3 | Y-3 | Y-3 |
| 418 | Z-c | Y-3 | H | Y-3 | H | H | H |
| 419 | Z-c | Y-3 | H | Y-3 | H | H | Y-3 |
| 420 | Z-c | Y-3 | H | Y-3 | H | Y-3 | H |
| 421 | Z-c | Y-3 | H | Y-3 | H | Y-3 | Y-3 |
| 422 | Z-c | Y-3 | H | Y-3 | Y-3 | H | H |
| 423 | Z-c | Y-3 | H | Y-3 | Y-3 | H | Y-3 |
| 424 | Z-c | Y-3 | H | Y-3 | Y-3 | Y-3 | H |
| 425 | Z-c | Y-3 | H | Y-3 | Y-3 | Y-3 | Y-3 |
| 426 | Z-c | Y-3 | Y-3 | H | H | H | H |
| 427 | Z-c | Y-3 | Y-3 | H | H | H | Y-3 |
| 428 | Z-c | Y-3 | Y-3 | H | H | Y-3 | H |

| No. | Z | $R^a$ | $R^b$ | $R^c$ | $R^d$ | $R^e$ | $R^f$ |
|---|---|---|---|---|---|---|---|
| 429 | Z-c | Y-3 | Y-3 | H | H | Y-3 | Y-3 |
| 430 | Z-c | Y-3 | Y-3 | H | Y-3 | H | H |
| 431 | Z-c | Y-3 | Y-3 | H | Y-3 | H | Y-3 |
| 432 | Z-c | Y-3 | Y-3 | H | Y-3 | Y-3 | H |
| 433 | Z-c | Y-3 | Y-3 | H | Y-3 | Y-3 | Y-3 |
| 434 | Z-c | Y-3 | Y-3 | Y-3 | H | H | H |
| 435 | Z-c | Y-3 | Y-3 | Y-3 | H | H | Y-3 |
| 436 | Z-c | Y-3 | Y-3 | Y-3 | H | Y-3 | H |
| 437 | Z-c | Y-3 | Y-3 | Y-3 | H | Y-3 | Y-3 |
| 438 | Z-c | Y-3 | Y-3 | Y-3 | Y-3 | H | H |
| 439 | Z-c | Y-3 | Y-3 | Y-3 | Y-3 | H | Y-3 |
| 440 | Z-c | Y-3 | Y-3 | Y-3 | Y-3 | Y-3 | H |
| 441 | Z-c | Y-3 | Y-3 | Y-3 | Y-3 | Y-3 | Y-3 |
| 442 | Z-d | H | H | H | H | H | Y-1 |
| 443 | Z-d | H | H | H | H | Y-1 | H |
| 444 | Z-d | H | H | H | H | Y-1 | Y-1 |
| 445 | Z-d | H | H | H | Y-1 | H | H |
| 446 | Z-d | H | H | H | Y-1 | H | Y-1 |
| 447 | Z-d | H | H | H | Y-1 | Y-1 | H |
| 448 | Z-d | H | H | H | Y-1 | Y-1 | Y-1 |
| 449 | Z-d | H | H | Y-1 | H | H | H |
| 450 | Z-d | H | H | Y-1 | H | H | Y-1 |
| 451 | Z-d | H | H | Y-1 | H | Y-1 | H |
| 452 | Z-d | H | H | Y-1 | H | Y-1 | Y-1 |
| 453 | Z-d | H | H | Y-1 | Y-1 | H | H |
| 454 | Z-d | H | H | Y-1 | Y-1 | H | Y-1 |
| 455 | Z-d | H | H | Y-1 | Y-1 | Y-1 | H |
| 456 | Z-d | H | H | Y-1 | Y-1 | Y-1 | Y-1 |
| 457 | Z-d | H | Y-1 | H | H | H | H |
| 458 | Z-d | H | Y-1 | H | H | H | Y-1 |
| 459 | Z-d | H | Y-1 | H | H | Y-1 | H |
| 460 | Z-d | H | Y-1 | H | H | Y-1 | Y-1 |
| 461 | Z-d | H | Y-1 | H | Y-1 | H | H |
| 462 | Z-d | H | Y-1 | H | Y-1 | H | Y-1 |
| 463 | Z-d | H | Y-1 | H | Y-1 | Y-1 | H |
| 464 | Z-d | H | Y-1 | H | Y-1 | Y-1 | Y-1 |
| 465 | Z-d | H | Y-1 | Y-1 | H | H | H |
| 466 | Z-d | H | Y-1 | Y-1 | H | H | Y-1 |
| 467 | Z-d | H | Y-1 | Y-1 | H | Y-1 | H |
| 468 | Z-d | H | Y-1 | Y-1 | H | Y-1 | Y-1 |
| 469 | Z-d | H | Y-1 | Y-1 | Y-1 | H | H |
| 470 | Z-d | H | Y-1 | Y-1 | Y-1 | H | Y-1 |
| 471 | Z-d | H | Y-1 | Y-1 | Y-1 | Y-1 | H |
| 472 | Z-d | H | Y-1 | Y-1 | Y-1 | Y-1 | Y-1 |
| 473 | Z-d | Y-1 | H | H | H | H | H |
| 474 | Z-d | Y-1 | H | H | H | H | Y-1 |
| 475 | Z-d | Y-1 | H | H | H | Y-1 | H |
| 476 | Z-d | Y-1 | H | H | H | Y-1 | Y-1 |
| 477 | Z-d | Y-1 | H | H | Y-1 | H | H |
| 478 | Z-d | Y-1 | H | H | Y-1 | H | Y-1 |
| 479 | Z-d | Y-1 | H | H | Y-1 | Y-1 | H |
| 480 | Z-d | Y-1 | H | H | Y-1 | Y-1 | Y-1 |
| 481 | Z-d | Y-1 | H | Y-1 | H | H | H |
| 482 | Z-d | Y-1 | H | Y-1 | H | H | Y-1 |
| 483 | Z-d | Y-1 | H | Y-1 | H | Y-1 | H |
| 484 | Z-d | Y-1 | H | Y-1 | H | Y-1 | Y-1 |
| 485 | Z-d | Y-1 | H | Y-1 | Y-1 | H | H |
| 486 | Z-d | Y-1 | H | Y-1 | Y-1 | H | Y-1 |
| 487 | Z-d | Y-1 | H | Y-1 | Y-1 | Y-1 | H |
| 488 | Z-d | Y-1 | H | Y-1 | Y-1 | Y-1 | Y-1 |
| 489 | Z-d | Y-1 | Y-1 | H | H | H | H |
| 490 | Z-d | Y-1 | Y-1 | H | H | H | Y-1 |
| 491 | Z-d | Y-1 | Y-1 | H | H | Y-1 | H |
| 492 | Z-d | Y-1 | Y-1 | H | H | Y-1 | Y-1 |
| 493 | Z-d | Y-1 | Y-1 | H | Y-1 | H | H |
| 494 | Z-d | Y-1 | Y-1 | H | Y-1 | H | Y-1 |
| 495 | Z-d | Y-1 | Y-1 | H | Y-1 | Y-1 | H |
| 496 | Z-d | Y-1 | Y-1 | H | Y-1 | Y-1 | Y-1 |
| 497 | Z-d | Y-1 | Y-1 | Y-1 | H | H | H |
| 498 | Z-d | Y-1 | Y-1 | Y-1 | H | H | Y-1 |
| 499 | Z-d | Y-1 | Y-1 | Y-1 | H | Y-1 | H |
| 500 | Z-d | Y-1 | Y-1 | Y-1 | H | Y-1 | Y-1 |
| 501 | Z-d | Y-1 | Y-1 | Y-1 | Y-1 | H | H |
| 502 | Z-d | Y-1 | Y-1 | Y-1 | Y-1 | H | Y-1 |
| 503 | Z-d | Y-1 | Y-1 | Y-1 | Y-1 | Y-1 | H |
| 504 | Z-d | Y-1 | Y-1 | Y-1 | Y-1 | Y-1 | Y-1 |
| 505 | Z-d | H | H | H | H | H | Y-2 |
| 506 | Z-d | H | H | H | H | Y-2 | H |
| 507 | Z-d | H | H | H | H | Y-2 | Y-2 |
| 508 | Z-d | H | H | H | Y-2 | H | H |
| 509 | Z-d | H | H | H | Y-2 | H | Y-2 |
| 510 | Z-d | H | H | H | Y-2 | Y-2 | H |
| 511 | Z-d | H | H | H | Y-2 | Y-2 | Y-2 |
| 512 | Z-d | H | H | Y-2 | H | H | H |
| 513 | Z-d | H | H | Y-2 | H | H | Y-2 |
| 514 | Z-d | H | H | Y-2 | H | Y-2 | H |
| 515 | Z-d | H | H | Y-2 | H | Y-2 | Y-2 |
| 516 | Z-d | H | H | Y-2 | Y-2 | H | H |
| 517 | Z-d | H | H | Y-2 | Y-2 | H | Y-2 |
| 518 | Z-d | H | H | Y-2 | Y-2 | Y-2 | H |
| 519 | Z-d | H | H | Y-2 | Y-2 | Y-2 | Y-2 |
| 520 | Z-d | H | Y-2 | H | H | H | H |
| 521 | Z-d | H | Y-2 | H | H | H | Y-2 |
| 522 | Z-d | H | Y-2 | H | H | Y-2 | H |
| 523 | Z-d | H | Y-2 | H | H | Y-2 | Y-2 |
| 524 | Z-d | H | Y-2 | H | Y-2 | H | H |
| 525 | Z-d | H | Y-2 | H | Y-2 | H | Y-2 |
| 526 | Z-d | H | Y-2 | H | Y-2 | Y-2 | H |
| 527 | Z-d | H | Y-2 | H | Y-2 | Y-2 | Y-2 |
| 528 | Z-d | H | Y-2 | Y-2 | H | H | H |
| 529 | Z-d | H | Y-2 | Y-2 | H | H | Y-2 |
| 530 | Z-d | H | Y-2 | Y-2 | H | Y-2 | H |
| 531 | Z-d | H | Y-2 | Y-2 | H | Y-2 | Y-2 |
| 532 | Z-d | H | Y-2 | Y-2 | Y-2 | H | H |
| 533 | Z-d | H | Y-2 | Y-2 | Y-2 | H | Y-2 |
| 534 | Z-d | H | Y-2 | Y-2 | Y-2 | Y-2 | H |
| 535 | Z-d | H | Y-2 | Y-2 | Y-2 | Y-2 | Y-2 |
| 536 | Z-d | Y-2 | H | H | H | H | H |
| 537 | Z-d | Y-2 | H | H | H | H | Y-2 |
| 538 | Z-d | Y-2 | H | H | H | Y-2 | H |
| 539 | Z-d | Y-2 | H | H | H | Y-2 | Y-2 |
| 540 | Z-d | Y-2 | H | H | Y-2 | H | H |
| 541 | Z-d | Y-2 | H | H | Y-2 | H | Y-2 |
| 542 | Z-d | Y-2 | H | H | Y-2 | Y-2 | H |
| 543 | Z-d | Y-2 | H | H | Y-2 | Y-2 | Y-2 |
| 544 | Z-d | Y-2 | H | Y-2 | H | H | H |
| 545 | Z-d | Y-2 | H | Y-2 | H | H | Y-2 |
| 546 | Z-d | Y-2 | H | Y-2 | H | Y-2 | H |
| 547 | Z-d | Y-2 | H | Y-2 | H | Y-2 | Y-2 |
| 548 | Z-d | Y-2 | H | Y-2 | Y-2 | H | H |
| 549 | Z-d | Y-2 | H | Y-2 | Y-2 | H | Y-2 |
| 550 | Z-d | Y-2 | H | Y-2 | Y-2 | Y-2 | H |
| 551 | Z-d | Y-2 | H | Y-2 | Y-2 | Y-2 | Y-2 |
| 552 | Z-d | Y-2 | Y-2 | H | H | H | H |
| 553 | Z-d | Y-2 | Y-2 | H | H | H | Y-2 |
| 554 | Z-d | Y-2 | Y-2 | H | H | Y-2 | H |
| 555 | Z-d | Y-2 | Y-2 | H | H | Y-2 | Y-2 |
| 556 | Z-d | Y-2 | Y-2 | H | Y-2 | H | H |
| 557 | Z-d | Y-2 | Y-2 | H | Y-2 | H | Y-2 |
| 558 | Z-d | Y-2 | Y-2 | H | Y-2 | Y-2 | H |
| 559 | Z-d | Y-2 | Y-2 | H | Y-2 | Y-2 | Y-2 |
| 560 | Z-d | Y-2 | Y-2 | Y-2 | H | H | H |
| 561 | Z-d | Y-2 | Y-2 | Y-2 | H | H | Y-2 |
| 562 | Z-d | Y-2 | Y-2 | Y-2 | H | Y-2 | H |
| 563 | Z-d | Y-2 | Y-2 | Y-2 | H | Y-2 | Y-2 |
| 564 | Z-d | Y-2 | Y-2 | Y-2 | Y-2 | H | H |
| 565 | Z-d | Y-2 | Y-2 | Y-2 | Y-2 | H | Y-2 |
| 566 | Z-d | Y-2 | Y-2 | Y-2 | Y-2 | Y-2 | H |
| 567 | Z-d | Y-2 | Y-2 | Y-2 | Y-2 | Y-2 | Y-2 |
| 568 | Z-d | H | H | H | H | H | Y-3 |
| 569 | Z-d | H | H | H | H | Y-3 | H |
| 570 | Z-d | H | H | H | H | Y-3 | Y-3 |
| 571 | Z-d | H | H | H | Y-3 | H | H |
| 572 | Z-d | H | H | H | Y-3 | H | Y-3 |
| 573 | Z-d | H | H | H | Y-3 | Y-3 | H |
| 574 | Z-d | H | H | H | Y-3 | Y-3 | Y-3 |
| 575 | Z-d | H | H | Y-3 | H | H | H |
| 576 | Z-d | H | H | Y-3 | H | H | Y-3 |
| 577 | Z-d | H | H | Y-3 | H | Y-3 | H |
| 578 | Z-d | H | H | Y-3 | H | Y-3 | Y-3 |
| 579 | Z-d | H | H | Y-3 | Y-3 | H | H |
| 580 | Z-d | H | H | Y-3 | Y-3 | H | Y-3 |
| 581 | Z-d | H | H | Y-3 | Y-3 | Y-3 | H |
| 582 | Z-d | H | H | Y-3 | Y-3 | Y-3 | Y-3 |

| No. | Z | $R^a$ | $R^b$ | $R^c$ | $R^d$ | $R^e$ | $R^f$ |
|---|---|---|---|---|---|---|---|
| 583 | Z-d | H | Y-3 | H | H | H | H |
| 584 | Z-d | H | Y-3 | H | H | H | Y-3 |
| 585 | Z-d | H | Y-3 | H | H | Y-3 | H |
| 586 | Z-d | H | Y-3 | H | H | Y-3 | Y-3 |
| 587 | Z-d | H | Y-3 | H | Y-3 | H | H |
| 588 | Z-d | H | Y-3 | H | Y-3 | H | Y-3 |
| 589 | Z-d | H | Y-3 | H | Y-3 | Y-3 | H |
| 590 | Z-d | H | Y-3 | H | Y-3 | Y-3 | Y-3 |
| 591 | Z-d | H | Y-3 | Y-3 | H | H | H |
| 592 | Z-d | H | Y-3 | Y-3 | H | H | Y-3 |
| 593 | Z-d | H | Y-3 | Y-3 | H | Y-3 | H |
| 594 | Z-d | H | Y-3 | Y-3 | H | Y-3 | Y-3 |
| 595 | Z-d | H | Y-3 | Y-3 | Y-3 | H | H |
| 596 | Z-d | H | Y-3 | Y-3 | Y-3 | H | Y-3 |
| 597 | Z-d | H | Y-3 | Y-3 | Y-3 | Y-3 | H |
| 598 | Z-d | H | Y-3 | Y-3 | Y-3 | Y-3 | Y-3 |
| 599 | Z-d | Y-3 | H | H | H | H | H |
| 600 | Z-d | Y-3 | H | H | H | H | Y-3 |
| 601 | Z-d | Y-3 | H | H | H | Y-3 | H |
| 602 | Z-d | Y-3 | H | H | H | Y-3 | Y-3 |
| 603 | Z-d | Y-3 | H | H | Y-3 | H | H |
| 604 | Z-d | Y-3 | H | H | Y-3 | H | Y-3 |
| 605 | Z-d | Y-3 | H | H | Y-3 | Y-3 | H |
| 606 | Z-d | Y-3 | H | H | Y-3 | Y-3 | Y-3 |
| 607 | Z-d | Y-3 | H | Y-3 | H | H | H |
| 608 | Z-d | Y-3 | H | Y-3 | H | H | Y-3 |
| 609 | Z-d | Y-3 | H | Y-3 | H | Y-3 | H |
| 610 | Z-d | Y-3 | H | Y-3 | H | Y-3 | Y-3 |
| 611 | Z-d | Y-3 | H | Y-3 | Y-3 | H | H |
| 612 | Z-d | Y-3 | H | Y-3 | Y-3 | H | Y-3 |
| 613 | Z-d | Y-3 | H | Y-3 | Y-3 | Y-3 | H |
| 614 | Z-d | Y-3 | H | Y-3 | Y-3 | Y-3 | Y-3 |
| 615 | Z-d | Y-3 | Y-3 | H | H | H | H |
| 616 | Z-d | Y-3 | Y-3 | H | H | H | Y-3 |
| 617 | Z-d | Y-3 | Y-3 | H | H | Y-3 | H |
| 618 | Z-d | Y-3 | Y-3 | H | H | Y-3 | Y-3 |
| 619 | Z-d | Y-3 | Y-3 | H | Y-3 | H | H |
| 620 | Z-d | Y-3 | Y-3 | H | Y-3 | H | Y-3 |
| 621 | Z-d | Y-3 | Y-3 | H | Y-3 | Y-3 | H |
| 622 | Z-d | Y-3 | Y-3 | H | Y-3 | Y-3 | Y-3 |
| 623 | Z-d | Y-3 | Y-3 | Y-3 | H | H | H |
| 624 | Z-d | Y-3 | Y-3 | Y-3 | H | H | Y-3 |
| 625 | Z-d | Y-3 | Y-3 | Y-3 | H | Y-3 | H |
| 626 | Z-d | Y-3 | Y-3 | Y-3 | H | Y-3 | Y-3 |
| 627 | Z-d | Y-3 | Y-3 | Y-3 | Y-3 | H | H |
| 628 | Z-d | Y-3 | Y-3 | Y-3 | Y-3 | H | Y-3 |
| 629 | Z-d | Y-3 | Y-3 | Y-3 | Y-3 | Y-3 | H |
| 630 | Z-d | Y-3 | Y-3 | Y-3 | Y-3 | Y-3 | Y-3 |
| 631 | Z-e | H | H | Y-1 | — | — | — |
| 632 | Z-e | H | Y-1 | H | — | — | — |
| 633 | Z-e | H | Y-1 | Y-1 | — | — | — |
| 634 | Z-e | Y-1 | H | H | — | — | — |
| 635 | Z-e | Y-1 | H | Y-1 | — | — | — |
| 636 | Z-e | Y-1 | Y-1 | H | — | — | — |
| 637 | Z-e | Y-1 | Y-1 | Y-1 | — | — | — |
| 638 | Z-e | H | H | Y-2 | — | — | — |
| 639 | Z-e | H | Y-2 | H | — | — | — |
| 640 | Z-e | H | Y-2 | Y-2 | — | — | — |
| 641 | Z-e | Y-2 | H | H | — | — | — |
| 642 | Z-e | Y-2 | H | Y-2 | — | — | — |
| 643 | Z-e | Y-2 | Y-2 | H | — | — | — |
| 644 | Z-e | Y-2 | Y-2 | Y-2 | — | — | — |
| 645 | Z-e | H | H | Y-3 | — | — | — |
| 646 | Z-e | H | Y-3 | H | — | — | — |
| 647 | Z-e | H | Y-3 | Y-3 | — | — | — |
| 648 | Z-e | Y-3 | H | H | — | — | — |
| 649 | Z-e | Y-3 | H | Y-3 | — | — | — |
| 650 | Z-e | Y-3 | Y-3 | H | — | — | — |
| 651 | Z-e | Y-3 | Y-3 | Y-3 | — | — | — |
| 652 | Z-f | H | Y-1 | — | — | — | — |
| 653 | Z-f | Y-1 | H | — | — | — | — |
| 654 | Z-f | Y-1 | Y-1 | — | — | — | — |
| 655 | Z-f | H | Y-2 | — | — | — | — |
| 656 | Z-f | Y-2 | H | — | — | — | — |
| 657 | Z-f | Y-2 | Y-2 | — | — | — | — |
| 658 | Z-f | H | Y-3 | — | — | — | — |
| 659 | Z-f | Y-3 | H | — | — | — | — |
| 660 | Z-f | Y-3 | Y-3 | — | — | — | — |
| 661 | Z-g | H | H | Y-1 | — | — | — |
| 662 | Z-g | H | Y-1 | H | — | — | — |
| 663 | Z-g | H | Y-1 | Y-1 | — | — | — |
| 664 | Z-g | Y-1 | H | H | — | — | — |
| 665 | Z-g | Y-1 | H | Y-1 | — | — | — |
| 666 | Z-g | Y-1 | Y-1 | H | — | — | — |
| 667 | Z-g | Y-1 | Y-1 | Y-1 | — | — | — |
| 668 | Z-g | H | H | Y-2 | — | — | — |
| 669 | Z-g | H | Y-2 | H | — | — | — |
| 670 | Z-g | H | Y-2 | Y-2 | — | — | — |
| 671 | Z-g | Y-2 | H | H | — | — | — |
| 672 | Z-g | Y-2 | H | Y-2 | — | — | — |
| 673 | Z-g | Y-2 | Y-2 | H | — | — | — |
| 674 | Z-g | Y-2 | Y-2 | Y-2 | — | — | — |
| 675 | Z-g | H | H | Y-3 | — | — | — |
| 676 | Z-g | H | Y-3 | H | — | — | — |
| 677 | Z-g | H | Y-3 | Y-3 | — | — | — |
| 678 | Z-g | Y-3 | H | H | — | — | — |
| 679 | Z-g | Y-3 | H | Y-3 | — | — | — |
| 680 | Z-g | Y-3 | Y-3 | H | — | — | — |
| 681 | Z-g | Y-3 | Y-3 | Y-3 | — | — | — |
| 682 | Z-h | H | H | H | H | H | Y-1 |
| 683 | Z-h | H | H | H | H | Y-1 | H |
| 684 | Z-h | H | H | H | H | Y-1 | Y-1 |
| 685 | Z-h | H | H | H | Y-1 | H | H |
| 686 | Z-h | H | H | H | Y-1 | H | Y-1 |
| 687 | Z-h | H | H | H | Y-1 | Y-1 | H |
| 688 | Z-h | H | H | H | Y-1 | Y-1 | Y-1 |
| 689 | Z-h | H | H | Y-1 | H | H | H |
| 690 | Z-h | H | H | Y-1 | H | H | Y-1 |
| 691 | Z-h | H | H | Y-1 | H | Y-1 | H |
| 692 | Z-h | H | H | Y-1 | H | Y-1 | Y-1 |
| 693 | Z-h | H | H | Y-1 | Y-1 | H | H |
| 694 | Z-h | H | H | Y-1 | Y-1 | H | Y-1 |
| 695 | Z-h | H | H | Y-1 | Y-1 | Y-1 | H |
| 696 | Z-h | H | H | Y-1 | Y-1 | Y-1 | Y-1 |
| 697 | Z-h | H | Y-1 | H | H | H | H |
| 698 | Z-h | H | Y-1 | H | H | H | Y-1 |
| 699 | Z-h | H | Y-1 | H | H | Y-1 | H |
| 700 | Z-h | H | Y-1 | H | H | Y-1 | Y-1 |
| 701 | Z-h | H | Y-1 | H | Y-1 | H | H |
| 702 | Z-h | H | Y-1 | H | Y-1 | H | Y-1 |
| 703 | Z-h | H | Y-1 | H | Y-1 | Y-1 | H |
| 704 | Z-h | H | Y-1 | H | Y-1 | Y-1 | Y-1 |
| 705 | Z-h | H | Y-1 | Y-1 | H | H | H |
| 706 | Z-h | H | Y-1 | Y-1 | H | H | Y-1 |
| 707 | Z-h | H | Y-1 | Y-1 | H | Y-1 | H |
| 708 | Z-h | H | Y-1 | Y-1 | H | Y-1 | Y-1 |
| 709 | Z-h | H | Y-1 | Y-1 | Y-1 | H | H |
| 710 | Z-h | H | Y-1 | Y-1 | Y-1 | H | Y-1 |
| 711 | Z-h | H | Y-1 | Y-1 | Y-1 | Y-1 | H |
| 712 | Z-h | H | Y-1 | Y-1 | Y-1 | Y-1 | Y-1 |
| 713 | Z-h | Y-1 | H | H | H | H | H |
| 714 | Z-h | Y-1 | H | H | H | H | Y-1 |
| 715 | Z-h | Y-1 | H | H | H | Y-1 | H |
| 716 | Z-h | Y-1 | H | H | H | Y-1 | Y-1 |
| 717 | Z-h | Y-1 | H | H | Y-1 | H | H |
| 718 | Z-h | Y-1 | H | H | Y-1 | H | Y-1 |
| 719 | Z-h | Y-1 | H | H | Y-1 | Y-1 | H |
| 720 | Z-h | Y-1 | H | H | Y-1 | Y-1 | Y-1 |
| 721 | Z-h | Y-1 | H | Y-1 | H | H | H |
| 722 | Z-h | Y-1 | H | Y-1 | H | H | Y-1 |
| 723 | Z-h | Y-1 | H | Y-1 | H | Y-1 | H |
| 724 | Z-h | Y-1 | H | Y-1 | H | Y-1 | Y-1 |
| 725 | Z-h | Y-1 | H | Y-1 | Y-1 | H | H |
| 726 | Z-h | Y-1 | H | Y-1 | Y-1 | H | Y-1 |
| 727 | Z-h | Y-1 | H | Y-1 | Y-1 | Y-1 | H |
| 728 | Z-h | Y-1 | H | Y-1 | Y-1 | Y-1 | Y-1 |
| 729 | Z-h | Y-1 | Y-1 | H | H | H | H |
| 730 | Z-h | Y-1 | Y-1 | H | H | H | Y-1 |
| 731 | Z-h | Y-1 | Y-1 | H | H | Y-1 | H |
| 732 | Z-h | Y-1 | Y-1 | H | H | Y-1 | Y-1 |
| 733 | Z-h | Y-1 | Y-1 | H | Y-1 | H | H |
| 734 | Z-h | Y-1 | Y-1 | H | Y-1 | H | Y-1 |
| 735 | Z-h | Y-1 | Y-1 | H | Y-1 | Y-1 | H |
| 736 | Z-h | Y-1 | Y-1 | H | Y-1 | Y-1 | Y-1 |

-continued

| No. | Z | $R^a$ | $R^b$ | $R^c$ | $R^d$ | $R^e$ | $R^f$ |
|---|---|---|---|---|---|---|---|
| 737 | Z-h | Y-1 | Y-1 | Y-1 | H | H | H |
| 738 | Z-h | Y-1 | Y-1 | Y-1 | H | H | Y-1 |
| 739 | Z-h | Y-1 | Y-1 | Y-1 | H | Y-1 | H |
| 740 | Z-h | Y-1 | Y-1 | Y-1 | H | Y-1 | Y-1 |
| 741 | Z-h | Y-1 | Y-1 | Y-1 | Y-1 | H | H |
| 742 | Z-h | Y-1 | Y-1 | Y-1 | Y-1 | H | Y-1 |
| 743 | Z-h | Y-1 | Y-1 | Y-1 | Y-1 | Y-1 | H |
| 744 | Z-h | Y-1 | Y-1 | Y-1 | Y-1 | Y-1 | Y-1 |
| 745 | Z-h | H | H | H | H | H | Y-2 |
| 746 | Z-h | H | H | H | H | Y-2 | H |
| 747 | Z-h | H | H | H | H | Y-2 | Y-2 |
| 748 | Z-h | H | H | H | Y-2 | H | H |
| 749 | Z-h | H | H | H | Y-2 | H | Y-2 |
| 750 | Z-h | H | H | H | Y-2 | Y-2 | H |
| 751 | Z-h | H | H | H | Y-2 | Y-2 | Y-1 |
| 752 | Z-h | H | H | Y-2 | H | H | H |
| 753 | Z-h | H | H | Y-2 | H | H | Y-2 |
| 754 | Z-h | H | H | Y-2 | H | Y-2 | H |
| 755 | Z-h | H | H | Y-2 | H | Y-2 | Y-2 |
| 756 | Z-h | H | H | Y-2 | Y-2 | H | H |
| 757 | Z-h | H | H | Y-2 | Y-2 | H | Y-2 |
| 758 | Z-h | H | H | Y-2 | Y-2 | Y-2 | H |
| 759 | Z-h | H | H | Y-2 | Y-2 | Y-2 | Y-2 |
| 760 | Z-h | H | Y-2 | H | H | H | H |
| 761 | Z-h | H | Y-2 | H | H | H | Y-2 |
| 762 | Z-h | H | Y-2 | H | H | Y-2 | H |
| 763 | Z-h | H | Y-2 | H | H | Y-2 | Y-2 |
| 764 | Z-h | H | Y-2 | H | Y-2 | H | H |
| 765 | Z-h | H | Y-2 | H | Y-2 | H | Y-2 |
| 766 | Z-h | H | Y-2 | H | Y-2 | Y-2 | H |
| 767 | Z-h | H | Y-2 | H | Y-2 | Y-2 | Y-2 |
| 768 | Z-h | H | Y-2 | Y-2 | H | H | H |
| 769 | Z-h | H | Y-2 | Y-2 | H | H | Y-2 |
| 770 | Z-h | H | Y-2 | Y-2 | H | Y-2 | H |
| 771 | Z-h | H | Y-2 | Y-2 | H | Y-2 | Y-2 |
| 772 | Z-h | H | Y-2 | Y-2 | Y-2 | H | H |
| 773 | Z-h | H | Y-2 | Y-2 | Y-2 | H | Y-2 |
| 774 | Z-h | H | Y-2 | Y-2 | Y-2 | Y-2 | H |
| 775 | Z-h | H | Y-2 | Y-2 | Y-2 | Y-2 | Y-2 |
| 776 | Z-h | Y-2 | H | H | H | H | H |
| 777 | Z-h | Y-2 | H | H | H | H | Y-2 |
| 778 | Z-h | Y-2 | H | H | H | Y-2 | H |
| 779 | Z-h | Y-2 | H | H | H | Y-2 | Y-2 |
| 780 | Z-h | Y-2 | H | H | Y-2 | H | H |
| 781 | Z-h | Y-2 | H | H | Y-2 | H | Y-2 |
| 782 | Z-h | Y-2 | H | H | Y-2 | Y-2 | H |
| 783 | Z-h | Y-2 | H | H | Y-2 | Y-2 | Y-2 |
| 784 | Z-h | Y-2 | H | Y-2 | H | H | H |
| 785 | Z-h | Y-2 | H | Y-2 | H | H | Y-2 |
| 786 | Z-h | Y-2 | H | Y-2 | H | Y-2 | H |
| 787 | Z-h | Y-2 | H | Y-2 | H | Y-2 | Y-2 |
| 788 | Z-h | Y-2 | H | Y-2 | Y-2 | H | H |
| 789 | Z-h | Y-2 | H | Y-2 | Y-2 | H | Y-2 |
| 790 | Z-h | Y-2 | H | Y-2 | Y-2 | Y-2 | H |
| 791 | Z-h | Y-2 | H | Y-2 | Y-2 | Y-2 | Y-2 |
| 792 | Z-h | Y-2 | Y-2 | H | H | H | H |
| 793 | Z-h | Y-2 | Y-2 | H | H | H | Y-2 |
| 794 | Z-h | Y-2 | Y-2 | H | H | Y-2 | H |
| 795 | Z-h | Y-2 | Y-2 | H | H | Y-2 | Y-2 |
| 796 | Z-h | Y-2 | Y-2 | H | Y-2 | H | H |
| 797 | Z-h | Y-2 | Y-2 | H | Y-2 | H | Y-2 |
| 798 | Z-h | Y-2 | Y-2 | H | Y-2 | Y-2 | H |
| 799 | Z-h | Y-2 | Y-2 | H | Y-2 | Y-2 | Y-2 |
| 800 | Z-h | Y-2 | Y-2 | Y-2 | H | H | H |
| 801 | Z-h | Y-2 | Y-2 | Y-2 | H | H | Y-2 |
| 802 | Z-h | Y-2 | Y-2 | Y-2 | H | Y-2 | H |
| 803 | Z-h | Y-2 | Y-2 | Y-2 | H | Y-2 | Y-2 |
| 804 | Z-h | Y-2 | Y-2 | Y-2 | Y-2 | H | H |
| 805 | Z-h | Y-2 | Y-2 | Y-2 | Y-2 | H | Y-2 |
| 806 | Z-h | Y-2 | Y-2 | Y-2 | Y-2 | Y-2 | H |
| 807 | Z-h | Y-2 | Y-2 | Y-2 | Y-2 | Y-2 | Y-2 |
| 808 | Z-h | H | H | H | H | H | Y-3 |
| 809 | Z-h | H | H | H | H | Y-3 | H |
| 810 | Z-h | H | H | H | H | Y-3 | Y-3 |
| 811 | Z-h | H | H | H | Y-3 | H | H |
| 812 | Z-h | H | H | H | Y-3 | H | Y-3 |
| 813 | Z-h | H | H | H | Y-3 | Y-3 | H |
| 814 | Z-h | H | H | H | Y-3 | Y-3 | Y-3 |
| 815 | Z-h | H | H | Y-3 | H | H | H |
| 816 | Z-h | H | H | Y-3 | H | H | Y-3 |
| 817 | Z-h | H | H | Y-3 | H | Y-3 | H |
| 818 | Z-h | H | H | Y-3 | H | Y-3 | Y-3 |
| 819 | Z-h | H | H | Y-3 | Y-3 | H | H |
| 820 | Z-h | H | H | Y-3 | Y-3 | H | Y-3 |
| 821 | Z-h | H | H | Y-3 | Y-3 | Y-3 | H |
| 822 | Z-h | H | H | Y-3 | Y-3 | Y-3 | Y-3 |
| 823 | Z-h | H | Y-3 | H | H | H | H |
| 824 | Z-h | H | Y-3 | H | H | H | Y-3 |
| 825 | Z-h | H | Y-3 | H | H | Y-3 | H |
| 826 | Z-h | H | Y-3 | H | H | Y-3 | Y-3 |
| 827 | Z-h | H | Y-3 | H | Y-3 | H | H |
| 828 | Z-h | H | Y-3 | H | Y-3 | H | Y-3 |
| 829 | Z-h | H | Y-3 | H | Y-3 | Y-3 | H |
| 830 | Z-h | H | Y-3 | H | Y-3 | Y-3 | Y-3 |
| 831 | Z-h | H | Y-3 | Y-3 | H | H | H |
| 832 | Z-h | H | Y-3 | Y-3 | H | H | Y-3 |
| 833 | Z-h | H | Y-3 | Y-3 | H | Y-3 | H |
| 834 | Z-h | H | Y-3 | Y-3 | H | Y-3 | Y-3 |
| 835 | Z-h | H | Y-3 | Y-3 | Y-3 | H | H |
| 836 | Z-h | H | Y-3 | Y-3 | Y-3 | H | Y-3 |
| 837 | Z-h | H | Y-3 | Y-3 | Y-3 | Y-3 | H |
| 838 | Z-h | H | Y-3 | Y-3 | Y-3 | Y-3 | Y-3 |
| 839 | Z-h | Y-3 | H | H | H | H | H |
| 840 | Z-h | Y-3 | H | H | H | H | Y-3 |
| 841 | Z-h | Y-3 | H | H | H | Y-3 | H |
| 842 | Z-h | Y-3 | H | H | H | Y-3 | Y-3 |
| 843 | Z-h | Y-3 | H | H | Y-3 | H | H |
| 844 | Z-h | Y-3 | H | H | Y-3 | H | Y-3 |
| 845 | Z-h | Y-3 | H | H | Y-3 | Y-3 | H |
| 846 | Z-h | Y-3 | H | H | Y-3 | Y-3 | Y-3 |
| 847 | Z-h | Y-3 | H | Y-3 | H | H | H |
| 848 | Z-h | Y-3 | H | Y-3 | H | H | Y-3 |
| 849 | Z-h | Y-3 | H | Y-3 | H | Y-3 | H |
| 850 | Z-h | Y-3 | H | Y-3 | H | Y-3 | Y-3 |
| 851 | Z-h | Y-3 | H | Y-3 | Y-3 | H | H |
| 852 | Z-h | Y-3 | H | Y-3 | Y-3 | H | Y-3 |
| 853 | Z-h | Y-3 | H | Y-3 | Y-3 | Y-3 | H |
| 854 | Z-h | Y-3 | H | Y-3 | Y-3 | Y-3 | Y-3 |
| 855 | Z-h | Y-3 | Y-3 | H | H | H | H |
| 856 | Z-h | Y-3 | Y-3 | H | H | H | Y-3 |
| 857 | Z-h | Y-3 | Y-3 | H | H | Y-3 | H |
| 858 | Z-h | Y-3 | Y-3 | H | H | Y-3 | Y-3 |
| 859 | Z-h | Y-3 | Y-3 | H | Y-3 | H | H |
| 860 | Z-h | Y-3 | Y-3 | H | Y-3 | H | Y-3 |
| 861 | Z-h | Y-3 | Y-3 | H | Y-3 | Y-3 | H |
| 862 | Z-h | Y-3 | Y-3 | H | Y-3 | Y-3 | Y-3 |
| 863 | Z-h | Y-3 | Y-3 | Y-3 | H | H | H |
| 864 | Z-h | Y-3 | Y-3 | Y-3 | H | H | Y-3 |
| 865 | Z-h | Y-3 | Y-3 | Y-3 | H | Y-3 | H |
| 866 | Z-h | Y-3 | Y-3 | Y-3 | H | Y-3 | Y-3 |
| 867 | Z-h | Y-3 | Y-3 | Y-3 | Y-3 | H | H |
| 868 | Z-h | Y-3 | Y-3 | Y-3 | Y-3 | H | Y-3 |
| 869 | Z-h | Y-3 | Y-3 | Y-3 | Y-3 | Y-3 | H |
| 870 | Z-h | Y-3 | Y-3 | Y-3 | Y-3 | Y-3 | Y-3 |
| 871 | Z-i | H | H | H | Y-1 | — | — |
| 872 | Z-i | H | H | Y-1 | H | — | — |
| 873 | Z-i | H | H | Y-1 | Y-1 | — | — |
| 874 | Z-i | H | Y-1 | H | H | — | — |
| 875 | Z-i | H | Y-1 | H | Y-1 | — | — |
| 876 | Z-i | H | Y-1 | Y-1 | H | — | — |
| 877 | Z-i | H | Y-1 | Y-1 | Y-1 | — | — |
| 878 | Z-i | Y-1 | H | H | H | — | — |
| 879 | Z-i | Y-1 | H | H | Y-1 | — | — |
| 880 | Z-i | Y-1 | H | Y-1 | H | — | — |
| 881 | Z-i | Y-1 | H | Y-1 | Y-1 | — | — |
| 882 | Z-i | Y-1 | Y-1 | H | H | — | — |
| 883 | Z-i | Y-1 | Y-1 | H | Y-1 | — | — |
| 884 | Z-i | Y-1 | Y-1 | Y-1 | H | — | — |
| 885 | Z-i | Y-1 | Y-1 | Y-1 | Y-1 | — | — |
| 886 | Z-i | H | H | H | Y-2 | — | — |
| 887 | Z-i | H | H | Y-2 | H | — | — |
| 888 | Z-i | H | H | Y-2 | Y-2 | — | — |
| 889 | Z-i | H | Y-2 | H | H | — | — |
| 890 | Z-i | H | Y-2 | H | Y-2 | — | — |

| No. | Z | $R^a$ | $R^b$ | $R^c$ | $R^d$ | $R^e$ | $R^f$ |
|---|---|---|---|---|---|---|---|
| 891 | Z-i | H | Y-2 | Y-2 | H | — | — |
| 892 | Z-i | H | Y-2 | Y-2 | Y-2 | — | — |
| 893 | Z-i | Y-2 | H | H | H | — | — |
| 894 | Z-i | Y-2 | H | H | Y-2 | — | — |
| 895 | Z-i | Y-2 | H | Y-2 | H | — | — |
| 896 | Z-i | Y-2 | H | Y-2 | Y-2 | — | — |
| 897 | Z-i | Y-2 | Y-2 | H | H | — | — |
| 898 | Z-i | Y-2 | Y-2 | H | Y-2 | — | — |
| 899 | Z-i | Y-2 | Y-2 | Y-2 | H | — | — |
| 900 | Z-i | Y-2 | Y-2 | Y-2 | Y-2 | — | — |
| 901 | Z-i | H | H | H | Y-3 | — | — |
| 902 | Z-i | H | H | Y-3 | H | — | — |
| 903 | Z-i | H | H | Y-3 | Y-3 | — | — |
| 904 | Z-i | H | Y-3 | H | H | — | — |
| 905 | Z-i | H | Y-3 | H | Y-3 | — | — |
| 906 | Z-i | H | Y-3 | Y-3 | H | — | — |
| 907 | Z-i | H | Y-3 | Y-3 | Y-3 | — | — |
| 908 | Z-i | Y-3 | H | H | H | — | — |
| 909 | Z-i | Y-3 | H | H | Y-3 | — | — |
| 910 | Z-i | Y-3 | H | Y-3 | H | — | — |
| 911 | Z-i | Y-3 | H | Y-3 | Y-3 | — | — |
| 912 | Z-i | Y-3 | Y-3 | H | H | — | — |
| 913 | Z-i | Y-3 | Y-3 | H | Y-3 | — | — |
| 914 | Z-i | Y-3 | Y-3 | Y-3 | H | — | — |
| 915 | Z-i | Y-3 | Y-3 | Y-3 | Y-3 | — | — |
| 916 | Z-j | H | H | H | Y-1 | — | — |
| 917 | Z-j | H | H | Y-1 | H | — | — |
| 918 | Z-j | H | H | Y-1 | Y-1 | — | — |
| 919 | Z-j | H | Y-1 | H | H | — | — |
| 920 | Z-j | H | Y-1 | H | Y-1 | — | — |
| 921 | Z-j | H | Y-1 | Y-1 | H | — | — |
| 922 | Z-j | H | Y-1 | Y-1 | Y-1 | — | — |
| 923 | Z-j | Y-1 | H | H | H | — | — |
| 924 | Z-j | Y-1 | H | H | Y-1 | — | — |
| 925 | Z-j | Y-1 | H | Y-1 | H | — | — |
| 926 | Z-j | Y-1 | H | Y-1 | Y-1 | — | — |
| 927 | Z-j | Y-1 | Y-1 | H | H | — | — |
| 928 | Z-j | Y-1 | Y-1 | H | Y-1 | — | — |
| 929 | Z-j | Y-1 | Y-1 | Y-1 | H | — | — |
| 930 | Z-j | Y-1 | Y-1 | Y-1 | Y-1 | — | — |
| 931 | Z-j | H | H | H | Y-2 | — | — |
| 932 | Z-j | H | H | Y-2 | H | — | — |
| 933 | Z-j | H | H | Y-2 | Y-2 | — | — |
| 934 | Z-j | H | Y-2 | H | H | — | — |
| 935 | Z-j | H | Y-2 | H | Y-2 | — | — |
| 936 | Z-j | H | Y-2 | Y-2 | H | — | — |
| 937 | Z-j | H | Y-2 | Y-2 | Y-2 | — | — |
| 938 | Z-j | Y-2 | H | H | H | — | — |
| 939 | Z-j | Y-2 | H | H | Y-2 | — | — |
| 940 | Z-j | Y-2 | H | Y-2 | H | — | — |
| 941 | Z-j | Y-2 | H | Y-2 | Y-2 | — | — |
| 942 | Z-j | Y-2 | Y-2 | H | H | — | — |
| 943 | Z-j | Y-2 | Y-2 | H | Y-2 | — | — |
| 944 | Z-j | Y-2 | Y-2 | Y-2 | H | — | — |
| 945 | Z-j | Y-2 | Y-2 | Y-2 | Y-2 | — | — |
| 946 | Z-j | H | H | H | Y-3 | — | — |
| 947 | Z-j | H | H | Y-3 | H | — | — |
| 948 | Z-j | H | H | Y-3 | Y-3 | — | — |
| 949 | Z-j | H | Y-3 | H | H | — | — |
| 950 | Z-j | H | Y-3 | H | Y-3 | — | — |
| 951 | Z-j | H | Y-3 | Y-3 | H | — | — |
| 952 | Z-j | H | Y-3 | Y-3 | Y-3 | — | — |
| 953 | Z-j | Y-3 | H | H | H | — | — |
| 954 | Z-j | Y-3 | H | H | Y-3 | — | — |
| 955 | Z-j | Y-3 | H | Y-3 | H | — | — |
| 956 | Z-j | Y-3 | H | Y-3 | Y-3 | — | — |
| 957 | Z-j | Y-3 | Y-3 | H | H | — | — |
| 958 | Z-j | Y-3 | Y-3 | H | Y-3 | — | — |
| 959 | Z-j | Y-3 | Y-3 | Y-3 | H | — | — |
| 960 | Z-j | Y-3 | Y-3 | Y-3 | Y-3 | — | — |
| 961 | Z-k | Y-1 | — | — | — | — | — |
| 962 | Z-k | Y-2 | — | — | — | — | — |
| 963 | Z-k | Y-3 | — | — | — | — | — |
| 964 | Z-l | H | H | Y-1 | — | — | — |
| 965 | Z-l | H | Y-1 | H | — | — | — |
| 966 | Z-l | H | Y-1 | Y-1 | — | — | — |
| 967 | Z-l | Y-1 | H | H | — | — | — |
| 968 | Z-l | Y-1 | H | Y-1 | — | — | — |
| 969 | Z-l | Y-1 | Y-1 | H | — | — | — |
| 970 | Z-l | Y-1 | Y-1 | Y-1 | — | — | — |
| 971 | Z-l | H | H | Y-2 | — | — | — |
| 972 | Z-l | H | Y-2 | H | — | — | — |
| 973 | Z-l | H | Y-2 | Y-2 | — | — | — |
| 974 | Z-l | Y-2 | H | H | — | — | — |
| 975 | Z-l | Y-2 | H | Y-2 | — | — | — |
| 976 | Z-l | Y-2 | Y-2 | H | — | — | — |
| 977 | Z-l | Y-2 | Y-2 | Y-2 | — | — | — |
| 978 | Z-l | H | H | Y-3 | — | — | — |
| 979 | Z-l | H | Y-3 | H | — | — | — |
| 980 | Z-l | H | Y-3 | Y-3 | — | — | — |
| 981 | Z-l | Y-3 | H | H | — | — | — |
| 982 | Z-l | Y-3 | H | Y-3 | — | — | — |
| 983 | Z-l | Y-3 | Y-3 | H | — | — | — |
| 984 | Z-l | Y-3 | Y-3 | Y-3 | — | — | — |
| 985 | Z-m | H | H | H | Y-1 | — | — |
| 986 | Z-m | H | H | Y-1 | H | — | — |
| 987 | Z-m | H | H | Y-1 | Y-1 | — | — |
| 988 | Z-m | H | Y-1 | H | H | — | — |
| 989 | Z-m | H | Y-1 | H | Y-1 | — | — |
| 990 | Z-m | H | Y-1 | Y-1 | H | — | — |
| 991 | Z-m | H | Y-1 | Y-1 | Y-1 | — | — |
| 992 | Z-m | Y-1 | H | H | H | — | — |
| 993 | Z-m | Y-1 | H | H | Y-1 | — | — |
| 994 | Z-m | Y-1 | H | Y-1 | H | — | — |
| 995 | Z-m | Y-1 | H | Y-1 | Y-1 | — | — |
| 996 | Z-m | Y-1 | Y-1 | H | H | — | — |
| 997 | Z-m | Y-1 | Y-1 | H | Y-1 | — | — |
| 998 | Z-m | Y-1 | Y-1 | Y-1 | H | — | — |
| 999 | Z-m | Y-1 | Y-1 | Y-1 | Y-1 | — | — |
| 1000 | Z-m | H | H | H | Y-2 | — | — |
| 1001 | Z-m | H | H | Y-2 | H | — | — |
| 1002 | Z-m | H | H | Y-2 | Y-2 | — | — |
| 1003 | Z-m | H | Y-2 | H | H | — | — |
| 1004 | Z-m | H | Y-2 | H | Y-2 | — | — |
| 1005 | Z-m | H | Y-2 | Y-2 | H | — | — |
| 1006 | Z-m | H | Y-2 | Y-2 | Y-2 | — | — |
| 1007 | Z-m | Y-2 | H | H | H | — | — |
| 1008 | Z-m | Y-2 | H | H | Y-2 | — | — |
| 1009 | Z-m | Y-2 | H | Y-2 | H | — | — |
| 1010 | Z-m | Y-2 | H | Y-2 | Y-2 | — | — |
| 1011 | Z-m | Y-2 | Y-2 | H | H | — | — |
| 1012 | Z-m | Y-2 | Y-2 | H | Y-2 | — | — |
| 1013 | Z-m | Y-2 | Y-2 | Y-2 | H | — | — |
| 1014 | Z-m | Y-2 | Y-2 | Y-2 | Y-2 | — | — |
| 1015 | Z-m | H | H | H | Y-3 | — | — |
| 1016 | Z-m | H | H | Y-3 | H | — | — |
| 1017 | Z-m | H | H | Y-3 | Y-3 | — | — |
| 1018 | Z-m | H | Y-3 | H | H | — | — |
| 1019 | Z-m | H | Y-3 | H | Y-3 | — | — |
| 1020 | Z-m | H | Y-3 | Y-3 | H | — | — |
| 1021 | Z-m | H | Y-3 | Y-3 | Y-3 | — | — |
| 1022 | Z-m | Y-3 | H | H | H | — | — |
| 1023 | Z-m | Y-3 | H | H | Y-3 | — | — |
| 1024 | Z-m | Y-3 | H | Y-3 | H | — | — |
| 1025 | Z-m | Y-3 | H | Y-3 | Y-3 | — | — |
| 1026 | Z-m | Y-3 | Y-3 | H | H | — | — |
| 1027 | Z-m | Y-3 | Y-3 | H | Y-3 | — | — |
| 1028 | Z-m | Y-3 | Y-3 | Y-3 | H | — | — |
| 1029 | Z-m | Y-3 | Y-3 | Y-3 | Y-3 | — | — |
| 1030 | Z-n | H | H | H | Y-1 | — | — |
| 1031 | Z-n | H | H | Y-1 | H | — | — |
| 1032 | Z-n | H | H | Y-1 | Y-1 | — | — |
| 1033 | Z-n | H | Y-1 | H | H | — | — |
| 1034 | Z-n | H | Y-1 | H | Y-1 | — | — |
| 1035 | Z-n | H | Y-1 | Y-1 | H | — | — |
| 1036 | Z-n | H | Y-1 | Y-1 | Y-1 | — | — |
| 1037 | Z-n | Y-1 | H | H | H | — | — |

| No. | Z | $R^a$ | $R^b$ | $R^c$ | $R^d$ | $R^e$ | $R^f$ |
|---|---|---|---|---|---|---|---|
| 1038 | Z-n | Y-1 | H | H | Y-1 | — | — |
| 1039 | Z-n | Y-1 | H | Y-1 | H | — | — |
| 1040 | Z-n | Y-1 | H | Y-1 | Y-1 | — | — |
| 1041 | Z-n | Y-1 | Y-1 | H | H | — | — |
| 1042 | Z-n | Y-1 | Y-1 | H | Y-1 | — | — |
| 1043 | Z-n | Y-1 | Y-1 | Y-1 | H | — | — |
| 1044 | Z-n | Y-1 | Y-1 | Y-1 | Y-1 | — | — |
| 1045 | Z-n | H | H | H | Y-2 | — | — |
| 1046 | Z-n | H | H | Y-2 | H | — | — |
| 1047 | Z-n | H | H | Y-2 | Y-2 | — | — |
| 1048 | Z-n | H | Y-2 | H | H | — | — |
| 1049 | Z-n | H | Y-2 | H | Y-2 | — | — |
| 1050 | Z-n | H | Y-2 | Y-2 | H | — | — |
| 1051 | Z-n | H | Y-2 | Y-2 | Y-2 | — | — |
| 1052 | Z-n | Y-2 | H | H | H | — | — |
| 1053 | Z-n | Y-2 | H | H | Y-2 | — | — |
| 1054 | Z-n | Y-2 | H | Y-2 | H | — | — |
| 1055 | Z-n | Y-2 | H | Y-2 | Y-2 | — | — |
| 1056 | Z-n | Y-2 | Y-2 | H | H | — | — |
| 1057 | Z-n | Y-2 | Y-2 | H | Y-2 | — | — |
| 1058 | Z-n | Y-2 | Y-2 | Y-2 | H | — | — |
| 1059 | Z-n | Y-2 | Y-2 | Y-2 | Y-2 | — | — |
| 1060 | Z-n | H | H | H | Y-3 | — | — |
| 1061 | Z-n | H | H | Y-3 | H | — | — |
| 1062 | Z-n | H | H | Y-3 | Y-3 | — | — |
| 1063 | Z-n | H | Y-3 | H | H | — | — |
| 1064 | Z-n | H | Y-3 | H | Y-3 | — | — |
| 1065 | Z-n | H | Y-3 | Y-3 | H | — | — |
| 1066 | Z-n | H | Y-3 | Y-3 | Y-3 | — | — |
| 1067 | Z-n | Y-3 | H | H | H | — | — |
| 1068 | Z-n | Y-3 | H | H | Y-3 | — | — |
| 1069 | Z-n | Y-3 | H | Y-3 | H | — | — |
| 1070 | Z-n | Y-3 | H | Y-3 | Y-3 | — | — |
| 1071 | Z-n | Y-3 | Y-3 | H | H | — | — |
| 1072 | Z-n | Y-3 | Y-3 | H | Y-3 | — | — |
| 1073 | Z-n | Y-3 | Y-3 | Y-3 | H | — | — |
| 1074 | Z-n | Y-3 | Y-3 | Y-3 | Y-3 | — | — |
| 1075 | Z-o | H | H | H | H | Y-1 | — |
| 1076 | Z-o | H | H | H | Y-1 | H | — |
| 1077 | Z-o | H | H | H | Y-1 | Y-1 | — |
| 1078 | Z-o | H | H | Y-1 | H | H | — |
| 1079 | Z-o | H | H | Y-1 | H | Y-1 | — |
| 1080 | Z-o | H | H | Y-1 | Y-1 | H | — |
| 1081 | Z-o | H | H | Y-1 | Y-1 | Y-1 | — |
| 1082 | Z-o | H | Y-1 | H | H | H | — |
| 1083 | Z-o | H | Y-1 | H | H | Y-1 | — |
| 1084 | Z-o | H | Y-1 | H | Y-1 | H | — |
| 1085 | Z-o | H | Y-1 | H | Y-1 | Y-1 | — |
| 1086 | Z-o | H | Y-1 | Y-1 | H | H | — |
| 1087 | Z-o | H | Y-1 | Y-1 | H | Y-1 | — |
| 1088 | Z-o | H | Y-1 | Y-1 | Y-1 | H | — |
| 1089 | Z-o | H | Y-1 | Y-1 | Y-1 | Y-1 | — |
| 1090 | Z-o | Y-1 | H | H | H | H | — |
| 1091 | Z-o | Y-1 | H | H | H | Y-1 | — |
| 1092 | Z-o | Y-1 | H | H | Y-1 | H | — |
| 1093 | Z-o | Y-1 | H | H | Y-1 | Y-1 | — |
| 1094 | Z-o | Y-1 | H | Y-1 | H | H | — |
| 1095 | Z-o | Y-1 | H | Y-1 | H | Y-1 | — |
| 1096 | Z-o | Y-1 | H | Y-1 | Y-1 | H | — |
| 1097 | Z-o | Y-1 | H | Y-1 | Y-1 | Y-1 | — |
| 1098 | Z-o | Y-1 | Y-1 | H | H | H | — |
| 1099 | Z-o | Y-1 | Y-1 | H | H | Y-1 | — |
| 1100 | Z-o | Y-1 | Y-1 | H | Y-1 | H | — |
| 1101 | Z-o | Y-1 | Y-1 | H | Y-1 | Y-1 | — |
| 1102 | Z-o | Y-1 | Y-1 | Y-1 | H | H | — |
| 1103 | Z-o | Y-1 | Y-1 | Y-1 | H | Y-1 | — |
| 1104 | Z-o | Y-1 | Y-1 | Y-1 | Y-1 | H | — |
| 1105 | Z-o | Y-1 | Y-1 | Y-1 | Y-1 | Y-1 | — |
| 1106 | Z-o | H | H | H | H | Y-2 | — |
| 1107 | Z-o | H | H | H | Y-2 | H | — |
| 1108 | Z-o | H | H | H | Y-2 | Y-2 | — |
| 1109 | Z-o | H | H | Y-2 | H | H | — |
| 1110 | Z-o | H | H | Y-2 | H | Y-2 | — |
| 1111 | Z-o | H | H | Y-2 | Y-2 | H | — |
| 1112 | Z-o | H | H | Y-2 | Y-2 | Y-2 | — |
| 1113 | Z-o | H | Y-2 | H | H | H | — |
| 1114 | Z-o | H | Y-2 | H | H | Y-2 | — |
| 1115 | Z-o | H | Y-2 | H | Y-2 | H | — |
| 1116 | Z-o | H | Y-2 | H | Y-2 | Y-2 | — |
| 1117 | Z-o | H | Y-2 | Y-2 | H | H | — |
| 1118 | Z-o | H | Y-2 | Y-2 | H | Y-2 | — |
| 1119 | Z-o | H | Y-2 | Y-2 | Y-2 | H | — |
| 1120 | Z-o | H | Y-2 | Y-2 | Y-2 | Y-2 | — |
| 1121 | Z-o | Y-2 | H | H | H | H | — |
| 1122 | Z-o | Y-2 | H | H | H | Y-2 | — |
| 1123 | Z-o | Y-2 | H | H | Y-2 | H | — |
| 1124 | Z-o | Y-2 | H | H | Y-2 | Y-2 | — |
| 1125 | Z-o | Y-2 | H | Y-2 | H | H | — |
| 1126 | Z-o | Y-2 | H | Y-2 | H | Y-2 | — |
| 1127 | Z-o | Y-2 | H | Y-2 | Y-2 | H | — |
| 1128 | Z-o | Y-2 | H | Y-2 | Y-2 | Y-2 | — |
| 1129 | Z-o | Y-2 | Y-2 | H | H | H | — |
| 1130 | Z-o | Y-2 | Y-2 | H | H | Y-2 | — |
| 1131 | Z-o | Y-2 | Y-2 | H | Y-2 | H | — |
| 1132 | Z-o | Y-2 | Y-2 | H | Y-2 | Y-2 | — |
| 1133 | Z-o | Y-2 | Y-2 | Y-2 | H | H | — |
| 1134 | Z-o | Y-2 | Y-2 | Y-2 | H | Y-2 | — |
| 1135 | Z-o | Y-2 | Y-2 | Y-2 | Y-2 | H | — |
| 1136 | Z-o | Y-2 | Y-2 | Y-2 | Y-2 | Y-2 | — |
| 1137 | Z-o | H | H | H | H | Y-3 | — |
| 1138 | Z-o | H | H | H | Y-3 | H | — |
| 1139 | Z-o | H | H | H | Y-3 | Y-3 | — |
| 1140 | Z-o | H | H | Y-3 | H | H | — |
| 1141 | Z-o | H | H | Y-3 | H | Y-3 | — |
| 1142 | Z-o | H | H | Y-3 | Y-3 | H | — |
| 1143 | Z-o | H | H | Y-3 | Y-3 | Y-3 | — |
| 1144 | Z-o | H | Y-3 | H | H | H | — |
| 1145 | Z-o | H | Y-3 | H | H | Y-3 | — |
| 1146 | Z-o | H | Y-3 | H | Y-3 | H | — |
| 1147 | Z-o | H | Y-3 | H | Y-3 | Y-3 | — |
| 1148 | Z-o | H | Y-3 | Y-3 | H | H | — |
| 1149 | Z-o | H | Y-3 | Y-3 | H | Y-3 | — |
| 1150 | Z-o | H | Y-3 | Y-3 | Y-3 | H | — |
| 1151 | Z-o | H | Y-3 | Y-3 | Y-3 | Y-3 | — |
| 1152 | Z-o | Y-3 | H | H | H | H | — |
| 1153 | Z-o | Y-3 | H | H | H | Y-3 | — |
| 1154 | Z-o | Y-3 | H | H | Y-3 | H | — |
| 1155 | Z-o | Y-3 | H | H | Y-3 | Y-3 | — |
| 1156 | Z-o | Y-3 | H | Y-3 | H | H | — |
| 1157 | Z-o | Y-3 | H | Y-3 | H | Y-3 | — |
| 1158 | Z-o | Y-3 | H | Y-3 | Y-3 | H | — |
| 1159 | Z-o | Y-3 | H | Y-3 | Y-3 | Y-3 | — |
| 1160 | Z-o | Y-3 | Y-3 | H | H | H | — |
| 1161 | Z-o | Y-3 | Y-3 | H | H | Y-3 | — |
| 1162 | Z-o | Y-3 | Y-3 | H | Y-3 | H | — |
| 1163 | Z-o | Y-3 | Y-3 | H | Y-3 | Y-3 | — |
| 1164 | Z-o | Y-3 | Y-3 | Y-3 | H | H | — |
| 1165 | Z-o | Y-3 | Y-3 | Y-3 | H | Y-3 | — |
| 1166 | Z-o | Y-3 | Y-3 | Y-3 | Y-3 | H | — |
| 1167 | Z-o | Y-3 | Y-3 | Y-3 | Y-3 | Y-3 | — |
| 1168 | Z-p | Y-1 | — | — | — | — | — |
| 1169 | Z-p | Y-2 | — | — | — | — | — |
| 1170 | Z-p | Y-3 | — | — | — | — | — |
| 1171 | Z-q | H | H | H | Y-1 | — | — |
| 1172 | Z-q | H | H | Y-1 | H | — | — |
| 1173 | Z-q | H | H | Y-1 | Y-1 | — | — |
| 1174 | Z-q | H | Y-1 | H | H | — | — |
| 1175 | Z-q | H | Y-1 | H | Y-1 | — | — |
| 1176 | Z-q | H | Y-1 | Y-1 | H | — | — |
| 1177 | Z-q | H | Y-1 | Y-1 | Y-1 | — | — |
| 1178 | Z-q | Y-1 | H | H | H | — | — |
| 1179 | Z-q | Y-1 | H | H | Y-1 | — | — |
| 1180 | Z-q | Y-1 | H | Y-1 | H | — | — |
| 1181 | Z-q | Y-1 | H | Y-1 | Y-1 | — | — |
| 1182 | Z-q | Y-1 | Y-1 | H | H | — | — |
| 1183 | Z-q | Y-1 | Y-1 | H | Y-1 | — | — |
| 1184 | Z-q | Y-1 | Y-1 | Y-1 | H | — | — |
| 1185 | Z-q | Y-1 | Y-1 | Y-1 | Y-1 | — | — |
| 1186 | Z-q | H | H | H | Y-2 | — | — |
| 1187 | Z-q | H | H | Y-2 | H | — | — |
| 1188 | Z-q | H | H | Y-2 | Y-2 | — | — |
| 1189 | Z-q | H | Y-2 | H | H | — | — |
| 1190 | Z-q | H | Y-2 | H | Y-2 | — | — |
| 1191 | Z-q | H | Y-2 | Y-2 | H | — | — |

| No. | Z | $R^a$ | $R^b$ | $R^c$ | $R^d$ | $R^e$ | $R^f$ |
|---|---|---|---|---|---|---|---|
| 1192 | Z-q | H | Y-2 | Y-2 | Y-2 | — | — |
| 1193 | Z-q | Y-2 | H | H | H | — | — |
| 1194 | Z-q | Y-2 | H | H | Y-2 | — | — |
| 1195 | Z-q | Y-2 | H | Y-2 | H | — | — |
| 1196 | Z-q | Y-2 | H | Y-2 | Y-2 | — | — |
| 1197 | Z-q | Y-2 | Y-2 | H | H | — | — |
| 1198 | Z-q | Y-2 | Y-2 | H | Y-2 | — | — |
| 1199 | Z-q | Y-2 | Y-2 | Y-2 | H | — | — |
| 1200 | Z-q | Y-2 | Y-2 | Y-2 | Y-2 | — | — |
| 1201 | Z-q | H | H | H | Y-3 | — | — |
| 1202 | Z-q | H | H | Y-3 | H | — | — |
| 1203 | Z-q | H | H | Y-3 | Y-3 | — | — |
| 1204 | Z-q | H | Y-3 | H | H | — | — |
| 1205 | Z-q | H | Y-3 | H | Y-3 | — | — |
| 1206 | Z-q | H | Y-3 | Y-3 | H | — | — |
| 1207 | Z-q | H | Y-3 | Y-3 | Y-3 | — | — |
| 1208 | Z-q | Y-3 | H | H | H | — | — |
| 1209 | Z-q | Y-3 | H | H | Y-3 | — | — |
| 1210 | Z-q | Y-3 | H | Y-3 | H | — | — |
| 1211 | Z-q | Y-3 | H | Y-3 | Y-3 | — | — |
| 1212 | Z-q | Y-3 | Y-3 | H | H | — | — |
| 1213 | Z-q | Y-3 | Y-3 | H | Y-3 | — | — |
| 1214 | Z-q | Y-3 | Y-3 | Y-3 | H | — | — |
| 1215 | Z-q | Y-3 | Y-3 | Y-3 | Y-3 | — | — |
| 1216 | Z-r | H | H | H | Y-1 | H | — |
| 1217 | Z-r | H | H | H | Y-1 | H | — |
| 1218 | Z-r | H | H | H | Y-1 | Y-1 | — |
| 1219 | Z-r | H | H | Y-1 | H | H | — |
| 1220 | Z-r | H | H | Y-1 | H | Y-1 | — |
| 1221 | Z-r | H | H | Y-1 | Y-1 | H | — |
| 1222 | Z-r | H | H | Y-1 | Y-1 | Y-1 | — |
| 1223 | Z-r | H | Y-1 | H | H | H | — |
| 1224 | Z-r | H | Y-1 | H | H | Y-1 | — |
| 1225 | Z-r | H | Y-1 | H | Y-1 | H | — |
| 1226 | Z-r | H | Y-1 | H | Y-1 | Y-1 | — |
| 1227 | Z-r | H | Y-1 | Y-1 | H | H | — |
| 1228 | Z-r | H | Y-1 | Y-1 | H | Y-1 | — |
| 1229 | Z-r | H | Y-1 | Y-1 | Y-1 | H | — |
| 1230 | Z-r | H | Y-1 | Y-1 | Y-1 | Y-1 | — |
| 1231 | Z-r | Y-1 | H | H | H | H | — |
| 1232 | Z-r | Y-1 | H | H | H | Y-1 | — |
| 1233 | Z-r | Y-1 | H | H | Y-1 | H | — |
| 1234 | Z-r | Y-1 | H | H | Y-1 | Y-1 | — |
| 1235 | Z-r | Y-1 | H | Y-1 | H | H | — |
| 1236 | Z-r | Y-1 | H | Y-1 | H | Y-1 | — |
| 1237 | Z-r | Y-1 | H | Y-1 | Y-1 | H | — |
| 1238 | Z-r | Y-1 | H | Y-1 | Y-1 | Y-1 | — |
| 1239 | Z-r | Y-1 | Y-1 | H | H | H | — |
| 1240 | Z-r | Y-1 | Y-1 | H | H | Y-1 | — |
| 1241 | Z-r | Y-1 | Y-1 | H | Y-1 | H | — |
| 1242 | Z-r | Y-1 | Y-1 | H | Y-1 | Y-1 | — |
| 1243 | Z-r | Y-1 | Y-1 | Y-1 | H | H | — |
| 1244 | Z-r | Y-1 | Y-1 | Y-1 | H | Y-1 | — |
| 1245 | Z-r | Y-1 | Y-1 | Y-1 | Y-1 | H | — |
| 1246 | Z-r | Y-1 | Y-1 | Y-1 | Y-1 | Y-1 | — |
| 1247 | Z-r | H | H | H | H | Y-2 | — |
| 1248 | Z-r | H | H | H | Y-2 | H | — |
| 1249 | Z-r | H | H | H | Y-2 | Y-2 | — |
| 1250 | Z-r | H | H | Y-2 | H | H | — |
| 1251 | Z-r | H | H | Y-2 | H | Y-2 | — |
| 1252 | Z-r | H | H | Y-2 | Y-2 | H | — |
| 1253 | Z-r | H | H | Y-2 | Y-2 | Y-2 | — |
| 1254 | Z-r | H | Y-2 | H | H | H | — |
| 1255 | Z-r | H | Y-2 | H | H | Y-2 | — |
| 1256 | Z-r | H | Y-2 | H | Y-2 | H | — |
| 1257 | Z-r | H | Y-2 | H | Y-2 | Y-2 | — |
| 1258 | Z-r | H | Y-2 | Y-2 | H | H | — |
| 1259 | Z-r | H | Y-2 | Y-2 | H | Y-2 | — |
| 1260 | Z-r | H | Y-2 | Y-2 | Y-2 | H | — |
| 1261 | Z-r | H | Y-2 | Y-2 | Y-2 | Y-2 | — |
| 1262 | Z-r | Y-2 | H | H | H | H | — |
| 1263 | Z-r | Y-2 | H | H | H | Y-2 | — |
| 1264 | Z-r | Y-2 | H | H | Y-2 | H | — |
| 1265 | Z-r | Y-2 | H | H | Y-2 | Y-2 | — |
| 1266 | Z-r | Y-2 | H | Y-2 | H | H | — |
| 1267 | Z-r | Y-2 | H | Y-2 | H | Y-2 | — |
| 1268 | Z-r | Y-2 | H | Y-2 | Y-2 | H | — |
| 1269 | Z-r | Y-2 | H | Y-2 | Y-2 | Y-2 | — |
| 1270 | Z-r | Y-2 | Y-2 | H | H | H | — |
| 1271 | Z-r | Y-2 | Y-2 | H | H | Y-2 | — |
| 1272 | Z-r | Y-2 | Y-2 | H | Y-2 | H | — |
| 1273 | Z-r | Y-2 | Y-2 | H | Y-2 | Y-2 | — |
| 1274 | Z-r | Y-2 | Y-2 | Y-2 | H | H | — |
| 1275 | Z-r | Y-2 | Y-2 | Y-2 | H | Y-2 | — |
| 1276 | Z-r | Y-2 | Y-2 | Y-2 | Y-2 | H | — |
| 1277 | Z-r | Y-2 | Y-2 | Y-2 | Y-2 | Y-2 | — |
| 1278 | Z-r | H | H | H | H | Y-3 | — |
| 1279 | Z-r | H | H | H | Y-3 | H | — |
| 1280 | Z-r | H | H | H | Y-3 | Y-3 | — |
| 1281 | Z-r | H | H | Y-3 | H | H | — |
| 1282 | Z-r | H | H | Y-3 | H | Y-3 | — |
| 1283 | Z-r | H | H | Y-3 | Y-3 | H | — |
| 1284 | Z-r | H | H | Y-3 | Y-3 | Y-3 | — |
| 1285 | Z-r | H | Y-3 | H | H | H | — |
| 1286 | Z-r | H | Y-3 | H | H | Y-3 | — |
| 1287 | Z-r | H | Y-3 | H | Y-3 | H | — |
| 1288 | Z-r | H | Y-3 | H | Y-3 | Y-3 | — |
| 1289 | Z-r | H | Y-3 | Y-3 | H | H | — |
| 1290 | Z-r | H | Y-3 | Y-3 | H | Y-3 | — |
| 1291 | Z-r | H | Y-3 | Y-3 | Y-3 | H | — |
| 1292 | Z-r | H | Y-3 | Y-3 | Y-3 | Y-3 | — |
| 1293 | Z-r | Y-3 | H | H | H | H | — |
| 1294 | Z-r | Y-3 | H | H | H | Y-3 | — |
| 1295 | Z-r | Y-3 | H | H | Y-3 | H | — |
| 1296 | Z-r | Y-3 | H | H | Y-3 | Y-3 | — |
| 1297 | Z-r | Y-3 | H | Y-3 | H | H | — |
| 1298 | Z-r | Y-3 | H | Y-3 | H | Y-3 | — |
| 1299 | Z-r | Y-3 | H | Y-3 | Y-3 | H | — |
| 1300 | Z-r | Y-3 | H | Y-3 | Y-3 | Y-3 | — |
| 1301 | Z-r | Y-3 | Y-3 | H | H | H | — |
| 1302 | Z-r | Y-3 | Y-3 | H | H | Y-3 | — |
| 1303 | Z-r | Y-3 | Y-3 | H | Y-3 | H | — |
| 1304 | Z-r | Y-3 | Y-3 | H | Y-3 | Y-3 | — |
| 1305 | Z-r | Y-3 | Y-3 | Y-3 | H | H | — |
| 1306 | Z-r | Y-3 | Y-3 | Y-3 | H | Y-3 | — |
| 1307 | Z-r | Y-3 | Y-3 | Y-3 | Y-3 | H | — |
| 1308 | Z-r | Y-3 | Y-3 | Y-3 | Y-3 | Y-3 | — |
| 1309 | Z-s | H | H | H | H | H | Y-1 |
| 1310 | Z-s | H | H | H | H | Y-1 | H |
| 1311 | Z-s | H | H | H | H | Y-1 | Y-1 |
| 1312 | Z-s | H | H | H | Y-1 | H | H |
| 1313 | Z-s | H | H | H | Y-1 | H | Y-1 |
| 1314 | Z-s | H | H | H | Y-1 | Y-1 | H |
| 1315 | Z-s | H | H | H | Y-1 | Y-1 | Y-1 |
| 1316 | Z-s | H | H | Y-1 | H | H | H |
| 1317 | Z-s | H | H | Y-1 | H | H | Y-1 |
| 1318 | Z-s | H | H | Y-1 | H | Y-1 | H |
| 1319 | Z-s | H | H | Y-1 | H | Y-1 | Y-1 |
| 1320 | Z-s | H | H | Y-1 | Y-1 | H | H |
| 1321 | Z-s | H | H | Y-1 | Y-1 | H | Y-1 |
| 1322 | Z-s | H | H | Y-1 | Y-1 | Y-1 | H |
| 1323 | Z-s | H | H | Y-1 | Y-1 | Y-1 | Y-1 |
| 1324 | Z-s | H | Y-1 | H | H | H | H |
| 1325 | Z-s | H | Y-1 | H | H | H | Y-1 |
| 1326 | Z-s | H | Y-1 | H | H | Y-1 | H |
| 1327 | Z-s | H | Y-1 | H | H | Y-1 | Y-1 |
| 1328 | Z-s | H | Y-1 | H | Y-1 | H | H |
| 1329 | Z-s | H | Y-1 | H | Y-1 | H | Y-1 |
| 1330 | Z-s | H | Y-1 | H | Y-1 | Y-1 | H |
| 1331 | Z-s | H | Y-1 | H | Y-1 | Y-1 | Y-1 |
| 1332 | Z-s | H | Y-1 | Y-1 | H | H | H |
| 1333 | Z-s | H | Y-1 | Y-1 | H | H | Y-1 |
| 1334 | Z-s | H | Y-1 | Y-1 | H | Y-1 | H |
| 1335 | Z-s | H | Y-1 | Y-1 | H | Y-1 | Y-1 |
| 1336 | Z-s | H | Y-1 | Y-1 | Y-1 | H | H |

| No. | Z | $R^a$ | $R^b$ | $R^c$ | $R^d$ | $R^e$ | $R^f$ |
|---|---|---|---|---|---|---|---|
| 1337 | Z-s | H | Y-1 | Y-1 | Y-1 | H | Y-1 |
| 1338 | Z-s | H | Y-1 | Y-1 | Y-1 | Y-1 | H |
| 1339 | Z-s | H | Y-1 | Y-1 | Y-1 | Y-1 | Y-1 |
| 1340 | Z-s | Y-1 | H | H | H | H | H |
| 1341 | Z-s | Y-1 | H | H | H | H | Y-1 |
| 1342 | Z-s | Y-1 | H | H | H | Y-1 | H |
| 1343 | Z-s | Y-1 | H | H | H | Y-1 | Y-1 |
| 1344 | Z-s | Y-1 | H | H | Y-1 | H | H |
| 1345 | Z-s | Y-1 | H | H | Y-1 | H | Y-1 |
| 1346 | Z-s | Y-1 | H | H | Y-1 | Y-1 | H |
| 1347 | Z-s | Y-1 | H | H | Y-1 | Y-1 | Y-1 |
| 1348 | Z-s | Y-1 | H | Y-1 | H | H | H |
| 1349 | Z-s | Y-1 | H | Y-1 | H | H | Y-1 |
| 1350 | Z-s | Y-1 | H | Y-1 | H | Y-1 | H |
| 1351 | Z-s | Y-1 | H | Y-1 | H | Y-1 | Y-1 |
| 1352 | Z-s | Y-1 | H | Y-1 | Y-1 | H | H |
| 1353 | Z-s | Y-1 | H | Y-1 | Y-1 | H | Y-1 |
| 1354 | Z-s | Y-1 | H | Y-1 | Y-1 | Y-1 | H |
| 1355 | Z-s | Y-1 | H | Y-1 | Y-1 | Y-1 | Y-1 |
| 1356 | Z-s | Y-1 | Y-1 | H | H | H | H |
| 1357 | Z-s | Y-1 | Y-1 | H | H | H | Y-1 |
| 1358 | Z-s | Y-1 | Y-1 | H | H | Y-1 | H |
| 1359 | Z-s | Y-1 | Y-1 | H | H | Y-1 | Y-1 |
| 1360 | Z-s | Y-1 | Y-1 | H | Y-1 | H | H |
| 1361 | Z-s | Y-1 | Y-1 | H | Y-1 | H | Y-1 |
| 1362 | Z-s | Y-1 | Y-1 | H | Y-1 | Y-1 | H |
| 1363 | Z-s | Y-1 | Y-1 | H | Y-1 | Y-1 | Y-1 |
| 1364 | Z-s | Y-1 | Y-1 | Y-1 | H | H | H |
| 1365 | Z-s | Y-1 | Y-1 | Y-1 | H | H | Y-1 |
| 1366 | Z-s | Y-1 | Y-1 | Y-1 | H | Y-1 | H |
| 1367 | Z-s | Y-1 | Y-1 | Y-1 | H | Y-1 | Y-1 |
| 1368 | Z-s | Y-1 | Y-1 | Y-1 | Y-1 | H | H |
| 1369 | Z-s | Y-1 | Y-1 | Y-1 | Y-1 | H | Y-1 |
| 1370 | Z-s | Y-1 | Y-1 | Y-1 | Y-1 | Y-1 | H |
| 1371 | Z-s | Y-1 | Y-1 | Y-1 | Y-1 | Y-1 | Y-1 |
| 1372 | Z-s | H | H | H | H | H | Y-2 |
| 1373 | Z-s | H | H | H | H | Y-2 | H |
| 1374 | Z-s | H | H | H | H | Y-2 | Y-2 |
| 1375 | Z-s | H | H | H | Y-2 | H | H |
| 1376 | Z-s | H | H | H | Y-2 | H | Y-2 |
| 1377 | Z-s | H | H | H | Y-2 | Y-2 | H |
| 1378 | Z-s | H | H | H | Y-2 | Y-2 | Y-2 |
| 1379 | Z-s | H | H | Y-2 | H | H | H |
| 1380 | Z-s | H | H | Y-2 | H | H | Y-2 |
| 1381 | Z-s | H | H | Y-2 | H | Y-2 | H |
| 1382 | Z-s | H | H | Y-2 | H | Y-2 | Y-2 |
| 1383 | Z-s | H | H | Y-2 | Y-2 | H | H |
| 1384 | Z-s | H | H | Y-2 | Y-2 | H | Y-2 |
| 1385 | Z-s | H | H | Y-2 | Y-2 | Y-2 | H |
| 1386 | Z-s | H | H | Y-2 | Y-2 | Y-2 | Y-2 |
| 1387 | Z-s | H | Y-2 | H | H | H | H |
| 1388 | Z-s | H | Y-2 | H | H | H | Y-2 |
| 1389 | Z-s | H | Y-2 | H | H | Y-2 | H |
| 1390 | Z-s | H | Y-2 | H | H | Y-2 | Y-2 |
| 1391 | Z-s | H | Y-2 | H | Y-2 | H | H |
| 1392 | Z-s | H | Y-2 | H | Y-2 | H | Y-2 |
| 1393 | Z-s | H | Y-2 | H | Y-2 | Y-2 | H |
| 1394 | Z-s | H | Y-2 | H | Y-2 | Y-2 | Y-2 |
| 1395 | Z-s | H | Y-2 | Y-2 | H | H | H |
| 1396 | Z-s | H | Y-2 | Y-2 | H | H | Y-2 |
| 1397 | Z-s | H | Y-2 | Y-2 | H | Y-2 | H |
| 1398 | Z-s | H | Y-2 | Y-2 | H | Y-2 | Y-2 |
| 1399 | Z-s | H | Y-2 | Y-2 | Y-2 | H | H |
| 1400 | Z-s | H | Y-2 | Y-2 | Y-2 | H | Y-2 |
| 1401 | Z-s | H | Y-2 | Y-2 | Y-2 | Y-2 | H |
| 1402 | Z-s | H | Y-2 | Y-2 | Y-2 | Y-2 | Y-2 |
| 1403 | Z-s | Y-2 | H | H | H | H | H |
| 1404 | Z-s | Y-2 | H | H | H | H | Y-2 |
| 1405 | Z-s | Y-2 | H | H | H | Y-2 | H |
| 1406 | Z-s | Y-2 | H | H | H | Y-2 | Y-2 |
| 1407 | Z-s | Y-2 | H | H | Y-2 | H | H |
| 1408 | Z-s | Y-2 | H | H | Y-2 | H | Y-2 |
| 1409 | Z-s | Y-2 | H | H | Y-2 | Y-2 | H |
| 1410 | Z-s | Y-2 | H | H | Y-2 | Y-2 | Y-2 |
| 1411 | Z-s | Y-2 | H | Y-2 | H | H | H |
| 1412 | Z-s | Y-2 | H | Y-2 | H | H | Y-2 |
| 1413 | Z-s | Y-2 | H | Y-2 | H | Y-2 | H |
| 1414 | Z-s | Y-2 | H | Y-2 | H | Y-2 | Y-2 |
| 1415 | Z-s | Y-2 | H | Y-2 | Y-2 | H | H |
| 1416 | Z-s | Y-2 | H | Y-2 | Y-2 | H | Y-2 |
| 1417 | Z-s | Y-2 | H | Y-2 | Y-2 | Y-2 | H |
| 1418 | Z-s | Y-2 | H | Y-2 | Y-2 | Y-2 | Y-2 |
| 1419 | Z-s | Y-2 | Y-2 | H | H | H | H |
| 1420 | Z-s | Y-2 | Y-2 | H | H | H | Y-2 |
| 1421 | Z-s | Y-2 | Y-2 | H | H | Y-2 | H |
| 1422 | Z-s | Y-2 | Y-2 | H | H | Y-2 | Y-2 |
| 1423 | Z-s | Y-2 | Y-2 | H | Y-2 | H | H |
| 1424 | Z-s | Y-2 | Y-2 | H | Y-2 | H | Y-2 |
| 1425 | Z-s | Y-2 | Y-2 | H | Y-2 | Y-2 | H |
| 1426 | Z-s | Y-2 | Y-2 | H | Y-2 | Y-2 | Y-2 |
| 1427 | Z-s | Y-2 | Y-2 | Y-2 | H | H | H |
| 1428 | Z-s | Y-2 | Y-2 | Y-2 | H | H | Y-2 |
| 1429 | Z-s | Y-2 | Y-2 | Y-2 | H | Y-2 | H |
| 1430 | Z-s | Y-2 | Y-2 | Y-2 | H | Y-2 | Y-2 |
| 1431 | Z-s | Y-2 | Y-2 | Y-2 | Y-2 | H | H |
| 1432 | Z-s | Y-2 | Y-2 | Y-2 | Y-2 | H | Y-2 |
| 1433 | Z-s | Y-2 | Y-2 | Y-2 | Y-2 | Y-2 | H |
| 1434 | Z-s | Y-2 | Y-2 | Y-2 | Y-2 | Y-2 | Y-2 |
| 1435 | Z-s | H | H | H | H | H | Y-3 |
| 1436 | Z-s | H | H | H | H | Y-3 | H |
| 1437 | Z-s | H | H | H | H | Y-3 | Y-3 |
| 1438 | Z-s | H | H | H | Y-3 | H | H |
| 1439 | Z-s | H | H | H | Y-3 | H | Y-3 |
| 1440 | Z-s | H | H | H | Y-3 | Y-3 | H |
| 1441 | Z-s | H | H | H | Y-3 | Y-3 | Y-3 |
| 1442 | Z-s | H | H | Y-3 | H | H | H |
| 1443 | Z-s | H | H | Y-3 | H | H | Y-3 |
| 1444 | Z-s | H | H | Y-3 | H | Y-3 | H |
| 1445 | Z-s | H | H | Y-3 | H | Y-3 | Y-3 |
| 1446 | Z-s | H | H | Y-3 | Y-3 | H | H |
| 1447 | Z-s | H | H | Y-3 | Y-3 | H | Y-3 |
| 1448 | Z-s | H | H | Y-3 | Y-3 | Y-3 | H |
| 1449 | Z-s | H | H | Y-3 | Y-3 | Y-3 | Y-3 |
| 1450 | Z-s | H | Y-3 | H | H | H | H |
| 1451 | Z-s | H | Y-3 | H | H | H | Y-3 |
| 1452 | Z-s | H | Y-3 | H | H | Y-3 | H |
| 1453 | Z-s | H | Y-3 | H | H | Y-3 | Y-3 |
| 1454 | Z-s | H | Y-3 | H | Y-3 | H | H |
| 1455 | Z-s | H | Y-3 | H | Y-3 | H | Y-3 |
| 1456 | Z-s | H | Y-3 | H | Y-3 | Y-3 | H |
| 1457 | Z-s | H | Y-3 | H | Y-3 | Y-3 | Y-3 |
| 1458 | Z-s | H | Y-3 | Y-3 | H | H | H |
| 1459 | Z-s | H | Y-3 | Y-3 | H | H | Y-3 |
| 1460 | Z-s | H | Y-3 | Y-3 | H | Y-3 | H |
| 1461 | Z-s | H | Y-3 | Y-3 | H | Y-3 | Y-3 |
| 1462 | Z-s | H | Y-3 | Y-3 | Y-3 | H | H |
| 1463 | Z-s | H | Y-3 | Y-3 | Y-3 | H | Y-3 |
| 1464 | Z-s | H | Y-3 | Y-3 | Y-3 | Y-3 | H |
| 1465 | Z-s | H | Y-3 | Y-3 | Y-3 | Y-3 | Y-3 |
| 1466 | Z-s | Y-3 | H | H | H | H | H |
| 1467 | Z-s | Y-3 | H | H | H | H | Y-3 |
| 1468 | Z-s | Y-3 | H | H | H | Y-3 | H |
| 1469 | Z-s | Y-3 | H | H | H | Y-3 | Y-3 |
| 1470 | Z-s | Y-3 | H | H | Y-3 | H | H |
| 1471 | Z-s | Y-3 | H | H | Y-3 | H | Y-3 |
| 1472 | Z-s | Y-3 | H | H | Y-3 | Y-3 | H |
| 1473 | Z-s | Y-3 | H | H | Y-3 | Y-3 | Y-3 |
| 1474 | Z-s | Y-3 | H | Y-3 | H | H | H |
| 1475 | Z-s | Y-3 | H | Y-3 | H | H | Y-3 |
| 1476 | Z-s | Y-3 | H | Y-3 | H | Y-3 | H |
| 1477 | Z-s | Y-3 | H | Y-3 | H | Y-3 | Y-3 |
| 1478 | Z-s | Y-3 | H | Y-3 | Y-3 | H | H |
| 1479 | Z-s | Y-3 | H | Y-3 | Y-3 | H | Y-3 |
| 1480 | Z-s | Y-3 | H | Y-3 | Y-3 | Y-3 | H |
| 1481 | Z-s | Y-3 | H | Y-3 | Y-3 | Y-3 | Y-3 |
| 1482 | Z-s | Y-3 | Y-3 | H | H | H | H |
| 1483 | Z-s | Y-3 | Y-3 | H | H | H | Y-3 |
| 1484 | Z-s | Y-3 | Y-3 | H | H | Y-3 | H |
| 1485 | Z-s | Y-3 | Y-3 | H | H | Y-3 | Y-3 |
| 1486 | Z-s | Y-3 | Y-3 | H | Y-3 | H | H |
| 1487 | Z-s | Y-3 | Y-3 | H | Y-3 | H | Y-3 |
| 1488 | Z-s | Y-3 | Y-3 | H | Y-3 | Y-3 | H |
| 1489 | Z-s | Y-3 | Y-3 | H | Y-3 | Y-3 | Y-3 |
| 1490 | Z-s | Y-3 | Y-3 | Y-3 | H | H | H |

| No. | Z | $R^a$ | $R^b$ | $R^c$ | $R^d$ | $R^e$ | $R^f$ |
|---|---|---|---|---|---|---|---|
| 1491 | Z-s | Y-3 | Y-3 | Y-3 | H | H | Y-3 |
| 1492 | Z-s | Y-3 | Y-3 | Y-3 | H | Y-3 | H |
| 1493 | Z-s | Y-3 | Y-3 | Y-3 | H | Y-3 | Y-3 |
| 1494 | Z-s | Y-3 | Y-3 | Y-3 | Y-3 | H | H |
| 1495 | Z-s | Y-3 | Y-3 | Y-3 | Y-3 | H | Y-3 |
| 1496 | Z-s | Y-3 | Y-3 | Y-3 | Y-3 | Y-3 | H |
| 1497 | Z-s | Y-3 | Y-3 | Y-3 | Y-3 | Y-3 | Y-3 |
| 1498 | Z-t | H | H | H | Y-1 | — | — |
| 1499 | Z-t | H | H | Y-1 | H | — | — |
| 1500 | Z-t | H | H | Y-1 | Y-1 | — | — |
| 1501 | Z-t | H | Y-1 | H | H | — | — |
| 1502 | Z-t | H | Y-1 | H | Y-1 | — | — |
| 1503 | Z-t | H | Y-1 | Y-1 | H | — | — |
| 1504 | Z-t | H | Y-1 | Y-1 | Y-1 | — | — |
| 1505 | Z-t | Y-1 | H | H | H | — | — |
| 1506 | Z-t | Y-1 | H | H | Y-1 | — | — |
| 1507 | Z-t | Y-1 | H | Y-1 | H | — | — |
| 1508 | Z-t | Y-1 | H | Y-1 | Y-1 | — | — |
| 1509 | Z-t | Y-1 | Y-1 | H | H | — | — |
| 1510 | Z-t | Y-1 | Y-1 | H | Y-1 | — | — |
| 1511 | Z-t | Y-1 | Y-1 | Y-1 | H | — | — |
| 1512 | Z-t | Y-1 | Y-1 | Y-1 | Y-1 | — | — |
| 1513 | Z-t | H | H | H | Y-2 | — | — |
| 1514 | Z-t | H | H | Y-2 | H | — | — |
| 1515 | Z-t | H | H | Y-2 | Y-2 | — | — |
| 1516 | Z-t | H | Y-2 | H | H | — | — |
| 1517 | Z-t | H | Y-2 | H | Y-2 | — | — |
| 1518 | Z-t | H | Y-2 | Y-2 | H | — | — |
| 1519 | Z-t | H | Y-2 | Y-2 | Y-2 | — | — |
| 1520 | Z-t | Y-2 | H | H | H | — | — |
| 1521 | Z-t | Y-2 | H | H | Y-2 | — | — |
| 1522 | Z-t | Y-2 | H | Y-2 | H | — | — |
| 1523 | Z-t | Y-2 | H | Y-2 | Y-2 | — | — |
| 1524 | Z-t | Y-2 | Y-2 | H | H | — | — |
| 1525 | Z-t | Y-2 | Y-2 | H | Y-2 | — | — |
| 1526 | Z-t | Y-2 | Y-2 | Y-2 | H | — | — |
| 1527 | Z-t | Y-2 | Y-2 | Y-2 | Y-2 | — | — |
| 1528 | Z-t | H | H | H | Y-3 | — | — |
| 1529 | Z-t | H | H | Y-3 | H | — | — |
| 1530 | Z-t | H | H | Y-3 | Y-3 | — | — |
| 1531 | Z-t | H | Y-3 | H | H | — | — |
| 1532 | Z-t | H | Y-3 | H | Y-3 | — | — |
| 1533 | Z-t | H | Y-3 | Y-3 | H | — | — |
| 1534 | Z-t | H | Y-3 | Y-3 | Y-3 | — | — |
| 1535 | Z-t | Y-3 | H | H | H | — | — |
| 1536 | Z-t | Y-3 | H | H | Y-3 | — | — |
| 1537 | Z-t | Y-3 | H | Y-3 | H | — | — |
| 1538 | Z-t | Y-3 | H | Y-3 | Y-3 | — | — |
| 1539 | Z-t | Y-3 | Y-3 | H | H | — | — |
| 1540 | Z-t | Y-3 | Y-3 | H | Y-3 | — | — |
| 1541 | Z-t | Y-3 | Y-3 | Y-3 | H | — | — |
| 1542 | Z-t | Y-3 | Y-3 | Y-3 | Y-3 | — | — |
| 1543 | Z-u | H | H | Y-1 | — | — | — |
| 1544 | Z-u | H | H | Y-2 | — | — | — |
| 1545 | Z-u | H | H | Y-3 | — | — | — |
| 1546 | Z-u | H | Y-1 | H | — | — | — |
| 1547 | Z-u | H | Y-1 | Y-1 | — | — | — |
| 1548 | Z-u | H | Y-1 | Y-2 | — | — | — |
| 1549 | Z-u | H | Y-1 | Y-3 | — | — | — |
| 1550 | Z-u | H | Y-2 | H | — | — | — |
| 1551 | Z-u | H | Y-2 | Y-1 | — | — | — |
| 1552 | Z-u | H | Y-2 | Y-2 | — | — | — |
| 1553 | Z-u | H | Y-2 | Y-3 | — | — | — |
| 1554 | Z-u | H | Y-3 | H | — | — | — |
| 1555 | Z-u | H | Y-3 | Y-1 | — | — | — |
| 1556 | Z-u | H | Y-3 | Y-2 | — | — | — |
| 1557 | Z-u | H | Y-3 | Y-3 | — | — | — |
| 1558 | Z-u | Y-1 | H | H | — | — | — |
| 1559 | Z-u | Y-1 | H | Y-1 | — | — | — |
| 1560 | Z-u | Y-1 | H | Y-2 | — | — | — |
| 1561 | Z-u | Y-1 | H | Y-3 | — | — | — |
| 1562 | Z-u | Y-1 | Y-1 | H | — | — | — |
| 1563 | Z-u | Y-1 | Y-1 | Y-1 | — | — | — |
| 1564 | Z-u | Y-1 | Y-1 | Y-2 | — | — | — |
| 1565 | Z-u | Y-1 | Y-1 | Y-3 | — | — | — |
| 1566 | Z-u | Y-1 | Y-2 | H | — | — | — |
| 1567 | Z-u | Y-1 | Y-2 | Y-1 | — | — | — |
| 1568 | Z-u | Y-1 | Y-2 | Y-2 | — | — | — |
| 1569 | Z-u | Y-1 | Y-2 | Y-3 | — | — | — |
| 1570 | Z-u | Y-1 | Y-3 | H | — | — | — |
| 1571 | Z-u | Y-1 | Y-3 | Y-1 | — | — | — |
| 1572 | Z-u | Y-1 | Y-3 | Y-2 | — | — | — |
| 1573 | Z-u | Y-1 | Y-3 | Y-3 | — | — | — |
| 1574 | Z-u | Y-2 | H | H | — | — | — |
| 1575 | Z-u | Y-2 | H | Y-1 | — | — | — |
| 1576 | Z-u | Y-2 | H | Y-2 | — | — | — |
| 1577 | Z-u | Y-2 | H | Y-3 | — | — | — |
| 1578 | Z-u | Y-2 | Y-1 | H | — | — | — |
| 1579 | Z-u | Y-2 | Y-1 | Y-1 | — | — | — |
| 1580 | Z-u | Y-2 | Y-1 | Y-2 | — | — | — |
| 1581 | Z-u | Y-2 | Y-1 | Y-3 | — | — | — |
| 1582 | Z-u | Y-2 | Y-2 | H | — | — | — |
| 1583 | Z-u | Y-2 | Y-2 | Y-1 | — | — | — |
| 1584 | Z-u | Y-2 | Y-2 | Y-2 | — | — | — |
| 1585 | Z-u | Y-2 | Y-2 | Y-3 | — | — | — |
| 1586 | Z-u | Y-2 | Y-3 | H | — | — | — |
| 1587 | Z-u | Y-2 | Y-3 | Y-1 | — | — | — |
| 1588 | Z-u | Y-2 | Y-3 | Y-2 | — | — | — |
| 1589 | Z-u | Y-2 | Y-3 | Y-3 | — | — | — |
| 1590 | Z-u | Y-3 | H | H | — | — | — |
| 1591 | Z-u | Y-3 | H | Y-1 | — | — | — |
| 1592 | Z-u | Y-3 | H | Y-2 | — | — | — |
| 1593 | Z-u | Y-3 | H | Y-3 | — | — | — |
| 1594 | Z-u | Y-3 | Y-1 | H | — | — | — |
| 1595 | Z-u | Y-3 | Y-1 | Y-1 | — | — | — |
| 1596 | Z-u | Y-3 | Y-1 | Y-2 | — | — | — |
| 1597 | Z-u | Y-3 | Y-1 | Y-3 | — | — | — |
| 1598 | Z-u | Y-3 | Y-2 | H | — | — | — |
| 1599 | Z-u | Y-3 | Y-2 | Y-1 | — | — | — |
| 1600 | Z-u | Y-3 | Y-2 | Y-2 | — | — | — |
| 1601 | Z-u | Y-3 | Y-2 | Y-3 | — | — | — |
| 1602 | Z-u | Y-3 | Y-3 | H | — | — | — |
| 1603 | Z-u | Y-3 | Y-3 | Y-1 | — | — | — |
| 1604 | Z-u | Y-3 | Y-3 | Y-2 | — | — | — |
| 1605 | Z-u | Y-3 | Y-3 | Y-3 | — | — | — |

The compounds according to the invention can be prepared by means of organochemical synthesis processes known to the person skilled in the art.

Illustrative synthetic routes which give rise to some important structural classes of the compounds according to the invention will be depicted below. However, the person skilled in the art is not tied to these examples, but instead can also prepare the compounds according to the invention with the aid of other reactions of preparative organic chemistry and by other reaction routes, without an inventive step.

Scheme 1 illustrates a typical synthetic route for the preparation of compounds according to the invention which are substituted by a perdeuterated phenyl group as group Y. This route starts from $d^6$-benzene, which is brominated, converted into a boronic acid derivative and subsequently reacted with a group Z (here benzanthracene) in a cross-coupling reaction.

Scheme 1

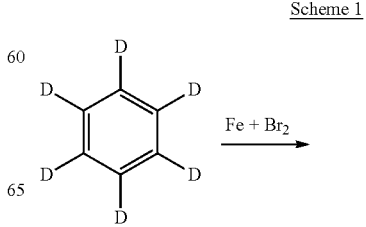

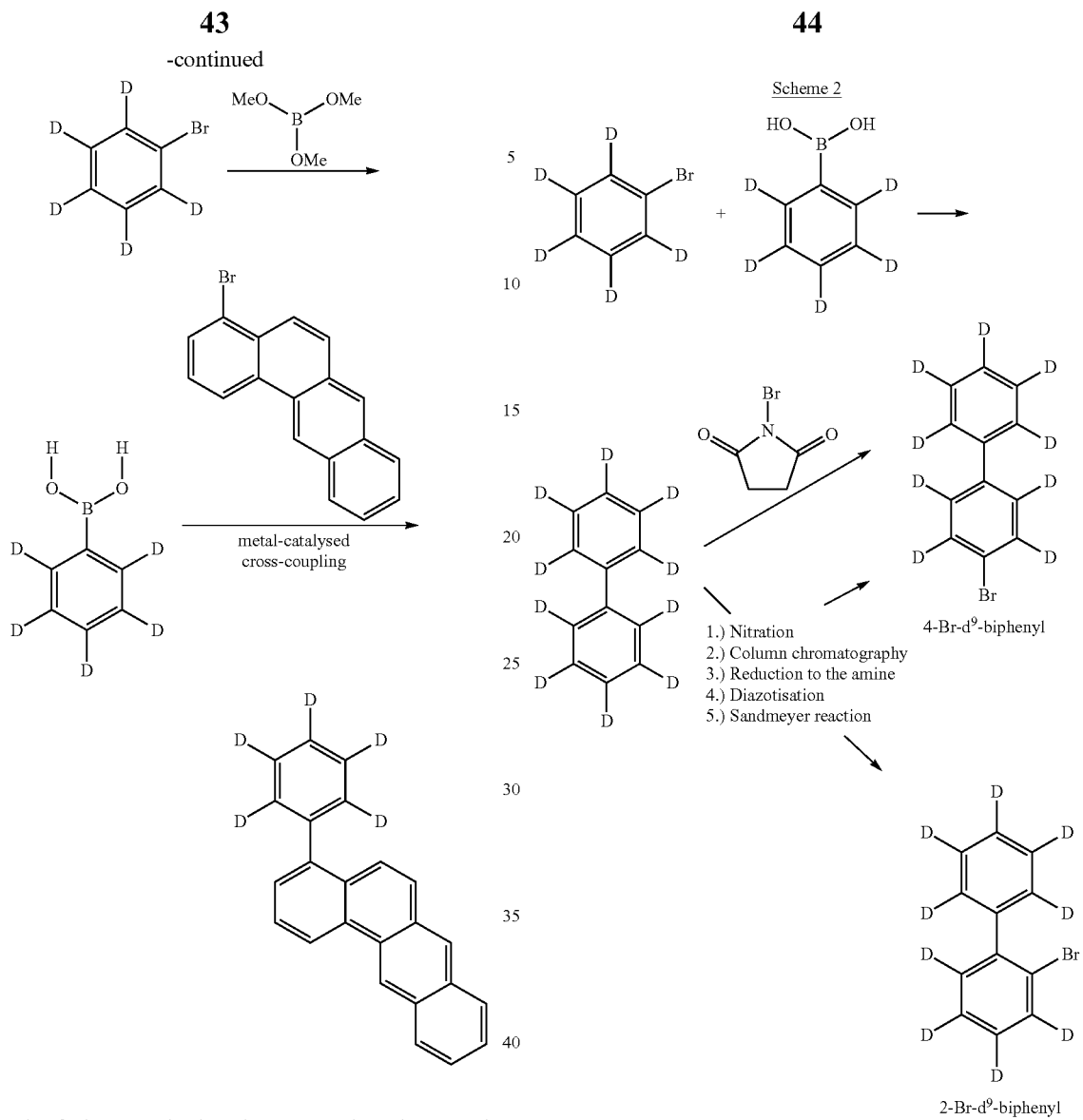

Instead of deuterated phenyl, many other deuterated groups Y can be introduced by a similar route. As an example, Scheme 2 depicts the preparation of perdeuterated biphenyl, which can be brominated at various positions (2- and 4-position shown here).

Scheme 3 shows the synthesis of partially deuterated biphenyl derivatives starting from boronic acid-substituted $d^5$-benzene (preparation analogous to Scheme 1).

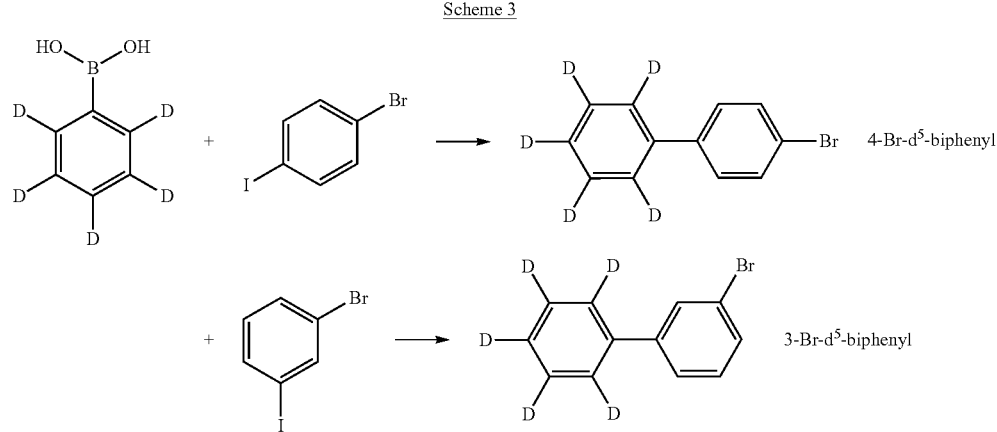

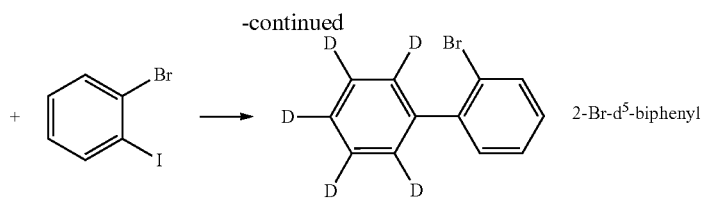

2-Br-d⁵-biphenyl

The synthesis of other deuterated groups, in particular deuterated heteroaromatic groups, is described, for example, in the application WO 2009/096555.

These groups can, as shown by way of example in Scheme 1, be reacted with the aromatic or heteroaromatic backbones Z by an organometallic cross-coupling reaction, for example a Suzuki coupling, with Pd catalysis, where the compounds of the formula (I) according to the invention or precursors of these compounds are obtained.

Two syntheses of compounds of the formula (I) according to the invention will be shown below (Schemes 4 and 5).

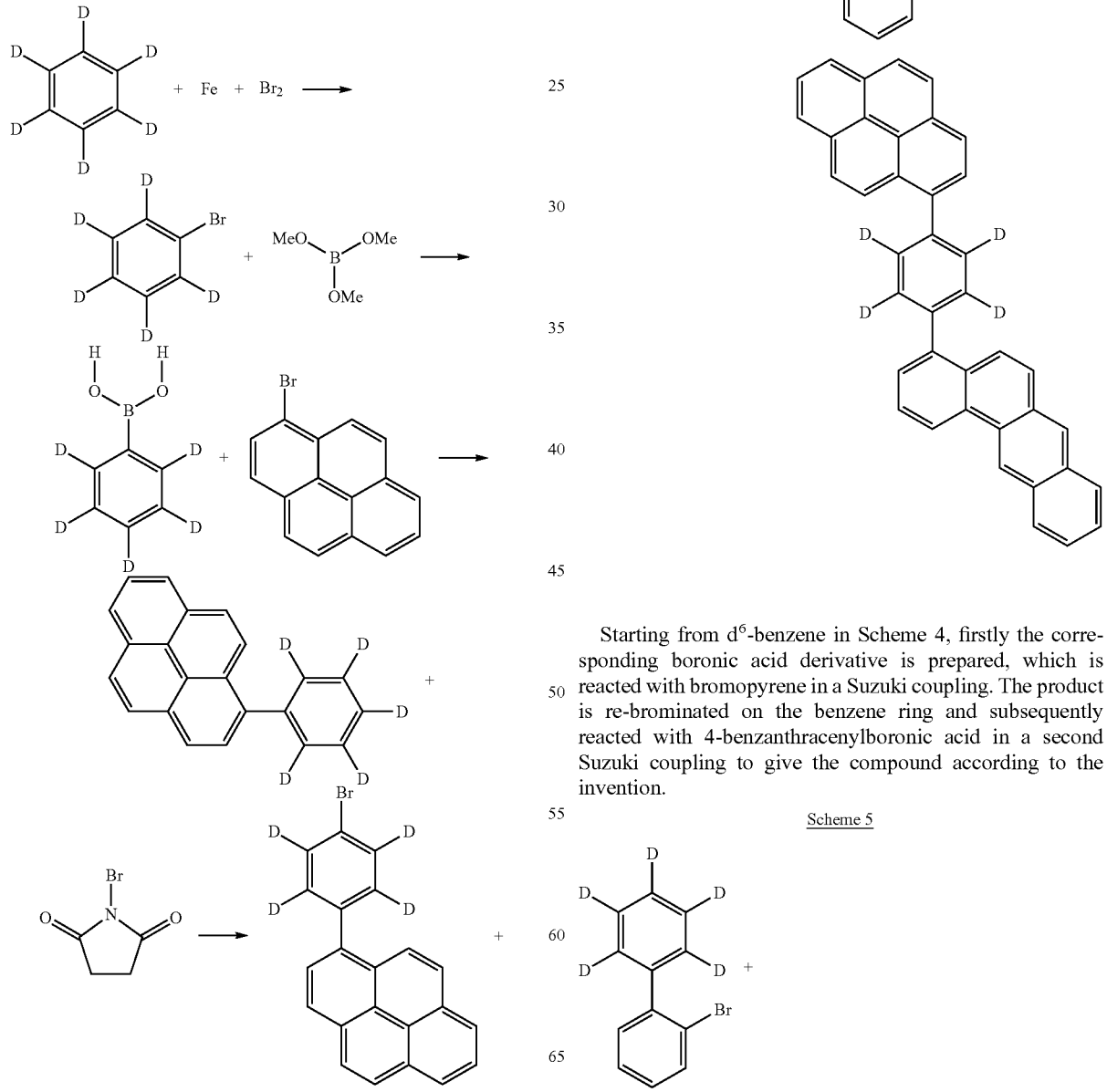

Starting from $d^6$-benzene in Scheme 4, firstly the corresponding boronic acid derivative is prepared, which is reacted with bromopyrene in a Suzuki coupling. The product is re-brominated on the benzene ring and subsequently reacted with 4-benzanthracenylboronic acid in a second Suzuki coupling to give the compound according to the invention.

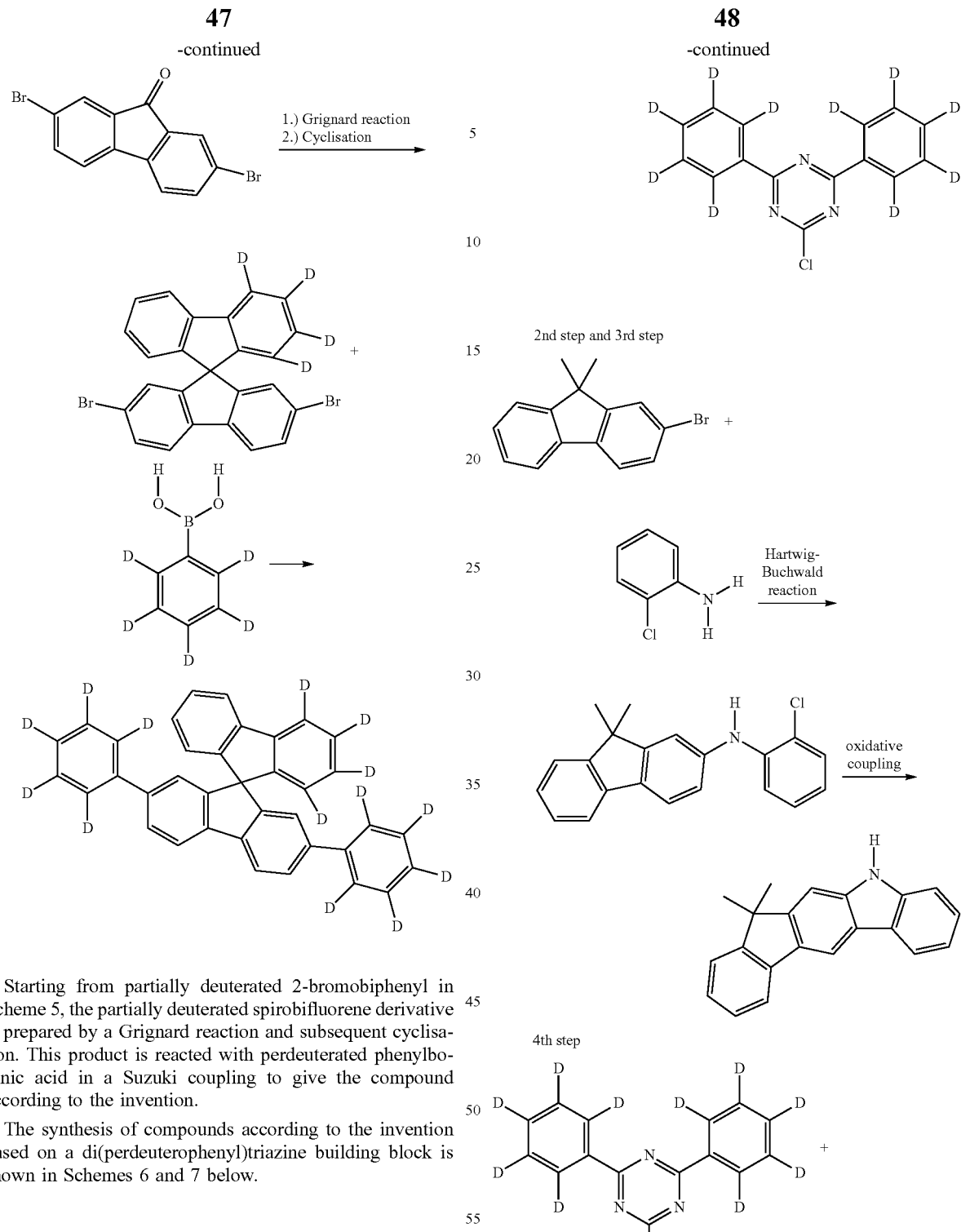

Starting from partially deuterated 2-bromobiphenyl in Scheme 5, the partially deuterated spirobifluorene derivative is prepared by a Grignard reaction and subsequent cyclisation. This product is reacted with perdeuterated phenylboronic acid in a Suzuki coupling to give the compound according to the invention.

The synthesis of compounds according to the invention based on a di(perdeuterophenyl)triazine building block is shown in Schemes 6 and 7 below.

Scheme 6

1st step

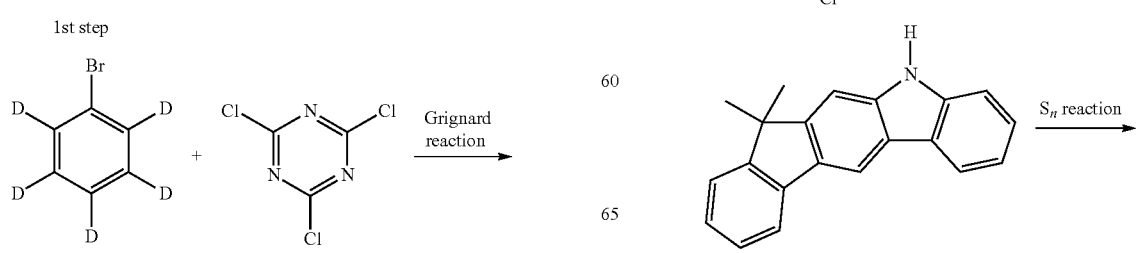

49

-continued

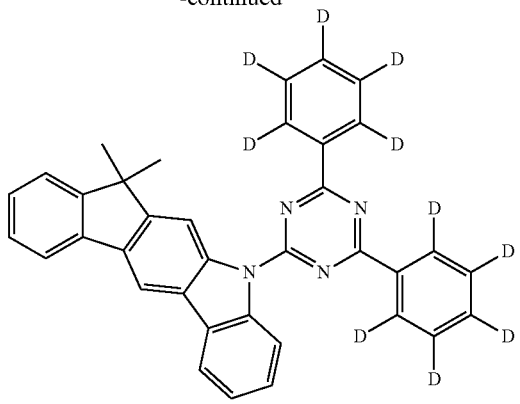

Starting from perdeuterated bromobenzene, firstly perdeuterated di(perdeuterophenyl)triazine is prepared via a Grignard reaction in Scheme 6. In a two-step sequence, the 2$^{nd}$ synthone is prepared from 2-bromodimethyl-fluorene by means of a Hartwig-Buchwald reaction with 2-chloroaniline and subsequent oxidative coupling. This 2nd synthone is reacted with the di(perdeuterophenyl)triazine in an $S_n$ reaction to give the compound according to the invention.

Scheme 7

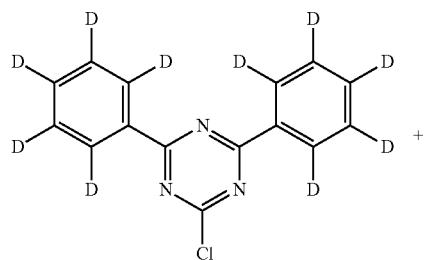

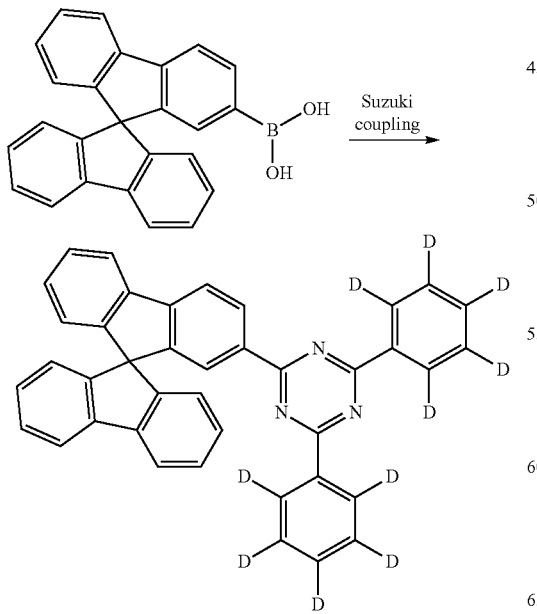

50

Perdeuterated di(perdeuterophenyl)triazine prepared analogously via a Grignard reaction as in Scheme 6 reacts in Scheme 7 with spiro-2-boronic acid in a Suzuki coupling to give the compound according to the invention.

The invention thus also relates to a process for the preparation of the compounds according to the invention, characterised in that one or more groups Y are linked to the group Z via an organometallic coupling reaction. Synthetically readily accessible perdeuterated or partially deuterated starting compounds are preferably used here, as depicted in Schemes 1 to 3 above. The starting materials used here are particularly preferably the aromatic or heteroaromatic compounds d$^6$-benzene, d$^8$-toluene or d$^5$-pyridine.

Besides the pure compounds, the invention also relates to mixtures.

The said mixtures comprise compounds of the formula (I)

Z—(Y)$_n$     formula (I), where Z, Y and n are as defined above, and at least one emitter compound.

The preferred embodiments mentioned above, in particular with respect to the groups Z, Y, the index n and the radicals R and R$^1$, apply to the compounds of the formula (I) in mixtures with emitter compounds.

The compounds of the formula (I) preferably represent host materials in the mixtures.

It is particularly preferred here for the compounds of the formula (I) to make up more than 50% by volume of the mixture, very particularly preferably more than 85% by volume of the mixture.

Examples of compounds of the formula (I) are shown below. The compounds shown are preferably employed in mixtures with emitter compounds, particularly preferably as host materials.

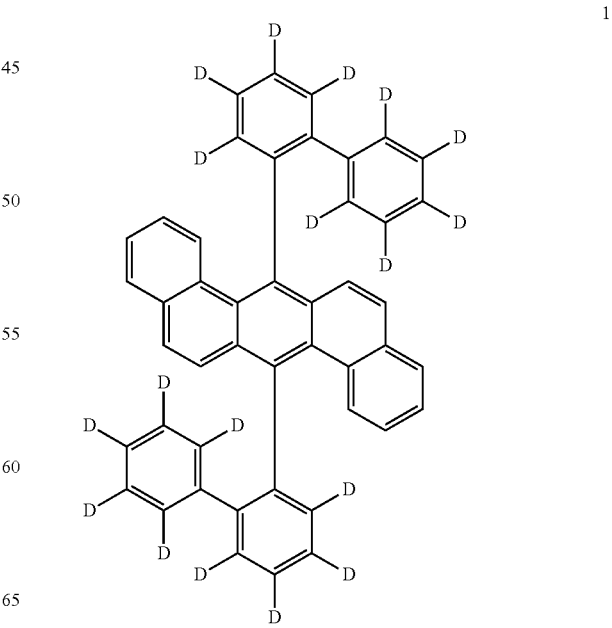

1

-continued
2
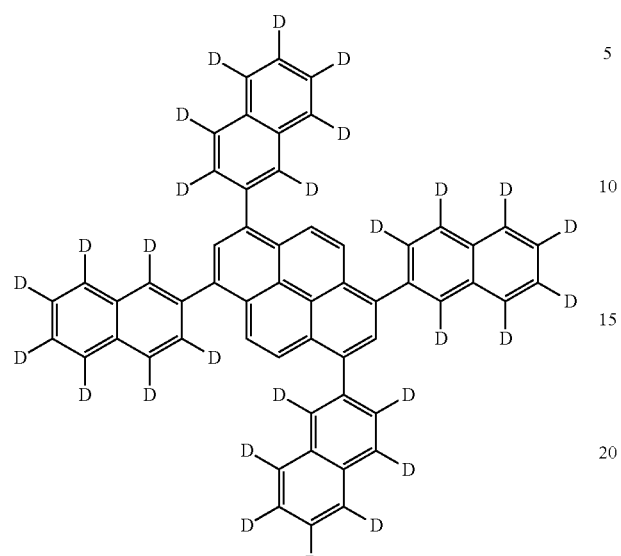
3
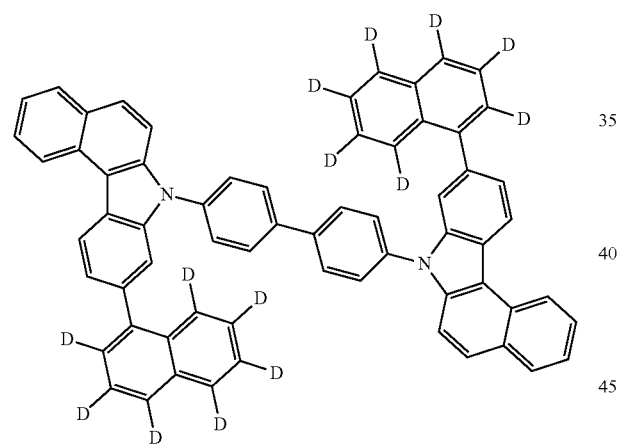
4
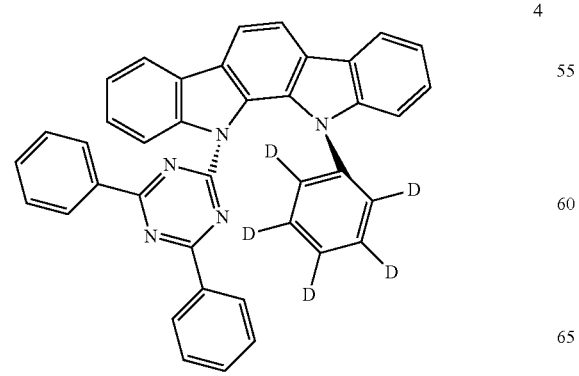
-continued
5
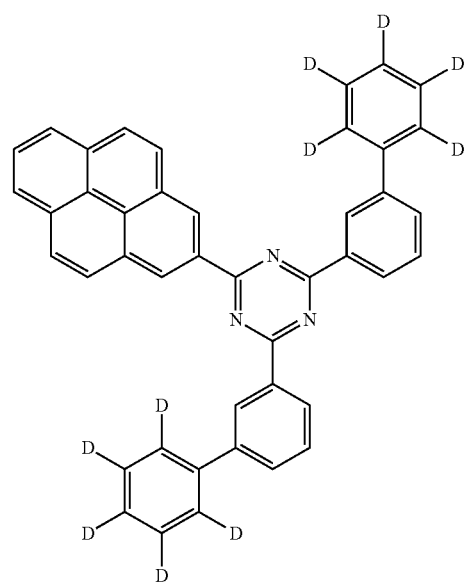
6
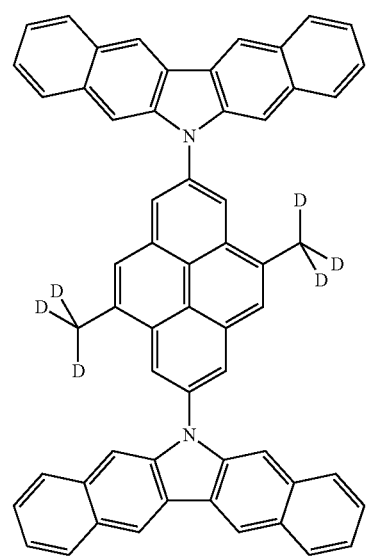
7
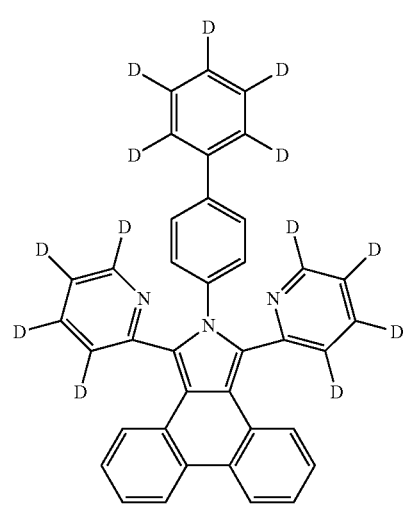

8
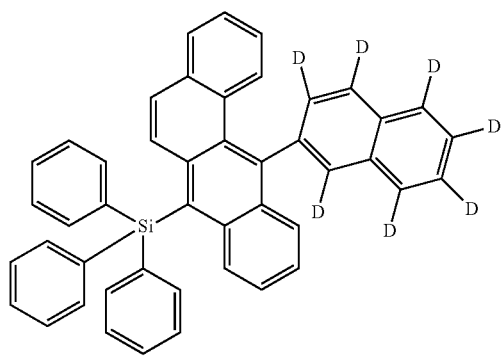
9
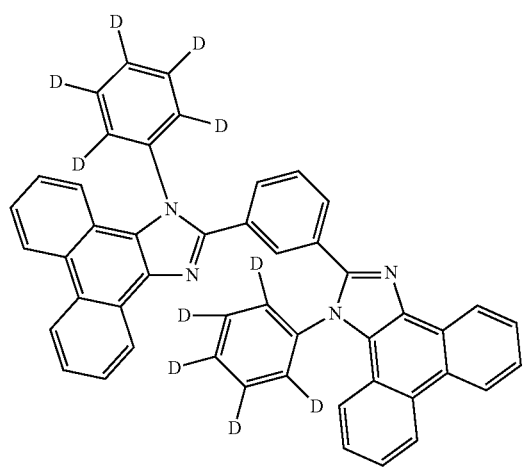
10
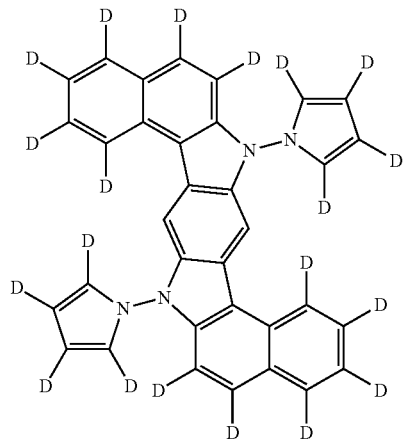
11
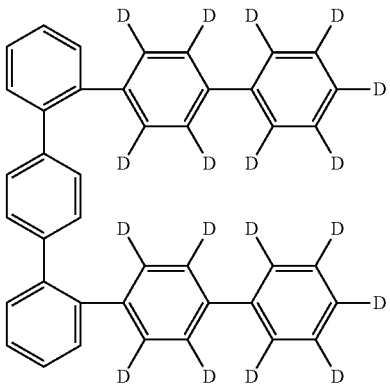
12
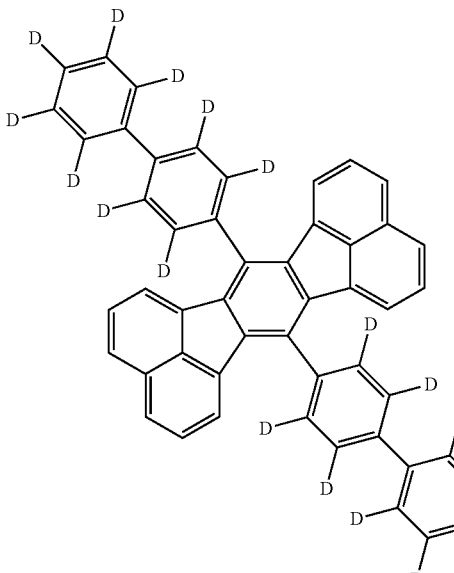
13
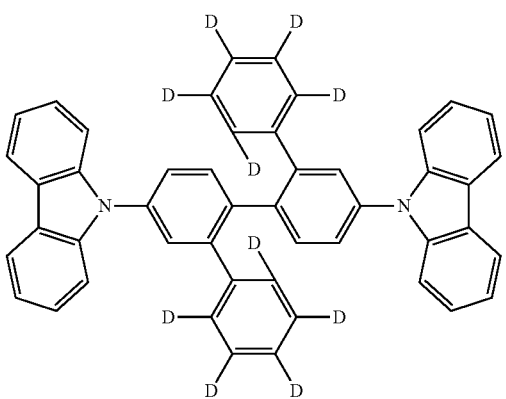

14
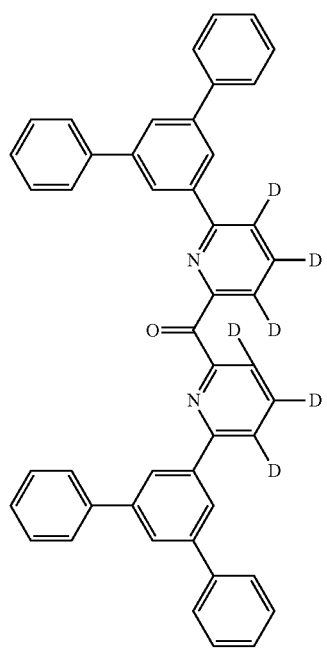
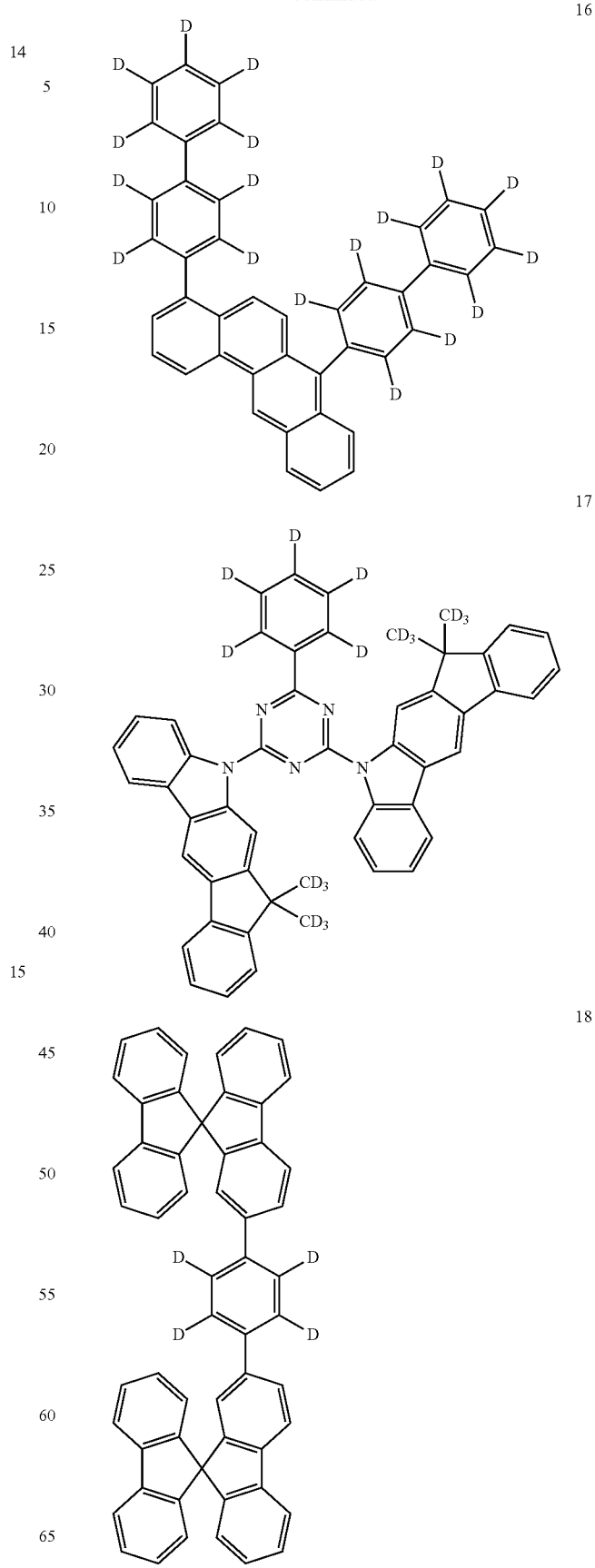

19
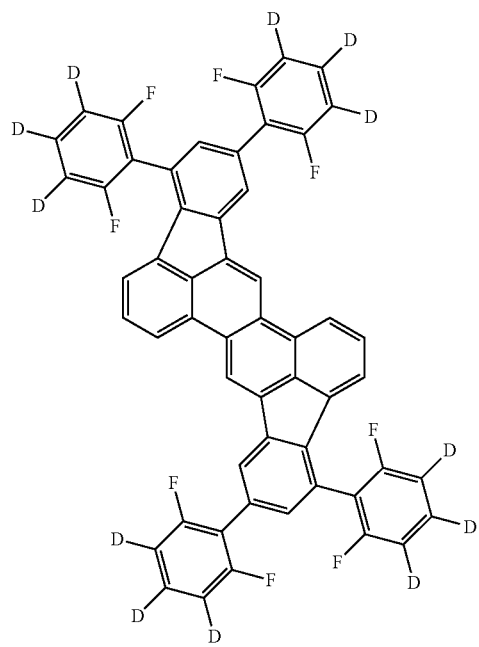
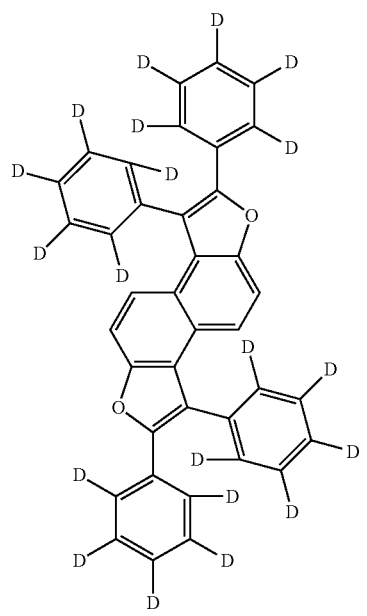
21
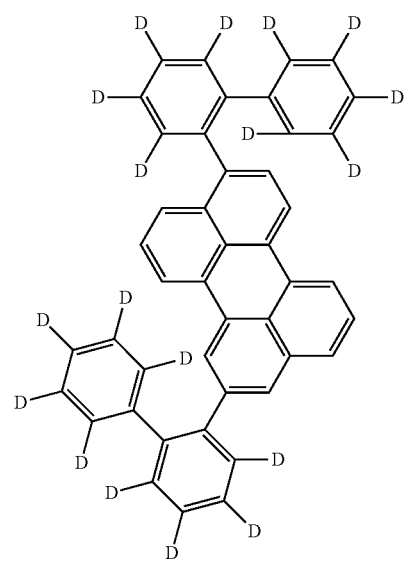
22
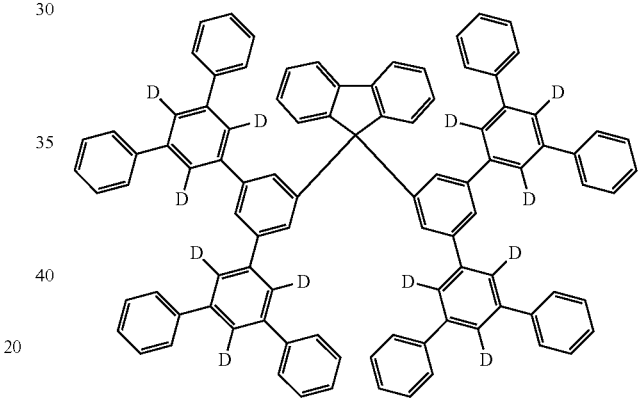
23
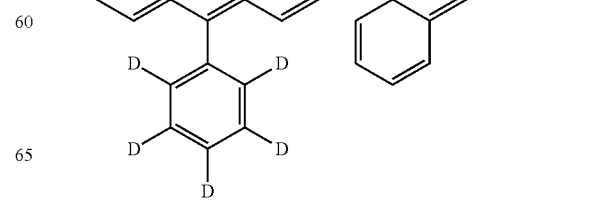

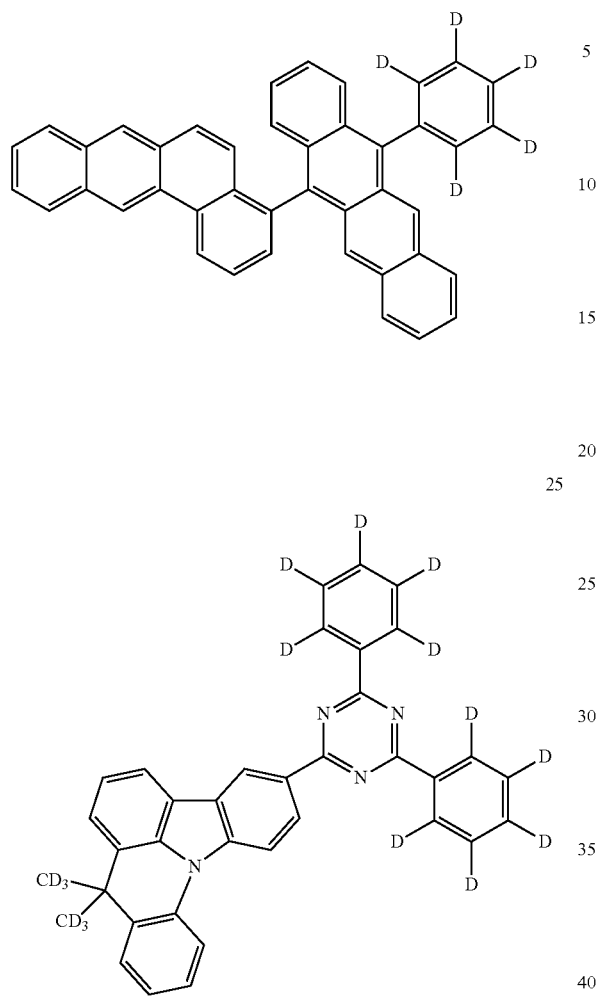
24
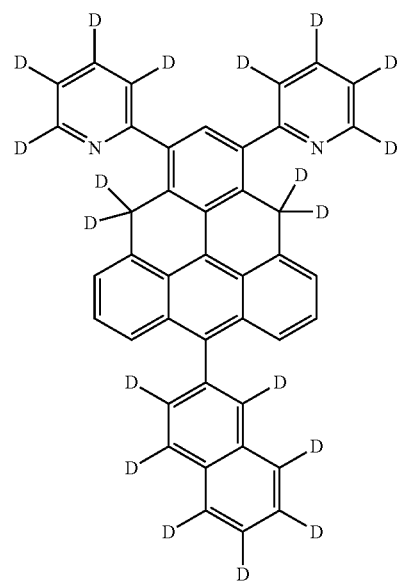
27
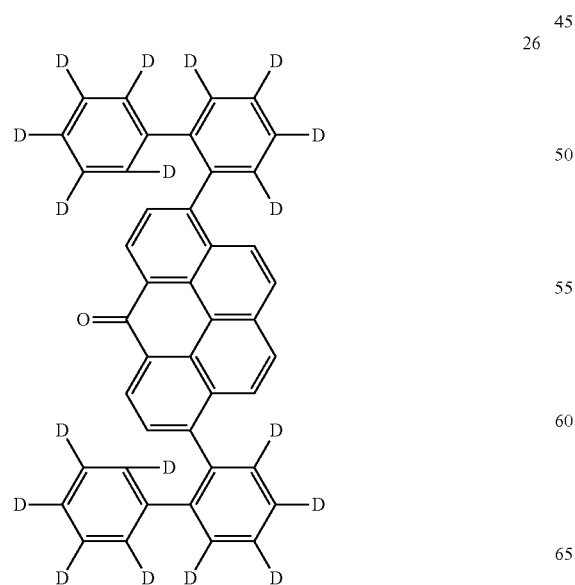
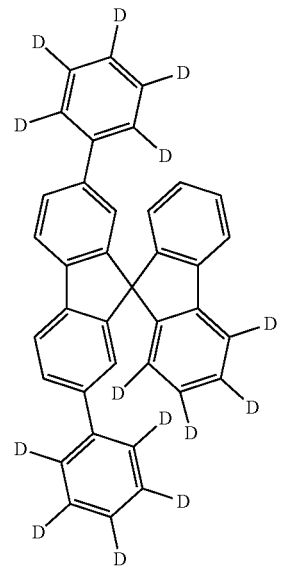

29
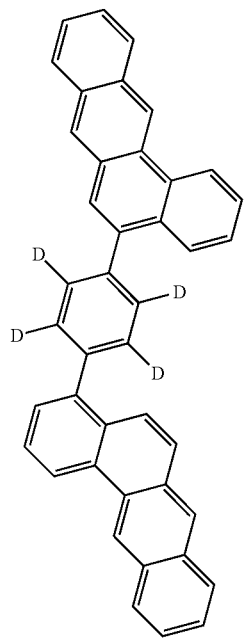
30
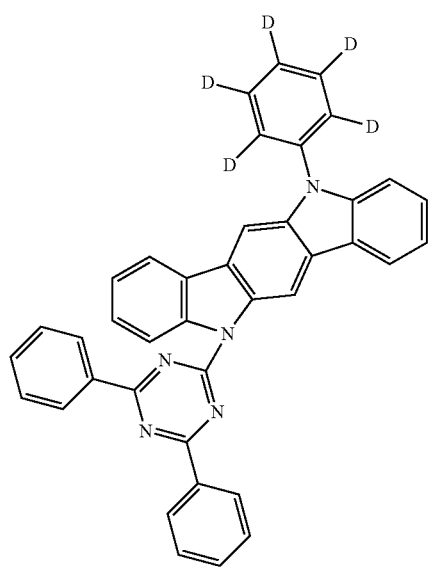
31
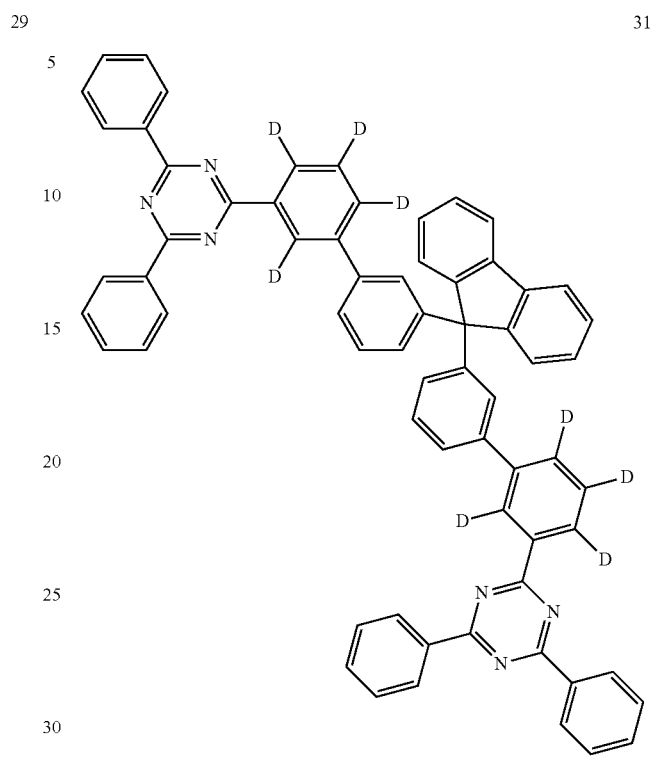
32
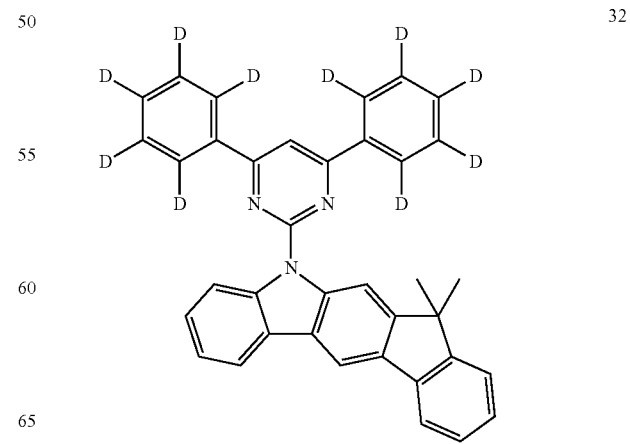

33
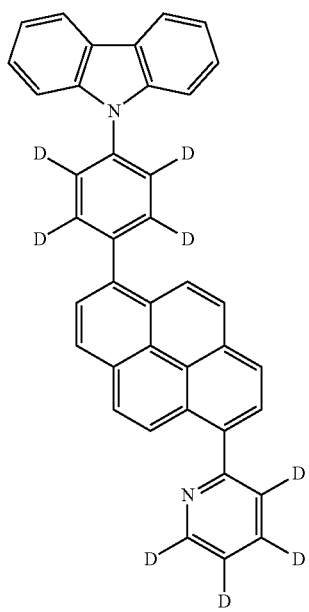
34
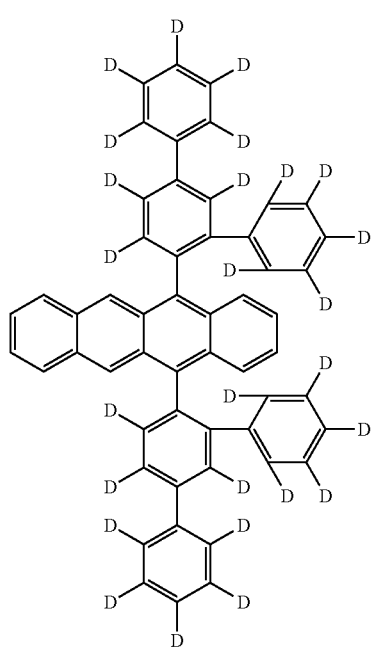
35
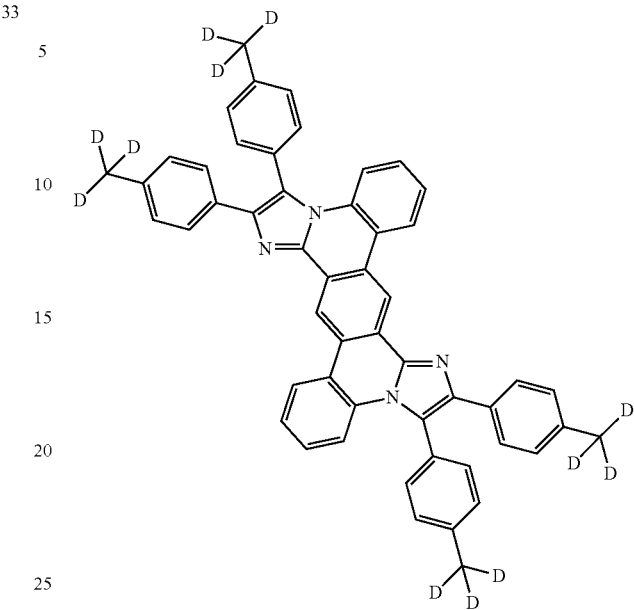
36
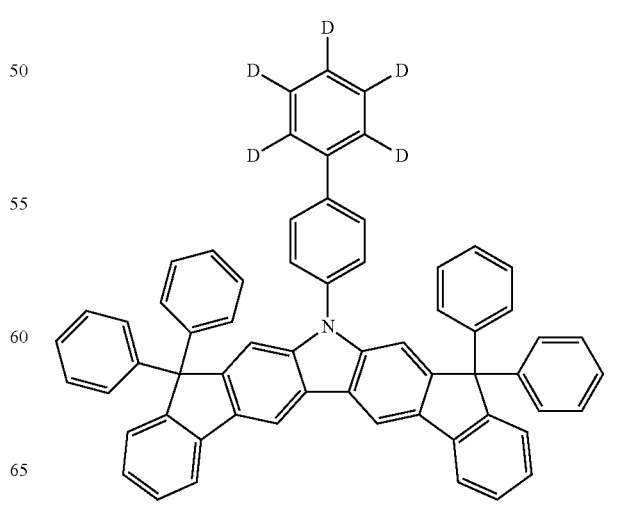
37

-continued
38
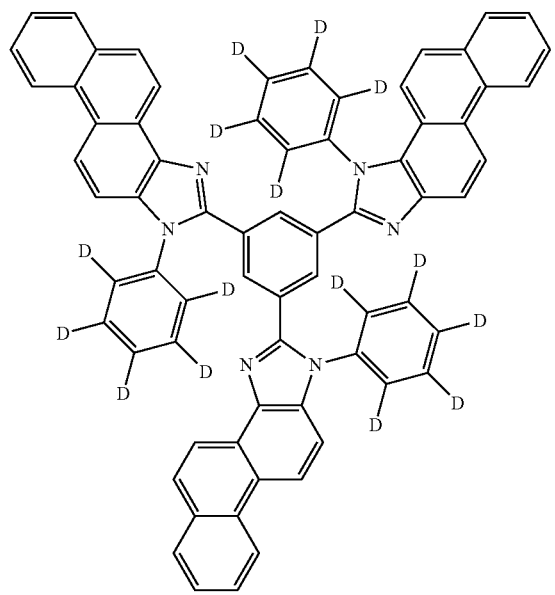
39
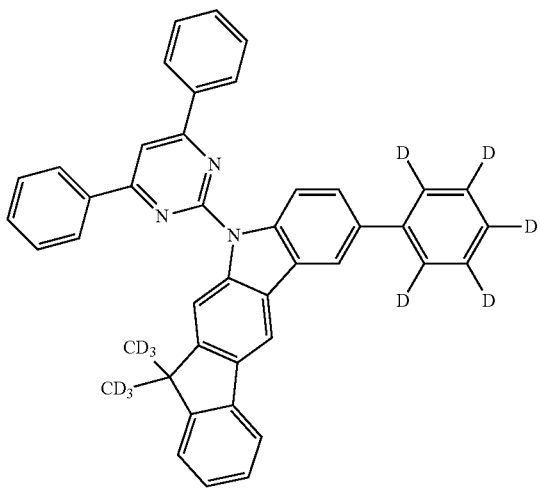
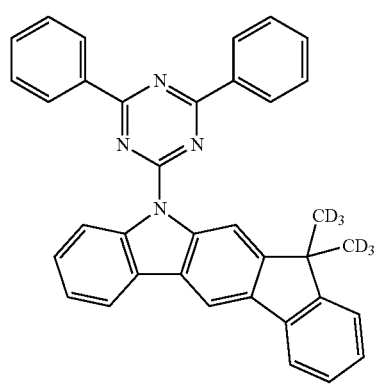
-continued
41
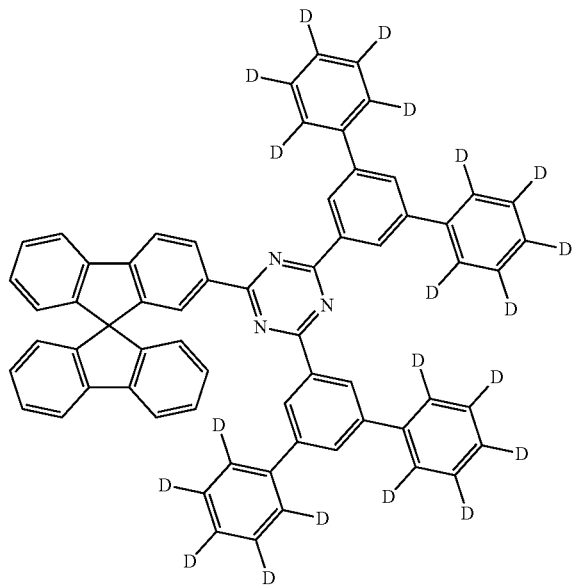
42
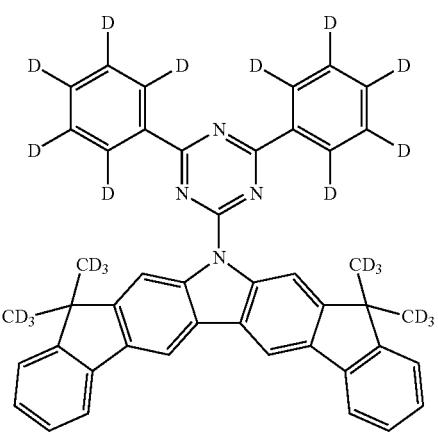
43
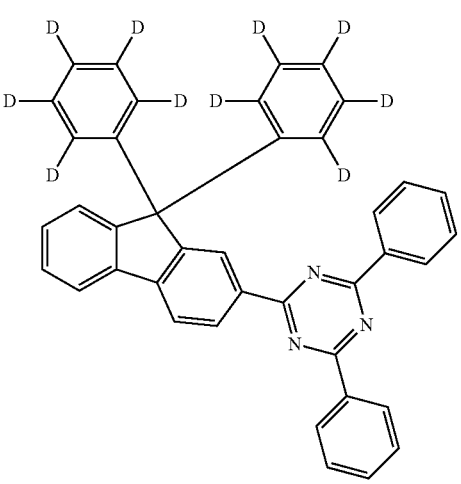

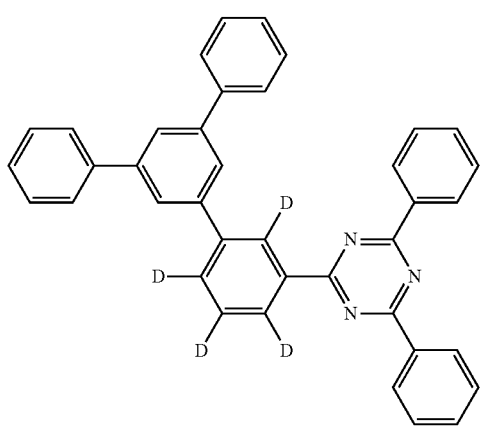

44

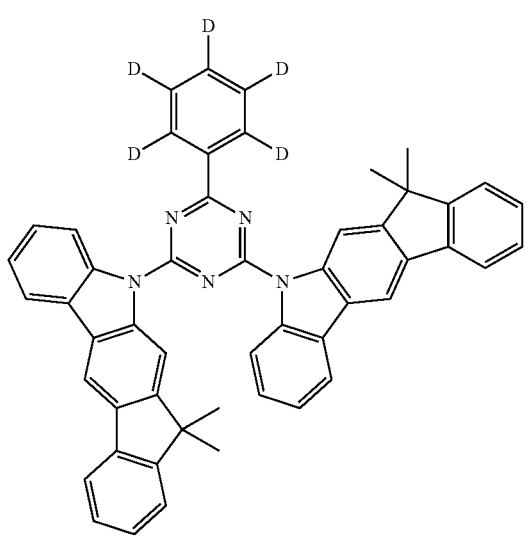

45

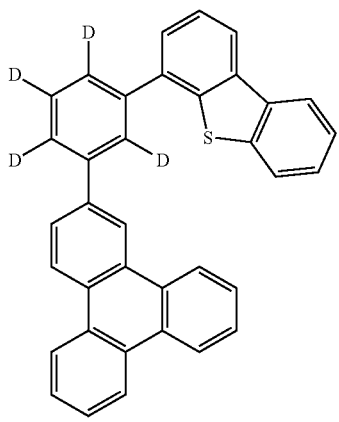

46

Besides compounds of the formula (I), the mixtures according to the invention preferably comprise one or more fluorescent emitter compounds (dopants).

A fluorescent compound in the sense of this invention is a compound which exhibits luminescence from an excited singlet state at room temperature. For the purposes of this invention, all luminescent compounds which contain no heavy atoms, i.e. no atoms having an atomic number greater than 36, in particular, are to be regarded as fluorescent compounds.

The mixture according to the invention particularly preferably comprises at least one fluorescent emitter compound which represents an aromatic or heteroaromatic ring system having 5 to 60 aromatic ring atoms, which may be substituted by one or more substituents $R^3$, where $R^3$, identically or differently on each occurrence, represents H, D, F, Cl, Br, I, CN, $N(R^4)_2$, $N(Ar)_2$, $NO_2$, $Si(R^4)_3$ or a straight-chain alkyl, alkoxy or thioalkoxy group having 1 to 40 C atoms or an alkenyl or alkynyl group having 2 to 40 C atoms or a branched or cyclic alkyl, alkoxy or thioalkoxy group having 3 to 40 C atoms, each of which may be substituted by one or more radicals $R^4$, where one or more adjacent or non-adjacent $CH_2$ groups may be replaced by —C≡C—, —$R^4$C=$CR^4$—, $Si(R^4)_2$, C=O, C=S, C=Se, C=$NR^4$, P(=O)($R^4$), SO, $SO_2$, $NR^4$, O, S, C(=O)O or C(=O)$NR^4$; two or more substituents $R^3$ here may be linked to one another and optionally form a mono- or polycyclic aliphatic, aromatic or heteroaromatic ring system, and in addition Ar on each occurrence, identically or differently, represents an aryl group having 6 to 60 C atoms, which may optionally be substituted by one or more substituents $R^4$, and $R^4$ on each occurrence, identically or differently, is H, D or an aliphatic, aromatic or heteroaromatic organic radical having 1 to 20 C atoms, in which, in addition, one or more H atoms may be replaced by D or F; two or more adjacent or non-adjacent radicals $R^4$ here may be linked to one another and optionally form a mono- or polycyclic aliphatic, aromatic or heteroaromatic ring system.

The aromatic or heteroaromatic ring system of the dopant is particularly preferably substituted by at least one group of the formula (A),

formula (A)

where the dashed line represents the bond from the group to the aromatic or heteroaromatic ring system, and Ar is as defined above.

The said fluorescent dopants are particularly preferably selected from condensed aromatic hydrocarbons, monostyrylamines, distyrylamines, tristyrylamines, tetrastyrylamines, styrylphosphines, styryl ethers, arylamines, and arylamines containing condensed aryl groups. A monostyrylamine is taken to mean a compound which contains one styryl group and at least one amine, which is preferably aromatic. A distyrylamine is taken to mean a compound which contains two styryl groups and at least one amine, which is preferably aromatic. A tristyrylamine is taken to mean a compound which contains three styryl groups and at least one amine, which is preferably aromatic. A tetrastyrylamine is taken to mean a compound which contains four styryl groups and at least one amine, which is preferably aromatic. An arylamine or an aromatic amine in the sense of this invention is taken to mean a compound which contains three aromatic or heteroaromatic ring systems bonded directly to the nitrogen, at least one of which is preferably a condensed ring system having at least 14 aromatic ring atoms. The styryl groups are particularly preferably stilbenes, which may also be substituted further on the double bond or on the aromatic ring system. Examples of dopants of this type are substituted or unsubstituted tristilbenamines or further dopants which are described, for example, in WO 06/000388, WO 06/058737, WO 06/000389, WO 07/065,549 and WO 07/115,610. Compounds in accordance with WO 06/122630 are furthermore preferred as dopants. Preferred dopants are furthermore diarylamine derivatives or bis(diarylamine) derivatives of monobenzoindenofluorene or dibenzoindenofluorene, for example in accordance with WO 08/006,449 or WO 07/140, 847. Preferred dopants are again furthermore the fluorene derivatives disclosed in the application WO 2010/012328.

According to a further embodiment of the invention, the mixture comprises one or more phosphorescent emitter compounds besides the compounds according to the invention.

A phosphorescent emitter compound in the sense of this invention is a compound which exhibits luminescence from an excited state of relatively high spin multiplicity, i.e. a spin multiplicity >1, in particular from an excited triplet state, at room temperature. For the purposes of this invention, all luminescent iridium and platinum compounds, in particular, are to be regarded as phosphorescent compounds.

The phosphorescent emitter compounds are preferably selected from the group comprising organometallic complexes having at least one metal-carbon bond which contain a metal selected from chromium, molybdenum, tungsten, rhenium, ruthenium, osmium, rhodium, iridium, nickel, palladium, platinum, copper, silver and gold, and particularly preferably selected from molybdenum, tungsten, rhenium, ruthenium, osmium, iridium, platinum, gold and copper, and very particularly preferably selected from iridium, platinum and copper.

According to a preferred embodiment of the invention, the phosphorescent or fluorescent emitter compound contains one or more deuterium atoms. The emitter compound particularly preferably contains one or more phenyl, biphenyl, terphenyl, diphenyltriazinyl, naphthyl, pyridinyl or methyl groups, which carry one or more deuterium atoms and may optionally be substituted by one or more radicals $R^1$, where $R^1$ is as defined above. The said phenyl, biphenyl, terphenyl, diphenyltriazinyl, naphthyl, pyridinyl or methyl groups very particularly preferably carry one or more deuterium atoms and no further substituents apart from deuterium and hydrogen.

In a further particularly preferred embodiment of the invention, the said phenyl, biphenyl, terphenyl, diphenyltriazinyl, naphthyl, pyridinyl or methyl groups are fully substituted by deuterium atoms.

Particularly preferred embodiments of emitters in the mixtures according to the invention are the following compounds.

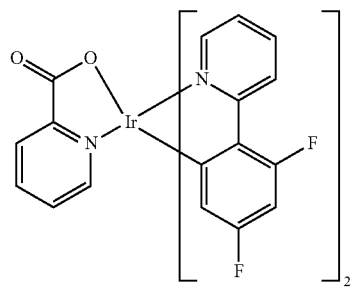

47

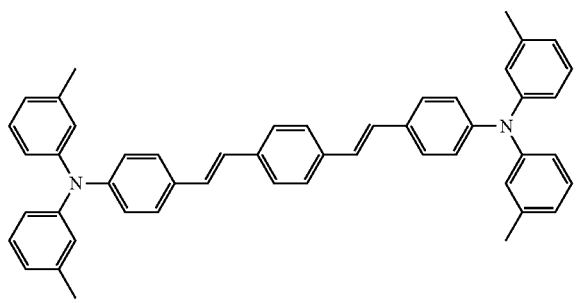

48

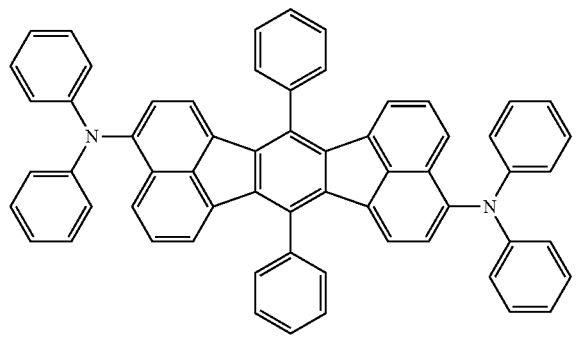

49

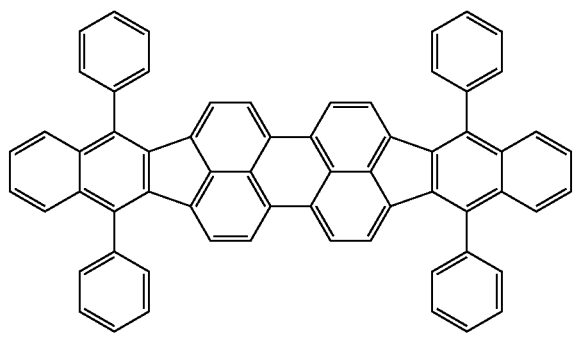

50

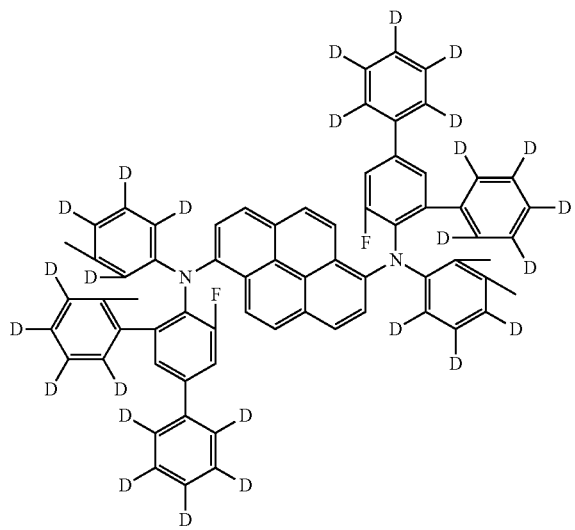

51

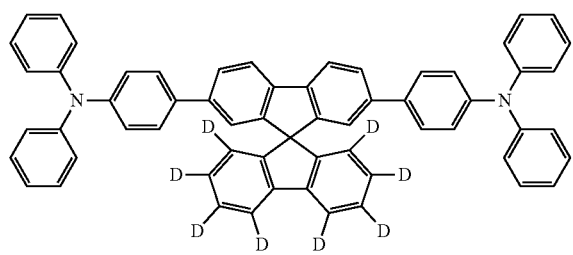
52
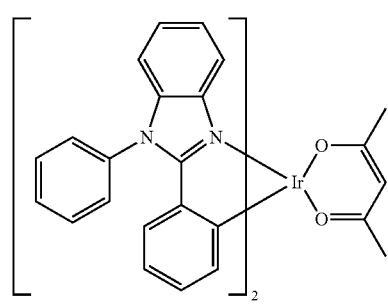
53
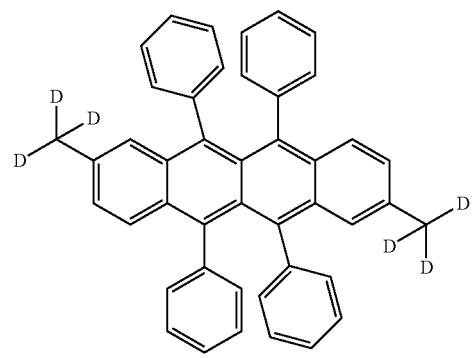
54
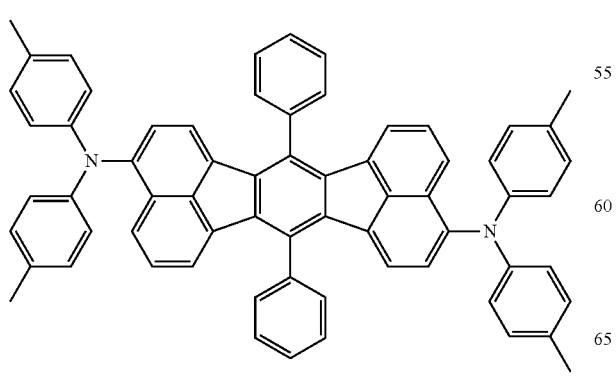
55
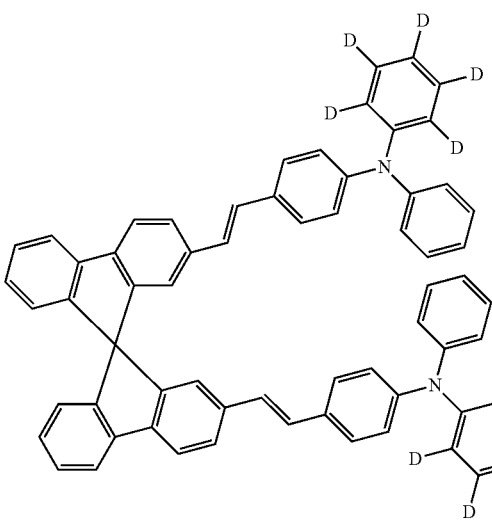
56
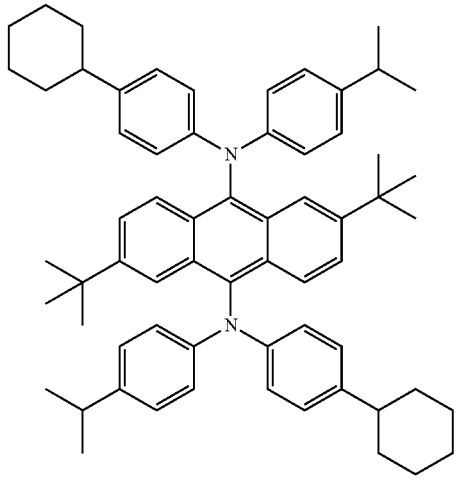
57
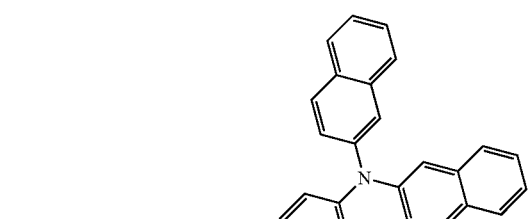
58

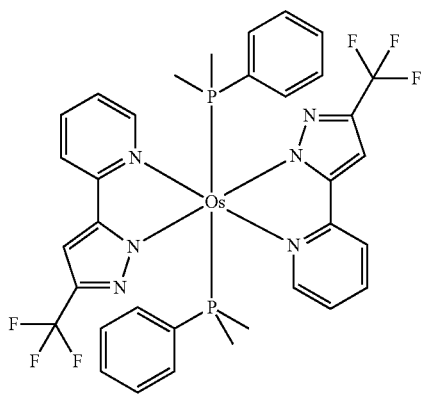
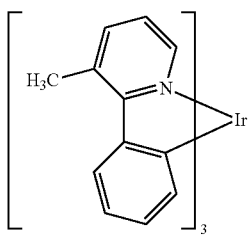
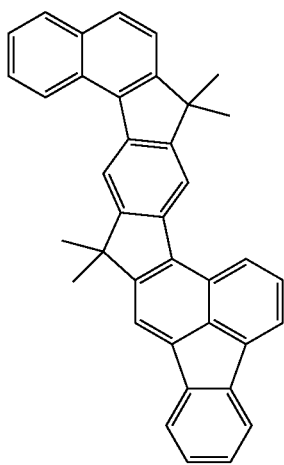
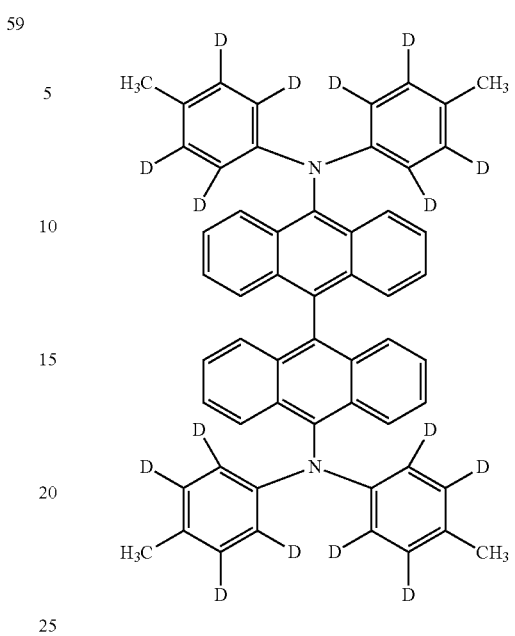
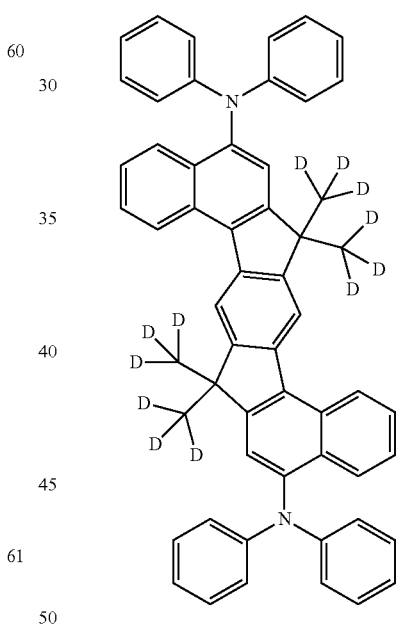
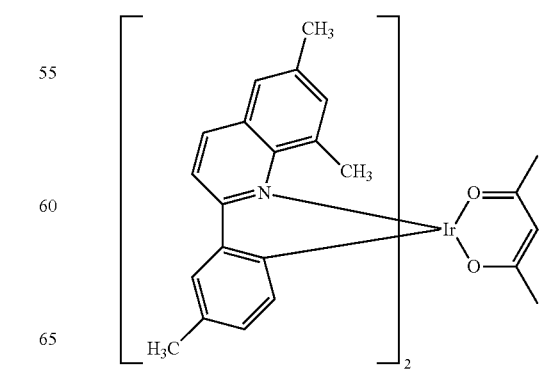

75
-continued
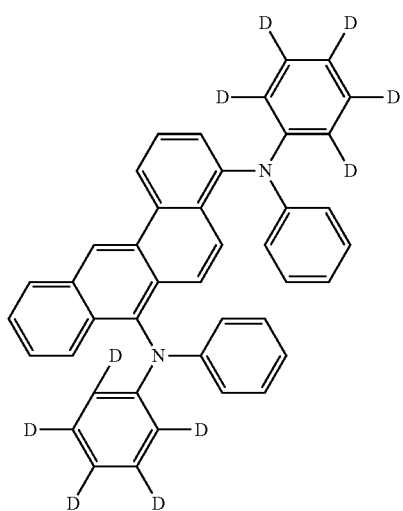
65
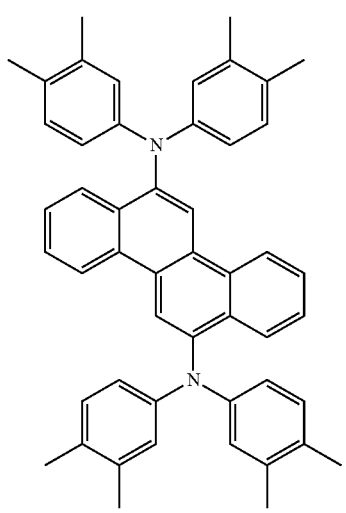
66
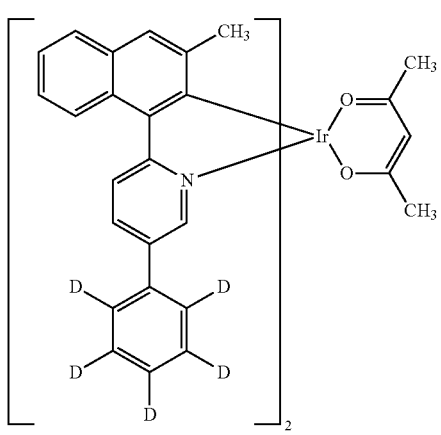
67
76
-continued
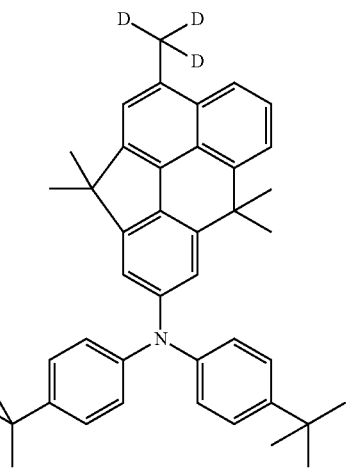
68
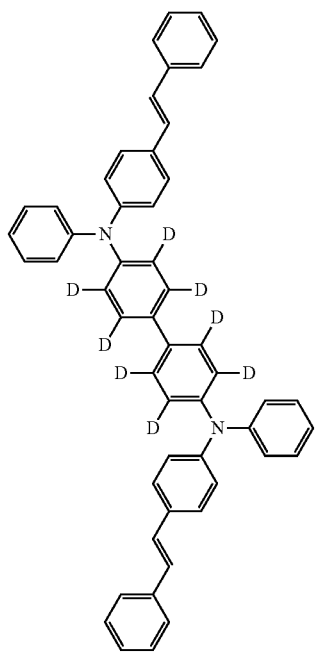
69
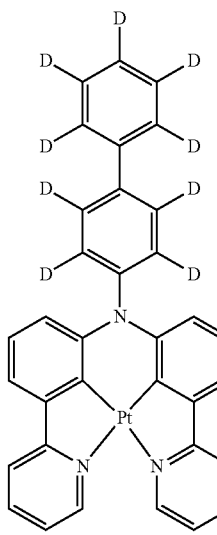
70

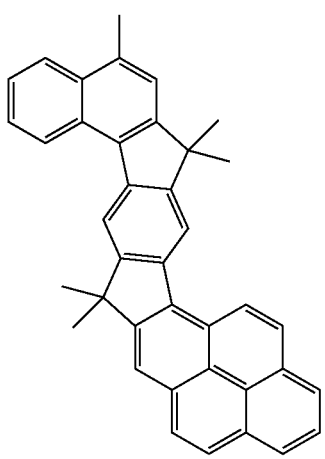
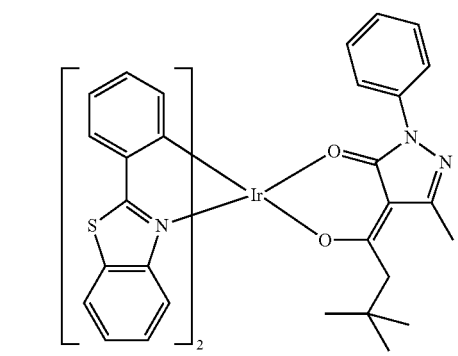
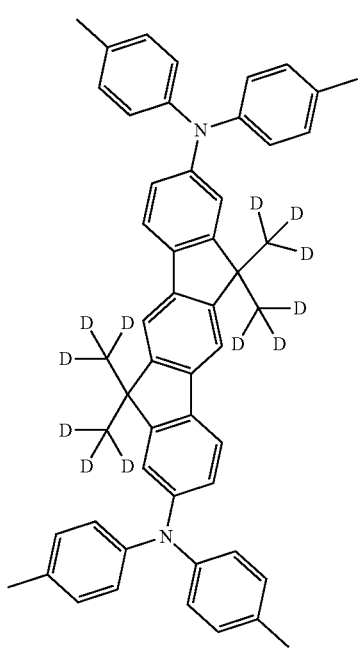
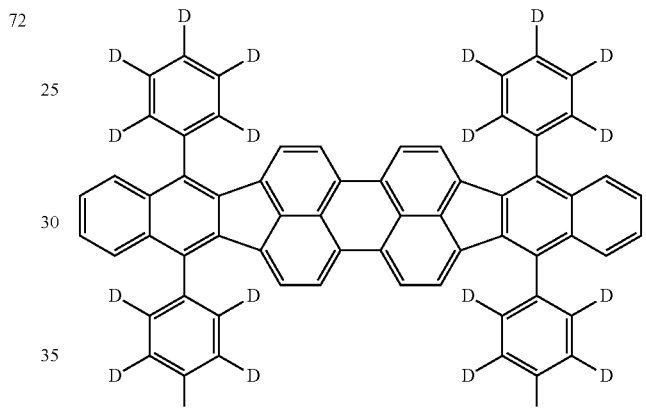
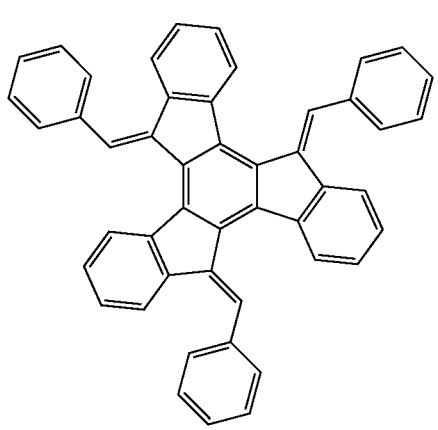
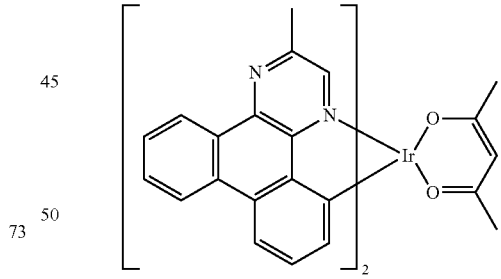
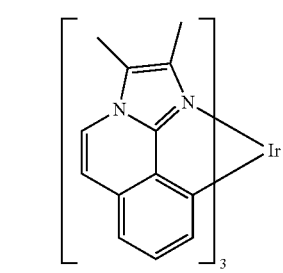

-continued
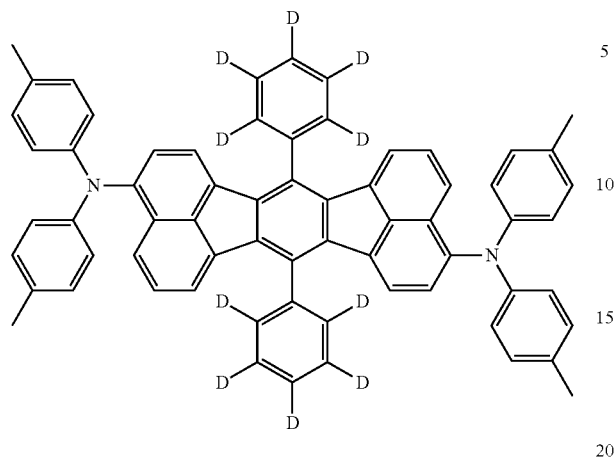
78
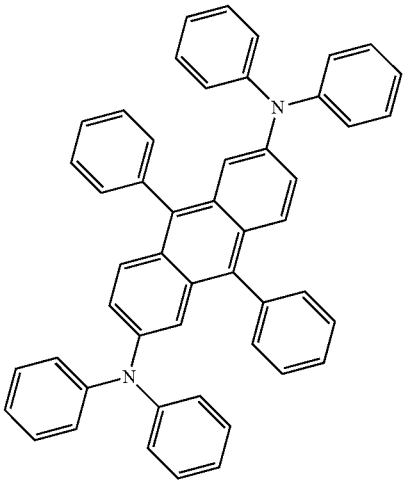
81
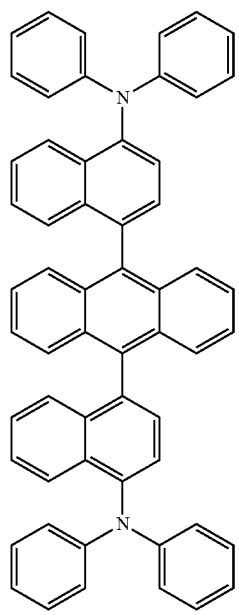
79
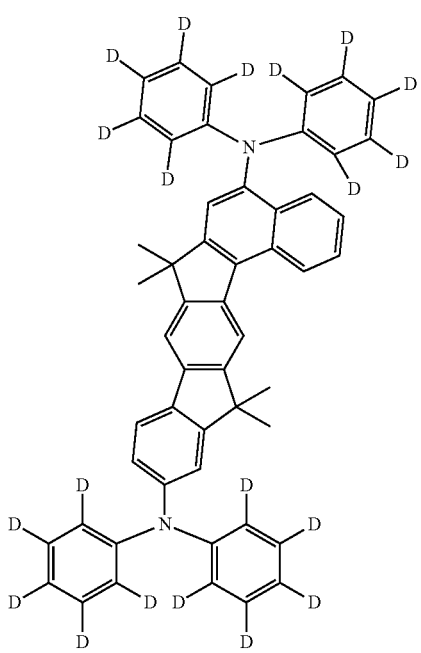
82
80

81
-continued
83
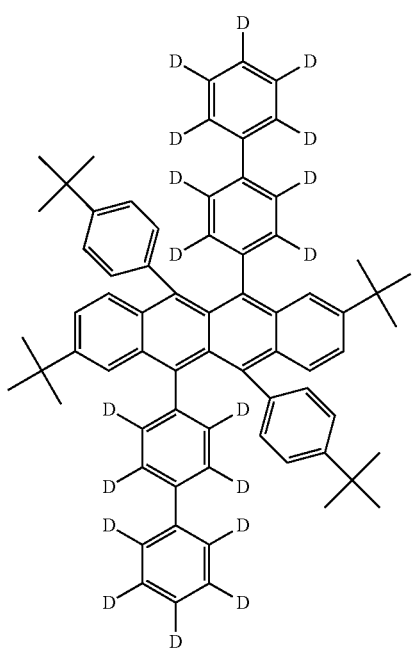
84
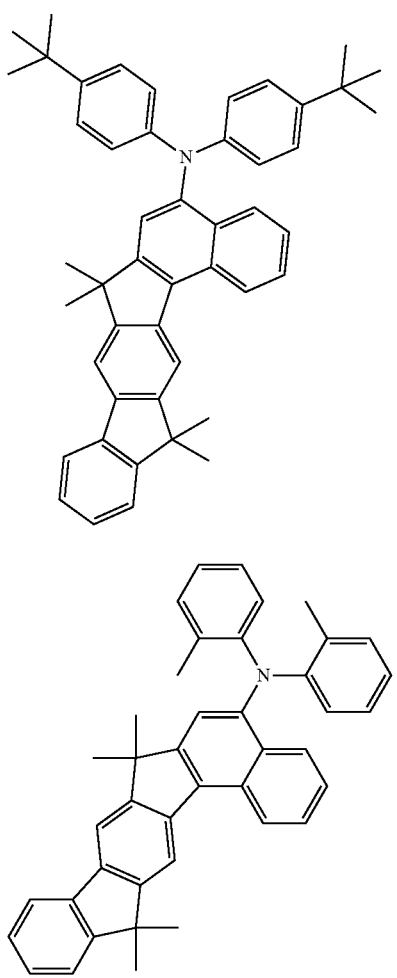
85
82
-continued
86
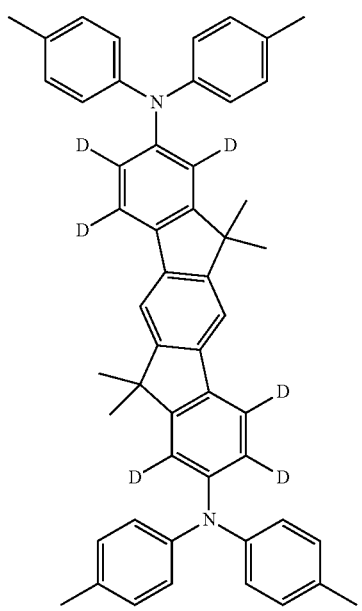
87
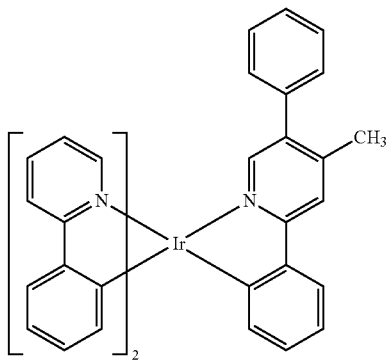
88
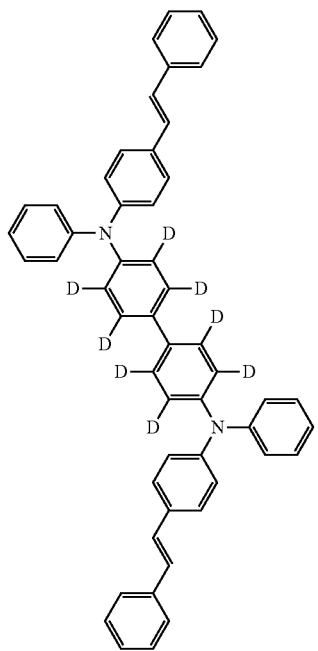

89
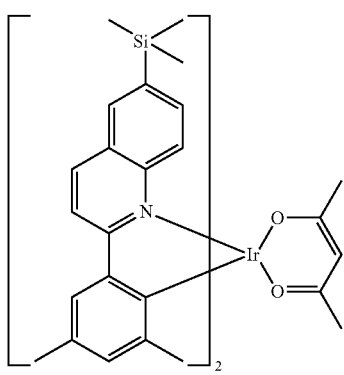
90
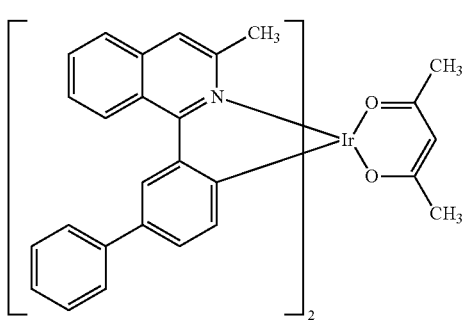
91
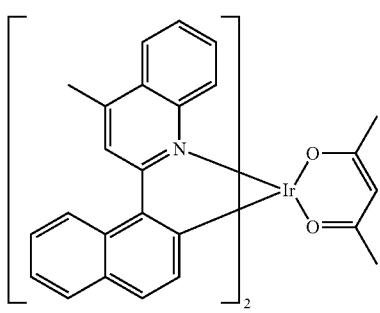
92
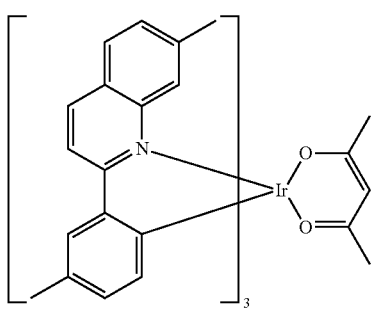
93
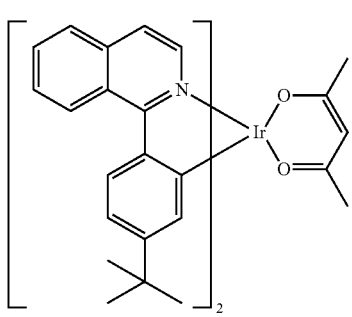
94
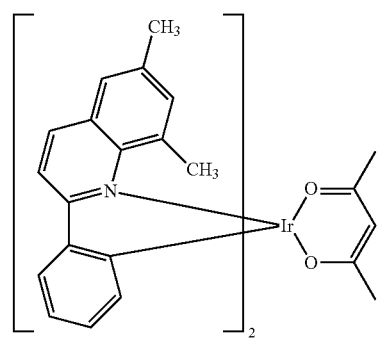
95
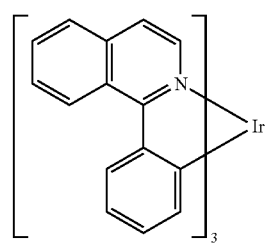
96
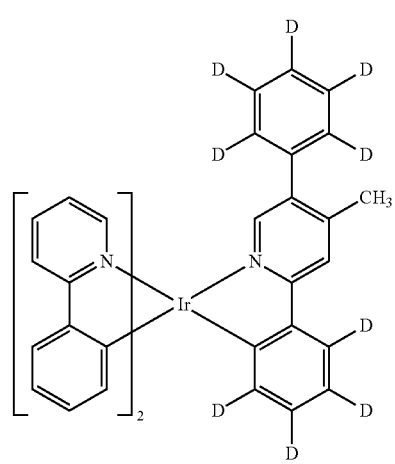
97
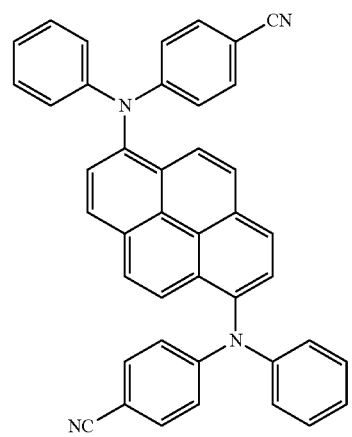

98

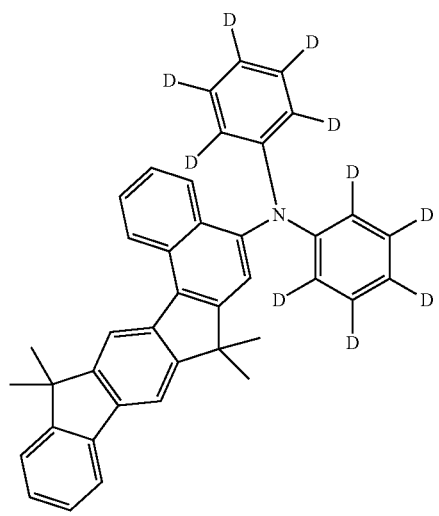

99

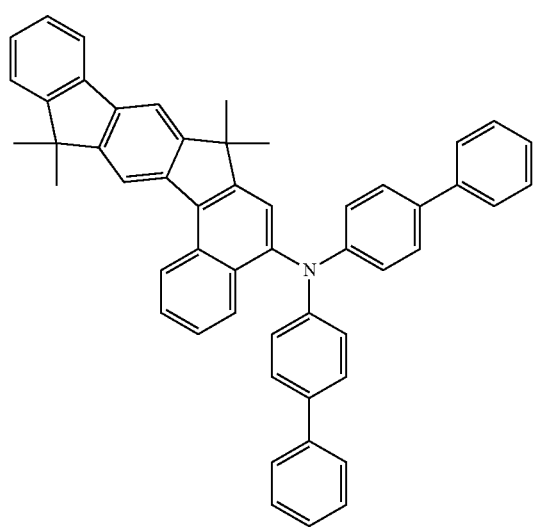

100

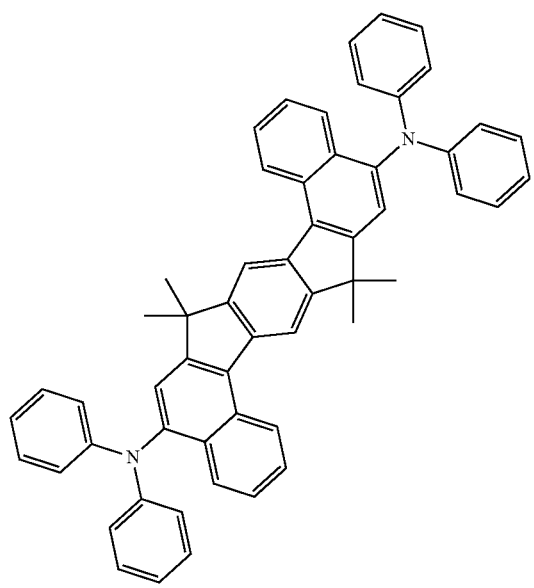

101

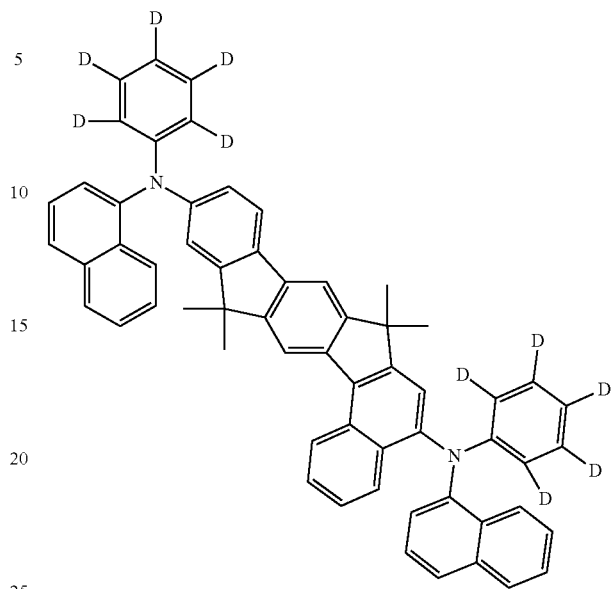

102

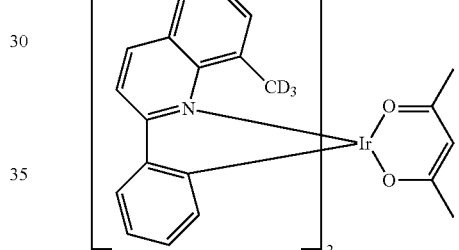

103

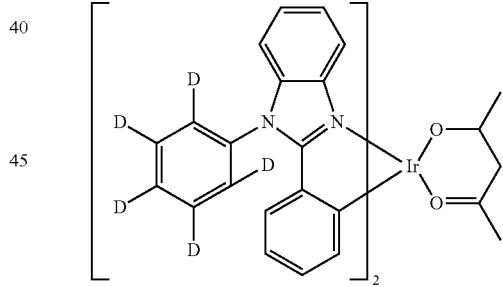

The invention furthermore relates to formulations comprising at least one compound of the formula (I) or at least one of the above-mentioned mixtures according to the invention and at least one solvent, preferably at least one organic solvent.

The compounds according to the invention or the mixtures according to the invention can be used in electronic devices, preferably in organic electroluminescent devices. The compounds according to the invention are preferably present in one or more emitting layers here.

The invention thus also relates to a layer, preferably an emitting layer of an organic electroluminescent device, comprising a compound of the formula (I), as defined above.

The invention thus also relates to the use of a compound of the formula (I) or of one of the mixtures according to the invention described above in electronic devices, preferably in organic electroluminescent devices. A preferred use is the use as host material for fluorescent or phosphorescent dopants, particularly preferably for fluorescent dopants.

In a further preferred embodiment of the invention, the compound of the formula (I) is employed as co-host material in an emitting layer of an OLED. In this case, the compound is preferably present in the emitting layer in a proportion of 5 to 95% by vol.

A host material in a system comprising matrix (=host) and dopant (=emitter compound) is taken to mean the component which is present in the system in the higher proportion. In a system comprising one matrix material and a plurality of dopant materials, the matrix material is taken to mean the component whose proportion in the mixture is the highest.

The mixture of dopant material and host material in these cases comprises between 0.5 and 40% by vol., preferably between 1 and 30% by vol., particularly preferably between 2 and 15% by vol., of the dopant compound, based on the entire mixture comprising dopant material and host material. Correspondingly, the mixture comprises between 99.5 and 60% by vol., preferably between 99 and 70% by vol., particularly preferably between 98 and 85% by vol., of the host material, based on the entire mixture comprising dopant material and host material.

The invention likewise relates to electronic devices, preferably organic electroluminescent devices (OLEDs), organic field-effect transistors (O-FETs), organic thin-film transistors (O-TFTs), organic light-emitting transistors (O-LETs), organic integrated circuits (O-ICs), organic solar cells (O-SCs), organic field-quench devices (O-FQDs), light-emitting electrochemical cells (LECs), organic laser diodes (O-lasers) or organic photoreceptors, containing at least one compound of the formula (I) or a mixture of a compound of the formula (I) with one of the emitter compounds defined above.

The electronic device preferably contains the compound according to the invention as host material, particularly preferably together with one or more emitter compounds, which are very particularly preferably selected from fluorescent dopants containing an aromatic or heteroaromatic ring system having 5 to 60 aromatic ring atoms, which may be substituted by one or more substituents $R^3$, where $R^3$ is as defined above. The compound according to the invention is furthermore preferably located in an emitting layer of the electronic device.

Preference is given to emitter compounds as disclosed above for the mixtures according to the invention, in particular in the preferred embodiments disclosed there, very particularly preferably the compounds 47 to 103.

The organic electroluminescent device may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to three-layer systems, where the three layers exhibit blue, green and orange or red emission (for the basic structure see, for example, WO 05/011013).

Apart from a cathode, an anode and at least one emitting layer, the electroluminescent device according to the invention may also comprise further layers, for example in each case one or more hole-injection layers, hole-transport layers, hole-blocking layers, electron-transport layers, electron-injection layers, exciton-blocking layers, charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p/n junctions. It is likewise possible for one or more interlayers which have, for example, an exciton-blocking function to be introduced between two emitting layers. However, it should be pointed out that each of these layers does not necessarily have to be present. The above-mentioned layers may also comprise compounds of the formula (I), as defined above.

Preference is furthermore given to an organic electroluminescent device in which one or more layers are applied by means of a sublimation process, in which the materials are applied by vapour deposition in vacuum sublimation units at an initial pressure of less than $10^{-5}$ mbar, preferably less than $10^{-6}$ mbar. It is also possible for the initial pressure to be even lower, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure between $10^{-5}$ mbar and 1 bar.

Preference is furthermore given to an organic electroluminescent device, characterised in that one or more layers are produced from solution, such as, for example, by spin coating, or by means of any desired printing process, such as, for example, screen printing, flexographic printing or offset printing, but particularly preferably LITI (light induced thermal imaging, thermal transfer printing) or ink-jet printing. Soluble compounds, which are obtained, if necessary, by suitable substitution, are necessary for this purpose. These methods are also suitable, in particular, for the use of oligomers and polymers comprising the compounds according to the invention in organic electroluminescent devices.

Preference is furthermore given to organic electroluminescent devices, characterised in that they have been produced by a hybrid process in which one or more layers have been applied from solution and one or more other layers have been applied by means of vapour deposition by OVPD or carrier-gas sublimation.

The said processes for the production of organic electroluminescent devices are generally known to the person skilled in the art and can be applied by him without problems to devices containing compounds of the formula (I).

The compounds of the formula (I) and organic electroluminescent devices containing one or more of the compounds of the formula (I) have one or more of the following advantages over the prior art:

1. The compounds according to the invention have improved sublimation stability and can therefore be obtained in purer form. Devices containing these compounds thus contain fewer impurities, which has a positive influence on their performance data and in particular increases their lifetime.
2. The compounds according to the invention are very highly suitable for use as matrix material for fluorescent and phosphorescent emitters, in particular for fluorescent emitters, where they result in good efficiencies, long lifetimes and low operating voltages of the electroluminescent device.
3. The compounds have high decomposition stability, which has a positive influence on the property profile of the organic electroluminescent device, in particular its lifetime.
4. Owing to their modular structure, the compounds are readily accessible synthetically and can be prepared economically, for example by organometallic coupling of the deuterated aromatic or heteroaromatic groups Y to the group Z functioning as skeleton.

The following examples are intended to explain the invention in greater detail without restricting it. In particular, the features, properties and advantages described therein of the defined compounds on which the examples are based also relate to other compounds which are not mentioned in detail, but fall within the scope of protection of the claims, unless mentioned otherwise elsewhere.

USE EXAMPLES

Example 1

Synthesis of 5-benz[a]anthracen-4-yl-12-perdeuterophenylnaphthacene

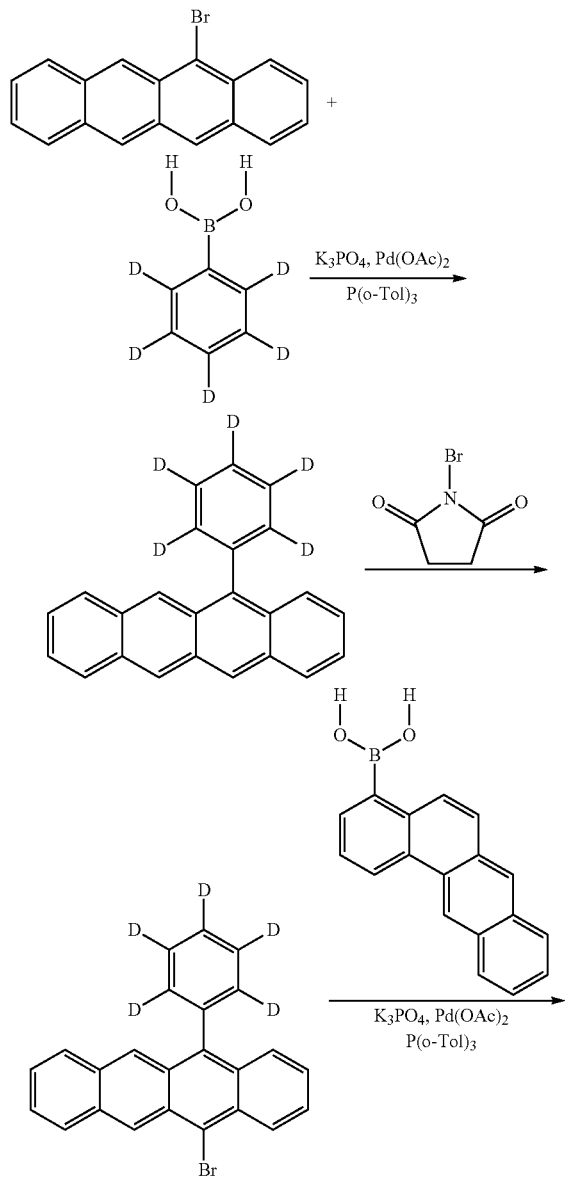

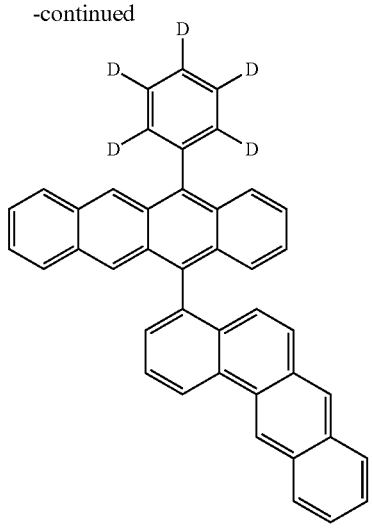

1st Step

Tetracenyl bromide (500 mmol, 153.6 g), perdeuterophenylboronic acid (590 mmol, 75.2 g) and potassium phosphate (1500 mmol, 318.4 g) are initially introduced. 900 ml of toluene, 300 ml of dioxane and 1000 ml of water are subsequently added. The mixture is degassed, tris-orthotolylphosphine (6 mmol, 1.83 g) is added, and the mixture is stirred for 5 min. Palladium acetate (1 mmol, 224.5 mg) is then added, and the mixture is heated under reflux with rapid stirring. When the reaction is complete (TLC check), the mixture is filtered through a fluted filter and subsequently through aluminium oxide, and the filtrate is evaporated. The solid obtained is filtered off, washed with EtOH and dried in vacuo (yield 121.3 g, 78%).

2nd Step

Perdeuterophenyltetracene (392 mmol, 121.3 g) is initially introduced and dissolved in dry THF (1 l). The solution is degassed and warmed to 40° C. NBS (412 mmol, 73.5 g) is added in 6 portions over the course of 20 min. The mixture is subsequently stirred at an oil-bath temperature of 50° C. for 3 h. The mixture is then substantially evaporated in vacuo, and MeOH (400 ml) is added. The mixture is evaporated in a rotary evaporator at 50° C. for 30 min, and the solid is subsequently isolated by filtration, washed with warm MeOH and dried in vacuo. The purification is carried out by stirring in hot MeOH (400 ml), subsequently allowing the mixture to cool, and isolating the solid by filtration and drying in vacuo, giving 138.2 g (91%).

3rd Step

Bromoperdeuterophenylnaphthacene (356 mmol, 138.2 g) and 4-benzanthracene boronic acid (393 mmol, 106.9 g) are initially introduced together with potassium phosphate (757 mmol, 160.7 g). 1200 ml of toluene, 480 ml of dioxane and 1200 ml of water are added with stirring, and the mixture is degassed by passing argon through it. Tris-orthotolylphosphine (21.4 mmol, 6.5 g) is subsequently added, the mixture is stirred for 2 min, and palladium(II) acetate (3.6 mmol, 801 mg) is subsequently added. The mixture is heated under reflux overnight. After cooling, the solid formed is filtered off with suction, washed with toluene, water/EtOH 1:1 and pure EtOH and dried. The purification is carried out by multiple recrystallisation from 1,2-dichlorobenzene, giving 104.7 g of product, corresponding to a yield of 55%.

The material is subsequently sublimed twice at $1\times10^{-6}$ mbar and 370° C. No thermal decomposition at all was found at an HPLC resolution of 0.01%.

The undeuterated material (see compound H1 in the Device Examples) was pprepared and purified analogously. The sublimations were carried out under analogous conditions, but an approx. 5° C. higher temperature was required. After the two sublimation passages, thermal decomposition products with a proportion of about 0.01-0.02% were detected in the product HPLC.

The deuterated material thus has improved thermal (sublimation) stability compared with the undeuterated material.

Example 2

Synthesis of 10-(4,6-diperdeuterophenyl-1,3,5-triazin-2-yl)-12,12-dimethyl-10,12-dihydro-10-azaindeno[2,1-b]-fluorene

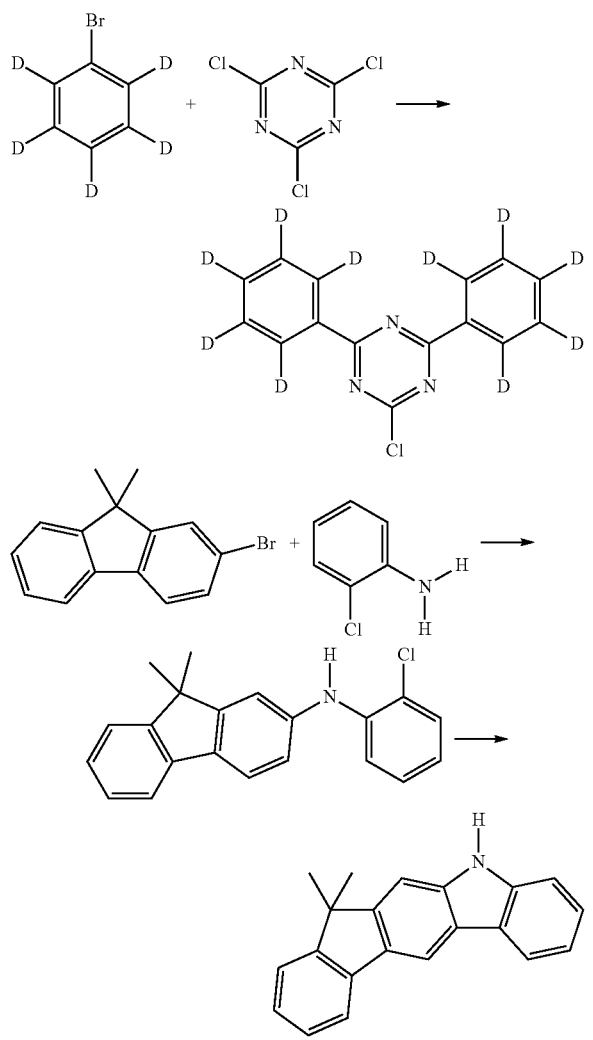

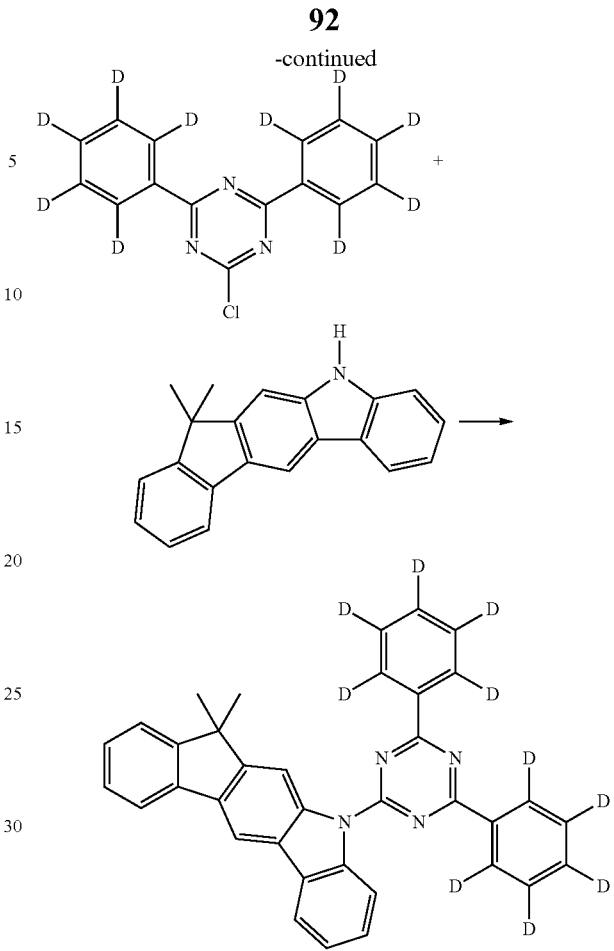

1st Step

Magnesium (48.6 g, 2 mol) is initially introduced, and the apparatus is dried by heating under $N_2$, and the reaction mixture is then cooled. $d_5$-Bromobenzene (324.0 g, 2 mol) is mixed with 1500 ml of THF, slowly added dropwise via a dropping funnel and heated locally at the dropwise addition point (duration about 1 h). The Grignard reagent is subsequently stirred under reflux for a further 1 h and then cooled to room temperature. Cyanuric chloride (122.8 g, 0.67 mol) in 500 ml of THF is initially introduced in the second flask, which has been dried by heating, and cooled to 0° C. The cooled Grignard reagent is then slowly added dropwise at this temperature at such a rate that an internal temperature of 20° C. is not exceeded (duration about 1 h). The mixture is stirred overnight at room temperature. HCl and water are mixed and introduced into the reaction mixture. The phases are separated, and the aqueous phase is extracted 2× with 500 ml of ethyl acetate. The combined organic phases are extracted 2× with 500 ml of water. Finally, the organic phase is washed 1× with saturated $NaHCO_3$ solution, dried over magnesium sulfate and evaporated to dryness in a rotary evaporator. 500 ml of ethanol are added to the solid, and the mixture is stirred at 60° C. in a rotary evaporator, and the solid is filtered off with suction and washed with ethanol. The solid is washed with 1000 ml of boiling ethanol, filtered off with suction and washed with a little ethanol, then dried in a vacuum drying cabinet, giving 141.2 g of product, corresponding to a yield of 71%.

2nd Step

Chloroaniline (84 g, 659 mmol) and 2-bromo-9,9-dimethylfluorene (150 g, 550 mmol) are dissolved in 2.4 l of toluene, introduced into a flask and saturated with protective gas for 30 min. Then, firstly DPPF (4.5 g, 8.13 mmol) and, 5 min. later, Pd(acac)$_2$ (1.48 g, 6.59 mmol) and then sodium tert-butoxide (137.3 g, 1.43 mol) in the solid state are added rapidly, and the mixture is degassed by means of protective gas for a further 10 min. The mixture is heated under reflux for 18 hours, and the conversion is then checked (TLC check). About 1 l of water is added to the cooled reaction solution, and the mixture is stirred, and the water phase is then separated off and extracted 2× with 400 ml of toluene. The combined organic phases are washed 2× with about 700 ml of water, 1× with about 500 ml of sat. NaCl solution, and the toluene phase is then dried using MgSO$_4$ and evaporated to dryness in a rotary evaporator. The resultant residue is washed with about 1 litre of boiling heptane, the mixture is filtered through a frit filled with Celite/silica gel, and the filtrate is evaporated to dryness in vacuo, leaving a dark-green oil. 127.4 g of product are obtained, corresponding to a yield of 99%.

3rd Step

Potassium carbonate (137.6 g, 995.85 mmol) and pivalic acid (12.2 g, 119.50 mmol) are initially introduced in a flask, and the product from the 2$^{nd}$ step (dark-green oil) is dissolved in 2 litres of NMP and added. The mixture is degassed by passing in N$_2$ for 30 min. Firstly, tri-tert-butylphosphine (31.9 ml, 31.87 mmol), then Pd(OAc)$_2$ (4.7 g, 19.92 mmol) are added, and the mixture is heated at an internal temperature of 130° C. for 4 h (TLC check). The complete reaction mixture is evaporated to dryness in a rotary evaporator at a water-bath temperature of 95° C. and at 1 mbar. The crude product is dissolved in about 1000 ml of toluene and about 500 ml of water. The phases are subsequently separated, the water phase is washed 3× with about 200 ml of toluene each time, and the combined organic phases are washed 3× with about 500 ml of water. The organic phase is dried over Mg sulfate and eluted with toluene over a frit filled with Celite/silica gel. The filtrate is evaporated in a rotary evaporator, about 1000 ml of cyclohexane are added, and the mixture is stirred at 50° C. for 1 h in a rotary evaporator. The solid is filtered off with suction and washed with cyclohexane until the filtrate is colourless, then dried in a vacuum drying cabinet, giving 48.6 g of product, corresponding to a yield of 43%.

4th Step

Sodium hydride (60% NaH, 7.7 g, 193.99 mmol) in mineral oil is initially introduced in 340 ml of DMF. The product from the 3rd step (45 g, 161.16 mmol) is dissolved in 225 ml of DMF and slowly added dropwise at room temperature, and the mixture is stirred for a further 2 hours. d$_5$-Diphenylchlorotriazine (product from the 1st step, 49.6 g, 177.27 mmol) is dissolved in 340 ml of THF with stirring. Stirring is continued overnight at RT, the conversion is then checked (TLC check), and the mixture is worked up. The reaction mixture is added to 0.8 kg of ice and cooled to room temperature, and the precipitated solid is filtered off with suction, washed 2× with methanol and 2× with heptane and dried. The substance is extracted a number of times with toluene in a hot extractor for 2 h. The substance is then suspended a number of times in heptane, and toluene is added at the boil until everything has dissolved. The mixture is cooled to room temperature, and the solid obtained is filtered off with suction. The solid is recrystallised a number of times from boiling toluene, then washed with heptane and dried, giving 25.7 g of product, corresponding to a yield of 31%.

The material is subsequently sublimed twice at 1×10$^{-6}$ mbar and 290° C.

Example 3

Synthesis of 2-diperdeuterophenyltriazenyl-9,9'-spirobifluorene

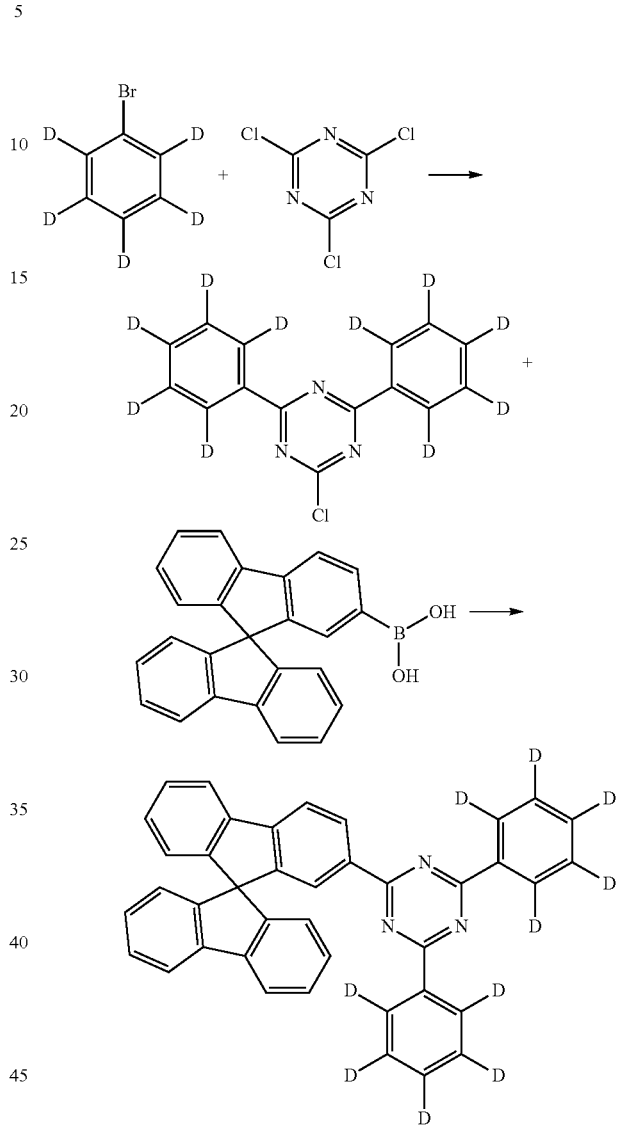

1st Step:

Corresponds to the 1st step of Example 2.

2nd Step d$_5$-Diphenylchlorotriazine (93%, 86.9 g, 313 mmol) and spiro-2-boronic acid (95%, 154.3 g, 406.9 mmol, purchased commercially from HanFine Chemicals, Korea) are initially introduced in 2100 ml of toluene/dioxane/water (3:3:1) mixture with 35.9 g (338.9 mmol) of Na$_2$CO$_3$ and degassed in the apparatus for 60 min. by passing protective gas into the reaction solution. 7.2 g (6.3 mmol) of tetrakistriphenyl-phosphinopalladium are then added, and the mixture is heated under reflux for 5 hours. When the reaction is complete (TLC reaction check), the phases are separated, and the organic phase is washed, dried using Na$_2$SO$_4$ and evaporated to ⅓ of the volume. The precipitated solid is filtered off with suction and washed with water, ethanol and heptane. The solid is extracted with toluene in a hot extractor for 24 h, and the precipitated white solid is filtered off with suction and washed with ethanol and dried.

The solid is recrystallised from 1500 ml of boiling dioxane. The mixture is stirred overnight at room temperature, and the precipitated solid is filtered off with suction, washed with ethanol and dried. The substance is washed by stirring with 900 ml of boiling toluene, cooled and filtered off with suction, giving 127 g of product, corresponding to a yield of 73%. The material is subsequently sublimed twice at $5\times10^{-6}$ mbar and about 310° C.

Examples 4-21

Production of OLEDs

OLEDs according to the invention and OLEDs in accordance with the prior art are produced by a general process in accordance with WO 04/058911, which is adapted to the circumstances described here (layer-thickness variation, materials used).

The results for various OLEDs are presented in the following examples (see Tables 1 to 3). Glass plates coated with structured ITO (indium tin oxide) in a thickness of 150 nm are coated with 20 nm of PEDOT (poly-(3,4-ethylenedioxy-2,5-thiophene), spin-coated from water; purchased from H.C. Starck, Goslar, Germany) for improved processing. These coated glass plates form the substrates to which the OLEDs are applied. In principle, the OLEDs have the following layer structure: substrate/hole-transport layer (HTL)/optional interlayer (IL)/electron-blocking layer (EBL)/emission layer (EML)/optional hole-blocking layer (HBL)/electron-transport layer (ETL)/optional electron-injection layer (EIL) and finally a cathode. The cathode is formed by an aluminium layer with a thickness of 100 nm. The precise structure of the OLEDs is shown in Table 1. The materials used for the production of the OLEDs are shown in Table 3.

All the materials are applied by thermal vapour deposition in a vacuum chamber. The emission layer here always consists of at least one matrix material (host material) and an emitting dopant (emitter), to which the matrix material or matrix materials is (are) admixed in a certain proportion by volume by co-evaporation. An expression such as H1:SEB1 (95%:5%) here means that material H1 is present in the layer in a proportion by volume of 95% and SEB1 is present in the layer in a proportion by volume of 5%. Analogously, the electron-transport layer may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminance characteristic lines (IUL characteristic lines), and the lifetime are determined. The lifetime is defined as the time after which the luminous density has dropped to a certain proportion from a certain initial luminous density $l_0$. The expression LD50 means that the said lifetime is the time by which the luminous density has dropped to $0.5 \cdot l_0$ (to 50%), i.e. from, for example, 6000 cd/m² to 3000 cd/m². The expression LD80 means that the lifetime has dropped to 80% of the initial luminance.

The compounds according to the invention can be employed, inter alia, as matrix materials (host materials) for fluorescent dopants. Compound H2 according to the invention is used here (cf. Table 3). Compound H1 is used as comparison in accordance with the prior art. OLEDs containing the red-emitting dopant SER1 are shown. The results for the OLEDs are summarised in Table 2. Ex. 4-7 show OLEDs comprising undeuterated host material in accordance with the prior art and serve as comparative examples. OLEDs 13-16 according to the invention show the advantages on use of compounds of the formula (I) in devices containing fluorescent emitters.

The use of deuterated compounds according to the invention enables improvements to be achieved in the operating lifetime of the components compared with the prior art. Compared with the reference components, the electrical characteristic data are in all cases comparable or better. With an otherwise identical layer structure, components using H2 exhibit longer operating lifetimes with increased power efficiency and operating voltage.

On use as matrix materials in phosphorescent OLEDs, compounds of the formula (I) likewise give rise to significant improvements in all parameters compared with the prior art, in particular with respect to lifetime and power efficiency. Examples used are matrix materials H3 and H6 according to the invention (cf. Table 3). Ex. 8-12 show OLEDs comprising undeuterated host material and phosphorescent dopants in accordance with the prior art and serve as comparative examples. Examples 17-21 according to the invention show the advantages on use of compounds of the formula (I) in devices containing phosphorescent emitters. In particular, higher efficiency and a longer operating lifetime are measured on use of the compounds according to the invention.

TABLE 1

Structure of the OLEDs

| Ex. | HTL Thickness | IL Thickness | EBL Thickness | EML Thickness | ETL Thickness | EIL Thickness |
|---|---|---|---|---|---|---|
| 4 (comp.) | HTM1 140 nm | HIL1 5 nm | NPB 20 nm | H1:SER1 (99%:1%) 20 nm | ETM1:LiQ (50:50) 30 nm | |
| 5 (comp.) | HTM1 140 nm | HIL1 5 nm | NPB 20 nm | H1:SER1 (99%:1%) 20 nm | ETM1:LiQ (25:75) 30 nm | |
| 6 (comp.) | HTM1 140 nm | HIL1 5 nm | NPB 20 nm | H1:SER1 (98%:2%) 20 nm | ETM1 30 nm | LiQ 3 nm |
| 7 (comp.) | HTM1 140 nm | HIL1 5 nm | NPB 20 nm | H1:SER1 (95%:5%) 20 nm | Alq 30 nm | LiF 1 nm |

TABLE 1-continued

Structure of the OLEDs

| Ex. | HTL Thickness | IL Thickness | EBL Thickness | EML Thickness | ETL Thickness | EIL Thickness |
|---|---|---|---|---|---|---|
| 8 (comp.) | HTM1 20 nm | | NPB 20 nm | H4:TER1 (85%:15%) 30 nm | Alq 20 nm | LiF 1 nm |
| 9 (comp.) | HTM1 160 nm | | EBM1 20 nm | H4:TEG1 (90%:10%) 30 nm | ETM1:LiQ (50%:50%) 40 nm | |
| 10 (comp.) | HTM1 120 nm | | NPB 20 nm | H5:TER1 (85%:15%) | Alq 20 nm | LiF 1 nm |
| 11 (comp.) | HTM1 160 nm | | EBM1 20 nm | H5:TEG1 (90%:10%) | ETM1:LiQ (50%:50%) 30 nm | |
| 12 (comp.) | HTM1 160 nm | | EBM1 20 nm | H5:TEG1 (90%:10%) | ETM1:LiQ (50%:50%) 40 nm | |
| 13 | HTM1 140 nm | HIL1 5 nm | NPB 20 nm | H2:SER1 (99%:1%) 20 nm | ETM1:LiQ (50:50) 30 nm | |
| 14 | HTM1 140 nm | HIL1 5 nm | NPB 20 nm | H2:SER1 (99%:1%) 20 nm | ETM1:LiQ (25:75) 30 nm | |
| 15 | HTM1 140 nm | HIL1 5 nm | NPB 20 nm | H2:SER1 (98%:2%) 20 nm | ETM1 30 nm | LiQ 3 nm |
| 16 | HTM1 140 nm | HIL1 5 nm | NPB 20 nm | H2:SER1 (95%:5%) 20 nm | Alq 30 nm | LiF 1 nm |
| 17 | HTM1 20 nm | | NPB 20 nm | H3:TER1 (85%:15%) 30 nm | Alq 20 nm | LiF 1 nm |
| 18 | HTM1 160 nm | | EBM1 20 nm | H3:TEG1 (90%:10%) 30 nm | ETM1:LiQ (50%:50%) 40 nm | |
| 19 | HTM1 120 nm | | NPB 20 nm | H6:TER1 (85%:15%) | Alq 20 nm | LiF 1 nm |
| 20 | HTM1 160 nm | | EBM1 20 nm | H6:TEG1 (90%:10%) | ETM1:LiQ (50%:50%) 30 nm | |
| 21 | HTM1 160 nm | | EBM1 20 nm | H6:TEG1 (90%:10%) | ETM1:LiQ (50%:50%) 40 nm | |

TABLE 2

Results for the OLEDs

| Ex. | Voltage [V] for 1000 cd/m$^2$ | Efficiency [cd/A] at 1000 cd/m$^2$ | Efficiency [lm/W] at 1000 cd/m$^2$ | CIE x/y at 1000 cd/m$^2$ | | LD50 I = 6000 cd/m$^2$ |
|---|---|---|---|---|---|---|
| 4 (comp.) | 3.4 | 10.1 | 9.4 | 0.64 | 0.34 | 1100 |
| 5 (comp.) | 3.3 | 10.5 | 10.1 | 0.64 | 0.34 | 1050 |
| 6 (comp.) | 3.1 | 13.8 | 13.8 | 0.65 | 0.33 | 730 |
| 7 (comp.) | 3.7 | 12.9 | 11.1 | 0.65 | 0.33 | 1780 |
| 8 (comp.) | 5.0 | 7.2 | 4.5 | 0.69 | 0.31 | 230* |
| 9 (comp.) | 4.6 | 54 | 37 | 0.37 | 0.60 | 400* |
| 10 | 4.7 | 7.1 | 4.7 | 0.69 | 0.31 | 420 |
| 11 | 3.8 | 57 | 47 | 0.37 | 0.61 | 1050 |
| 12 | 3.4 | 54 | 50 | 0.37 | 0.61 | 920 |
| 13 | 3.3 | 10.3 | 9.6 | 0.64 | 0.34 | 1200 |
| 14 | 3.2 | 10.8 | 10.4 | 0.64 | 0.34 | 1150 |
| 15 | 3.1 | 14.0 | 14.1 | 0.65 | 0.33 | 750 |
| 16 | 3.7 | 12.9 | 11.1 | 0.65 | 0.33 | 1850 |
| 17 | 5.0 | 8.0 | 5.1 | 0.69 | 0.31 | 330* |
| 18 | 4.6 | 61 | 42 | 0.37 | 0.60 | 490* |
| 19 | 4.7 | 7.3 | 4.9 | 0.69 | 0.31 | 480 |
| 20 | 3.7 | 60 | 51 | 0.37 | 0.61 | 1200 |
| 21 | 3.4 | 55 | 50 | 0.37 | 0.61 | 1000 |

*For these devices, the lifetime LD80 was determined from 4000 cd/m$^2$.

TABLE 3
Structural formulae of the materials used
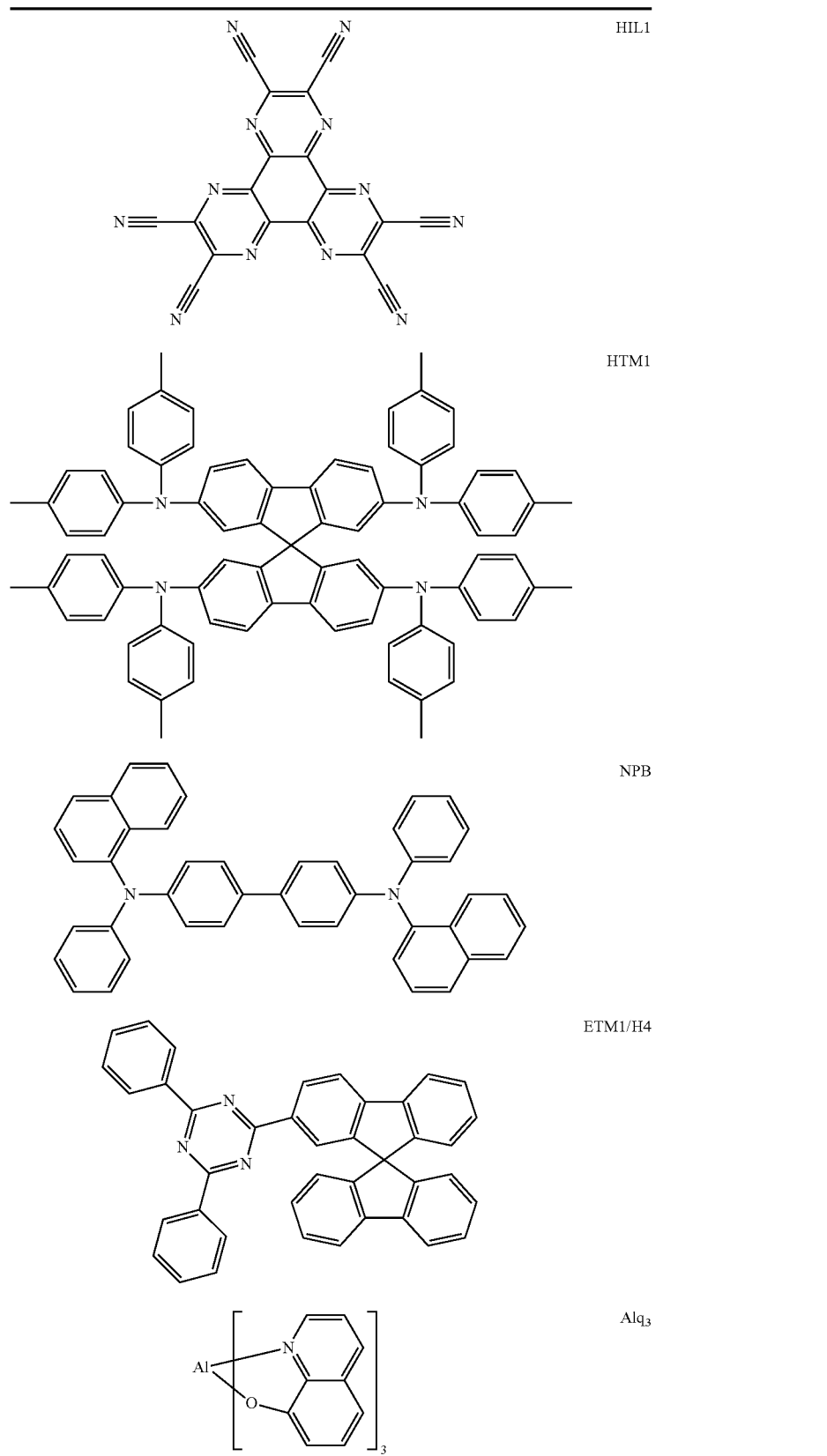

TABLE 3-continued
Structural formulae of the materials used
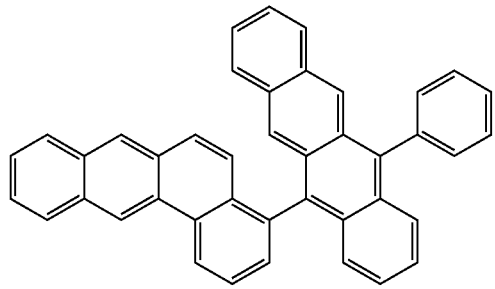 [SMILES: c1ccc(-c2c3ccccc3c(-c3cccc4c3ccc3cc5ccccc5cc34)c3cc4ccccc4cc23)cc1]
H1
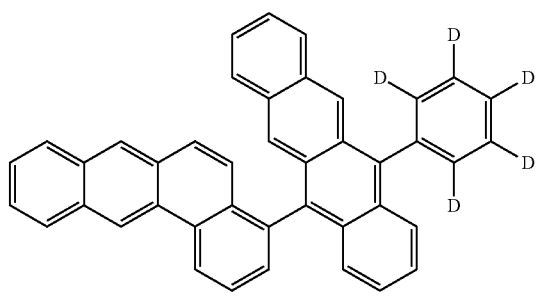 [SMILES: [2H]c1c([2H])c([2H])c(-c2c3ccccc3c(-c3cccc4c3ccc3cc5ccccc5cc34)c3cc4ccccc4cc23)c([2H])c1[2H]]
H2
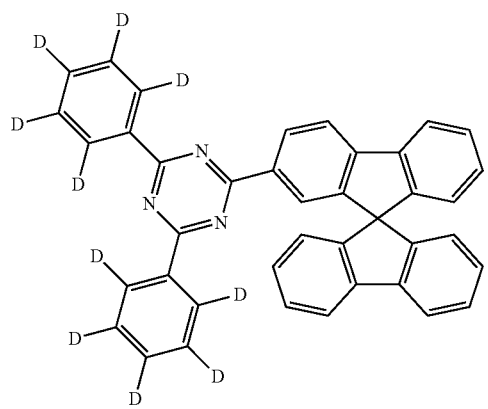 [SMILES: [2H]c1c([2H])c([2H])c(-c2nc(-c3ccc4c(c3)C3(c5ccccc5-c5ccccc53)c3ccccc3-4)nc(-c3c([2H])c([2H])c([2H])c([2H])c3[2H])n2)c([2H])c1[2H]]
H3
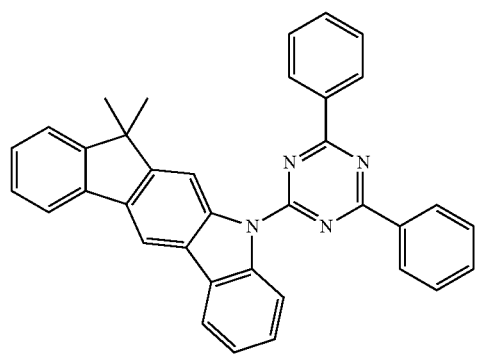 [SMILES: CC1(C)c2ccccc2-c2cc3c4ccccc4n(-c4nc(-c5ccccc5)nc(-c5ccccc5)n4)c3cc21]
H5

TABLE 3-continued
Structural formulae of the materials used
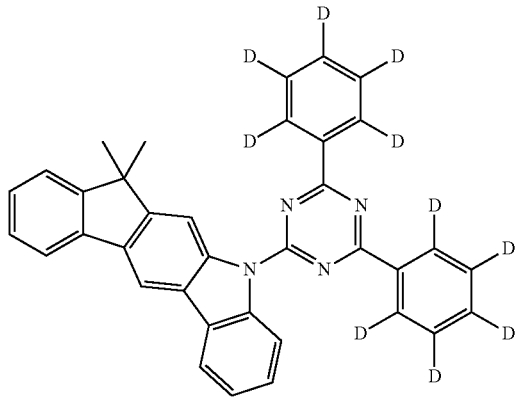 [SMILES: [2H]c1c([2H])c([2H])c(-c2nc(-c3c([2H])c([2H])c([2H])c([2H])c3[2H])nc(-n3c4ccccc4c4cc5c(cc43)C(C)(C)c3ccccc3-5)n2)c([2H])c1[2H]]
H6
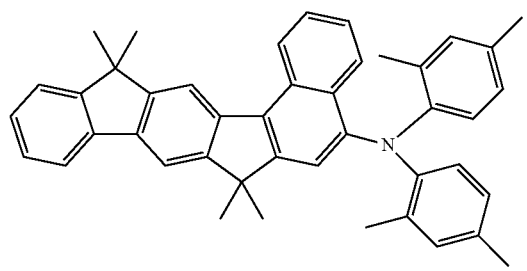 [SMILES: Cc1ccc(N(c2ccc(C)cc2C)c2cc3c(c4ccccc24)-c2cc4c(cc2C3(C)C)-c2ccccc2C4(C)C)c(C)c1]
SEB1
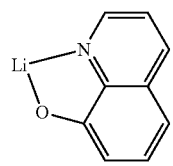
LiQ
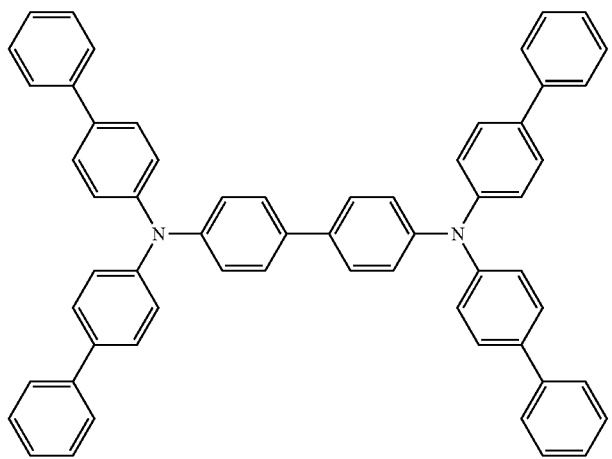 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1]
EBM1
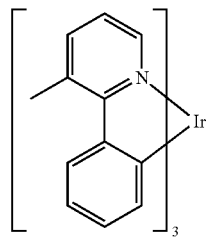
TEG1

TABLE 3-continued

Structural formulae of the materials used

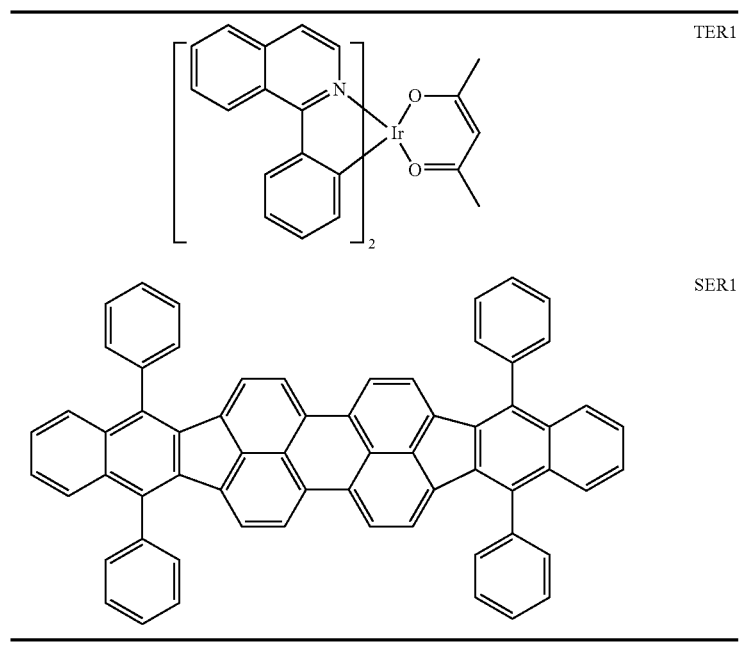

TER1

SER1

The invention claimed is:

1. A compound of the general formula (I)

Z—(Y)$_n$   formula (I), where
- Z is selected from terphenyl, triphenylene, benzocarbazole, benzonaphthofuran, benzophenanthrene, fluoranthene, benzanthracene, spirobidibenzosilole, spirobifluorene, indenofluorene, benzindenofluorene, indolocarbazole, indenocarbazole, quinacridones, which is optionally linear or angular, dibenzoquinoxaline, dibenzocinnoline, dibenzophthalazine, dibenzoquinazoline and benzacridine, where the said groups may optionally be substituted by one or more radicals R;
- Y, identically or differently on each occurrence, represents a phenyl, tolyl, biphenyl, terphenyl, diphenyltriazinyl, pyridinyl, each of which carries two or more deuterium atoms and no further substituents apart from deuterium and hydrogen;
- n can adopt a value from 1 to 15;
- R is identically or differently on each occurrence, represent H, D, F, Cl, Br, I, CN, Si(R$^2$)$_3$, NO$_2$ or a straight-chain alkyl, alkoxy or thioalkoxy group having 1 to 40 C atoms or an alkenyl or alkynyl group having 2 to 40 C atoms or a branched or cyclic alkyl, alkoxy or thioalkoxy group having 3 to 40 C atoms, each of which is optionally substituted by one or more radicals R$^2$, where one or more adjacent or non-adjacent CH$_2$ groups is optionally replaced by —C≡C—, —R$^2$C=CR$^2$—, Si(R$^2$)$_2$, C=O, C=S, C=Se, C=NR$^2$, P(=O)(R$^2$), SO, SO$_2$, NR$^2$, O, S, C(=O)O or C(=O)NR$^2$, or an aromatic or heteroaromatic ring system having 5 to 60 ring atoms, which may in each case be substituted by one or more radicals R$^2$; two or more substituents R on the group Z and/or on one or more of the groups Y is optionally linked to one another and optionally form a mono- or polycyclic aliphatic, aromatic or heteroaromatic ring system, wherein the group R does not represent a deuterium atom; and
- R$^2$ on each occurrence, identically or differently, represents H, D or an aliphatic, aromatic or heteroaromatic organic radical having 1 to 20 C atoms, in which, in addition, one or more H atoms is optionally replaced by D or F; two or more adjacent or non-adjacent radicals R$^2$ here is optionally linked to one another and optionally form a mono- or polycyclic aliphatic, aromatic or heteroaromatic ring system.

2. The compound according to claim 1, wherein for each of the groups Y, Y is fully substituted by deuterium.

3. The compound according to claim 1, wherein the compound conforms to one of the following formulae:

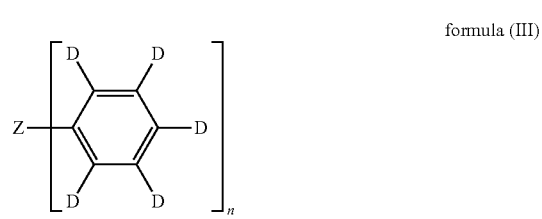

formula (III)

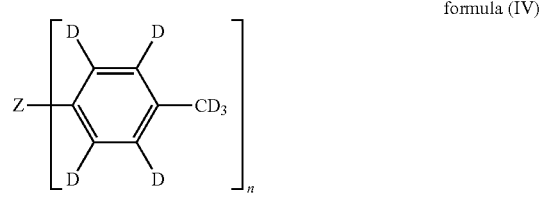

formula (IV)

107
-continued

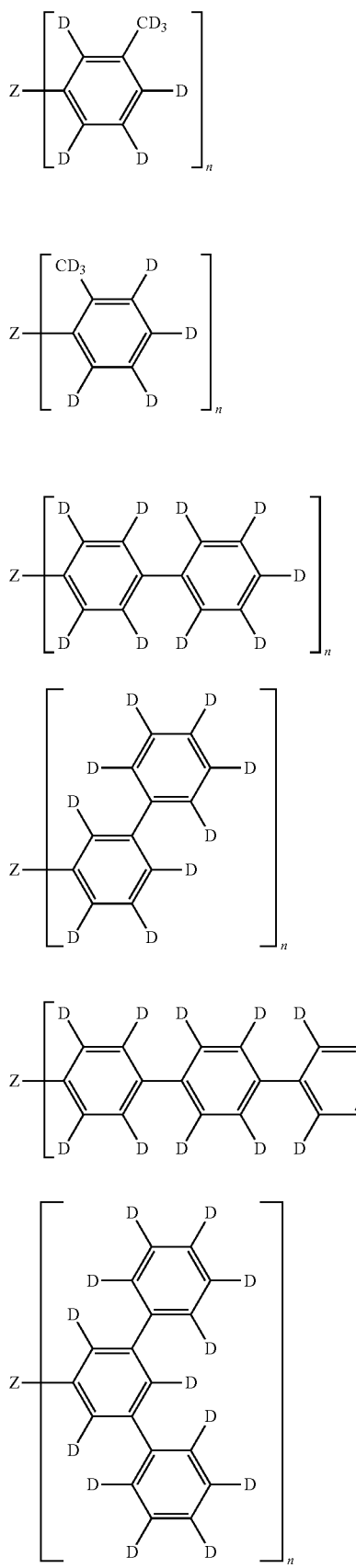

108
-continued formula (V)

formula (VI)

formula (VII)

formula (IX)

formula (X)

formula (XI)

formula (XII)

formula (XIII)

where the groups Z and the index n are as defined in claim 1.

4. The compound according to claim 1, wherein the radical R is selected on each occurrence, identically or differently, from H, F, CN, Si($R^2$)$_3$ or a straight-chain alkyl or alkoxy group having 1 to 20 C atoms or a branched or cyclic alkyl or alkoxy group having 3 to 20 C atoms, each of which is optionally substituted by one or more radicals $R^2$, where one or more adjacent or non-adjacent CH$_2$ groups is optionally replaced by —C≡C—, —$R^2$C=C$R^2$—, Si($R^2$)$_2$, C=O, C=N$R^2$, N$R^2$, O, S, C(=O)O or C(=O)N$R^2$, or an aryl or heteroaryl group having 5 to 30 aromatic ring atoms, which may in each case be substituted by one or more radicals $R^2$.

5. A process for the preparation of the compound according to claim 1, which comprises linking one or more groups Y to the group Z via an organometallic coupling reaction.

6. A mixture comprising one or more compounds of the formula (I) according to claim 1 and at least one emitter compound.

7. The mixture according to claim 6, wherein at least one fluorescent emitter compound is present, which preferably represents an aromatic or heteroaromatic ring system having 5 to 60 aromatic ring atoms, which is optionally substituted by one or more substituents $R^3$, where $R^3$, identically or differently on each occurrence, represents H, D, F, Cl, Br, I, CN, N($R^4$)$_2$, N(Ar)$_2$, NO$_2$, Si($R^4$)$_3$ or a straight-chain alkyl, alkoxy or thioalkoxy group having 1 to 40 C atoms or an alkenyl or alkynyl group having 2 to 40 C atoms or a branched or cyclic alkyl, alkoxy or thioalkoxy group having 3 to 40 C atoms, each of which is optionally substituted by one or more radicals $R^4$, where one or more adjacent or non-adjacent CH$_2$ groups is optionally replaced by —C≡C—, —$R^4$C=C$R^4$—, Si($R^4$)$_2$, C=O, C=S, C=Se, C=N$R^4$, P(=O)($R^4$), SO, SO$_2$, N$R^4$, O, S, C(=O)O or C(=O)NR$^4$; two or more substituents R$^3$ here is optionally linked to one another and optionally form a mono- or polycyclic aliphatic, aromatic or heteroaromatic ring system, and in addition Ar on each occurrence, identically or differently, represents an aryl group having 6 to 60 C atoms, which may optionally be substituted by one or more substituents R$^4$, and R$^4$ on each occurrence, identically or differently, is H, D or an aliphatic, aromatic or heteroaromatic organic radical having 1 to 20 C atoms, in which, in addition, one or more H atoms is optionally replaced by D or F; two or more adjacent or non-adjacent radicals R$^4$ here is optionally linked to one another and optionally form a mono- or polycyclic aliphatic, aromatic or heteroaromatic ring system.

8. The mixture according to claim 6, wherein at least one phosphorescent emitter compound is present.

9. The mixture according to claim 6, wherein at least one phosphorescent emitter compound is present, and is selected from organometallic complexes having at least one metal-carbon bond which contain a metal selected from the group consisting of chromium, molybdenum, tungsten, rhenium, ruthenium, osmium, rhodium, iridium, nickel, palladium, platinum, copper, silver and gold.

10. A formulation comprising at least one compound according to claim 1 and at least one solvent.

11. A formulation comprising at least one mixture according to claim 6 and at least one solvent.

12. An electronic device comprising at least one compound according to claim 1.

13. An electronic device comprising at least one mixture according to claim 6.

14. The electronic device according to claim 12, wherein the device is an organic electroluminescent device (OLED), an organic field-effect transistor (O-FET), an organic thin-film transistor (O-TFT), an organic light-emitting transistor (O-LET), an organic integrated circuit (O-IC), an organic solar cell (O-SC), an organic field-quench device (O-FQD), a light-emitting electrochemical cell (LEC), an organic laser diode (O-laser) or an organic photoreceptor.

15. An electronic device comprising one or more compounds according to claim 1 as a host material in an emitting layer together with one or more emitter compounds.

16. A compound of the general formula (I)

Z—(Y)$_n$ 

where

Z is terphenyl, triphenylene, spirobifluorene, benzophenanthrene, fluoranthene, benzanthracene, or a heteroaryl group having 15 to 40 aromatic ring atoms, which is optionally substituted by one or more radicals R, Y, identically or differently on each occurrence, represents a phenyl, tolyl, biphenyl, terphenyl, diphenyltriazinyl, pyridinyl, each of which carries two or more deuterium atoms and no further substituents apart from deuterium and hydrogen;

n can adopt a value from 1 to 15;

R is identically or differently on each occurrence, represent H, D, F, Cl, Br, I, CN, Si(R$^2$)$_3$, NO$_2$ or a straight-chain alkyl, alkoxy or thioalkoxy group having 1 to 40 C atoms or an alkenyl or alkynyl group having 2 to 40 C atoms or a branched or cyclic alkyl, alkoxy or thioalkoxy group having 3 to 40 C atoms, each of which is optionally substituted by one or more radicals R$^2$, where one or more adjacent or non-adjacent CH$_2$ groups is optionally replaced by —C≡C—, —R$^2$C=CR$^2$—, Si(R$^2$)$_2$, C=O, C=S, C=Se, C=NR$^2$, P(=O)(R$^2$), SO, SO$_2$, NR$^2$, O, S, C(=O)O or C(=O)NR$^2$, or an aromatic or heteroaromatic ring system having 5 to 60 ring atoms, which may in each case be substituted by one or more radicals R$^2$; two or more substituents R or R$^1$ on the group Z and/or on one or more of the groups Y is optionally linked to one another and optionally form a mono- or polycyclic aliphatic, aromatic or heteroaromatic ring system, wherein the group R does not represent a deuterium atom; and R$^2$ on each occurrence, identically or differently, represents H, D or an aliphatic, aromatic or heteroaromatic organic radical having 1 to 20 C atoms, in which, in addition, one or more H atoms is optionally replaced by D or F.

17. The compound according to claim 16, wherein the radical R is selected on each occurrence, identically or differently, from H, F, CN, Si(R$^2$)$_3$ or a straight-chain alkyl or alkoxy group having 1 to 20 C atoms or a branched or cyclic alkyl or alkoxy group having 3 to 20 C atoms, each of which is optionally substituted by one or more radicals R$^2$, where one or more adjacent or non-adjacent CH$_2$ groups is optionally replaced by a single bond, C=O, C=NR$^2$, NR$^2$, O, S, C(=O)O or C(=O)NR$^2$, or R is an aryl or heteroaryl group having 5 to 30 aromatic ring atoms, which may in each case be substituted by one or more radicals R$^2$.

18. The compound according to claim 16, wherein for each of the groups Y, Y is fully substituted by deuterium.

19. The compound according to claim 16, wherein the compound conforms to one of the following formulae:

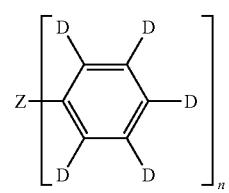

formula (III)

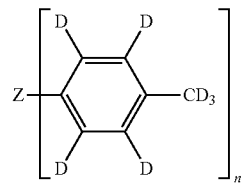

formula (IV)

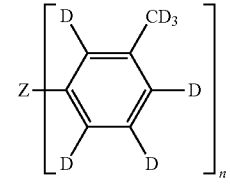

formula (V)

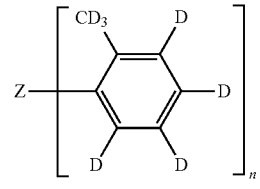

formula (VI)

formula (VII)
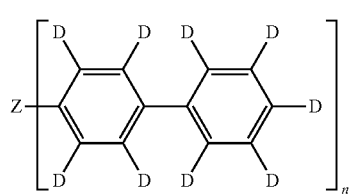
formula (IX)
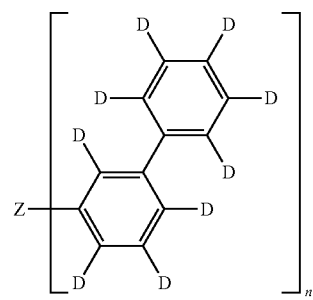
formula (X)
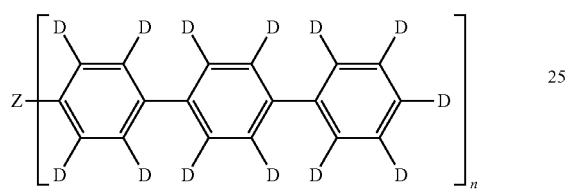
formula (XI)
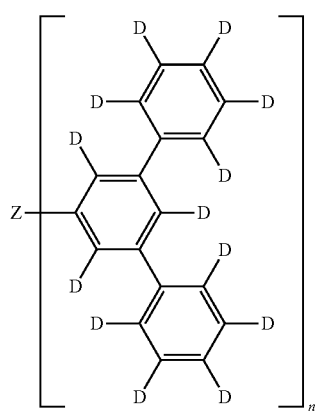
formula (XII)
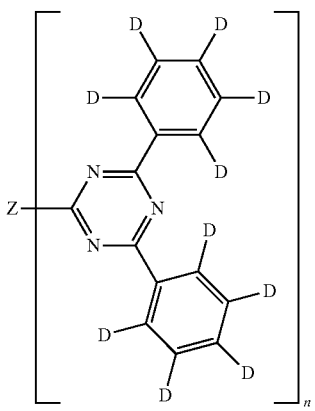
or,
formula (XIII)
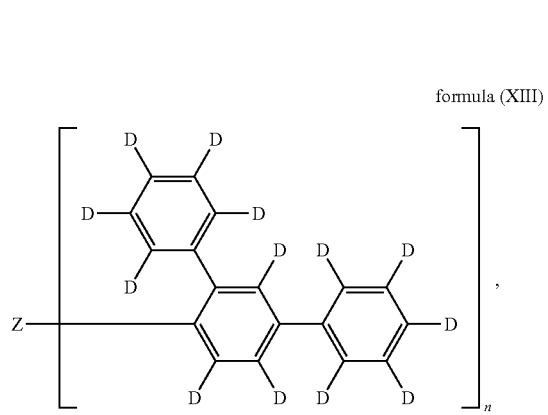
where the groups Z and the index n are as defined in claim 16.
20. An electronic device comprising at least one compound according to claim 17.
* * * * *